United States Patent
Isaacs et al.

(10) Patent No.: US 9,956,229 B2
(45) Date of Patent: May 1, 2018

(54) ACYCLIC CUCURBIT[N]URIL TYPE MOLECULAR CONTAINERS TO TREAT INTOXICATION AND DECREASE RELAPSE RATE IN SUBSTANCE ABUSE DISORDERS

(71) Applicants: UNIVERSITY OF MARYLAND, COLLEGE PARK, College Park, MD (US); THE GENERAL HOSPITAL CORPORATION, Boston, MA (US)

(72) Inventors: Lyle David Isaacs, Silver Spring, MD (US); Matthias Eikermann, Cambridge, MA (US); Cristina Cusin, Boston, MA (US); Joseph Cotten, Grafton, MA (US)

(73) Assignees: University of Maryland, College Park, College Park, MD (US); General Hospital Corporation, Boston, MA (US)

(*) Notice: Subject to any disclaimer, the term of this patent is extended or adjusted under 35 U.S.C. 154(b) by 0 days. days.

(21) Appl. No.: 15/519,330

(22) PCT Filed: Oct. 19, 2015

(86) PCT No.: PCT/US2015/056192
§ 371 (c)(1),
(2) Date: Apr. 14, 2017

(87) PCT Pub. No.: WO2016/061571
PCT Pub. Date: Apr. 21, 2016

(65) Prior Publication Data
US 2017/0246180 A1    Aug. 31, 2017

Related U.S. Application Data

(60) Provisional application No. 62/065,627, filed on Oct. 18, 2014.

(51) Int. Cl.
*A61K 31/551* (2006.01)
*A61K 47/48* (2006.01)

(52) U.S. Cl.
CPC ...... *A61K 31/551* (2013.01); *A61K 47/48215* (2013.01)

(58) Field of Classification Search
CPC .................................................. A61K 31/551
See application file for complete search history.

(56) References Cited

U.S. PATENT DOCUMENTS

| | | |
|---|---|---|
| 6,793,839 B1 | 9/2004 | Day et al. |
| 2005/0080068 A1 | 4/2005 | Isaacs et al. |
| 2014/0094529 A1 | 4/2014 | Isaacs et al. |

OTHER PUBLICATIONS

Vippagunta et al. (2001).*
Wheate, N., Improving platinum(II)-based anticancer drug delivery using cucurbit[n]urils, Journal of Inorganic Biochemistry, 2008, vol. 102, pp. 2060-2066.
Wang, G.Q., et al., Competitive supramolecular interaction of carbachol and berberine with cucurbit[7]uril and its analytical application, Microchemical Journal, 2013, vol. 110, pp. 285-291.

* cited by examiner

*Primary Examiner* — Paul V Ward
(74) *Attorney, Agent, or Firm* — Hodgson Russ LLP

(57) ABSTRACT

Provided are methods for reversing the effects of drugs of abuse. The method involves administering acyclic CB[n]-type compounds to a mammal in need of the reversal of the effects from a drug of abuse.

14 Claims, 57 Drawing Sheets

| | Before Muscle I | | | 30 minutes after Muscle I | | | |
|---|---|---|---|---|---|---|---|
| Drug | pH | $pCO_2$ (mmHg) | $pO_2$ (mmHg) | pH | $pCO_2$ (mmHg) | $pO_2$ (mmHg) | N |
| Placebo | 7.42 ± 0.02 | 42 ± 6 | 176 ± 20 | 7.42 ± 0.04 | 41 ± 3 | 171 ± 27 | 5 |
| Muscle I 30 mg/kg$^{-1}$ | 7.42 ± 0.03 | 42 ± 3 | 185 ± 40 | 7.42 ± 0.03 | 39 ± 2 | 179 ± 42 | 5 |
| Muscle I 60 mg/kg$^{-1}$ | 7.43 ± 0.03 | 44 ± 6 | 147 ± 6 | 7.43 ± 0.02 | 40 ± 6 | 176 ± 76 | 5 |
| Muscle I 90 mg/kg$^{-1}$ | 7.42 ± 0.01 | 43 ± 2 | 176 ± 29 | 7.41 ± 0.01 | 41 ± 2 | 187 ± 21 | 5 |

(A)

(B)

(A)

(B)

(A)

(B)

(A)

(B)

ACYCLIC CUCURBIT[N]URIL TYPE MOLECULAR CONTAINERS TO TREAT INTOXICATION AND DECREASE RELAPSE RATE IN SUBSTANCE ABUSE DISORDERS

CROSS-REFERENCE TO RELATED APPLICATIONS

This application claims priority to U.S. provisional patent application No. 62/065,627, filed Oct. 18, 2014, the disclosure of which is incorporated herein by reference.

FIELD

The present invention relates generally to reversal of the effects of agents which cause intoxication and/or dependency.

BACKGROUND

Deaths from drug overdose have been rising steadily over the past two decades and have become the leading cause of injury death in the United States. In 2011, 33,071 (80%) of the 41,340 drug overdose deaths in the United States were unintentional, 5,298 (12.8%) were of suicidal intent, 80 (0.2%) were homicides, and 2,891 (7%) were of undetermined intent. In 2011, drug misuse and abuse caused about 2.5 million emergency department (ED) visits. Of these, more than 1.4 million ED visits were related to pharmaceuticals. The present disclosure provides compositions and methods for addressing these and other circumstances wherein it is desirable to reverse the effect of one or more drugs, including but not necessarily limited to drugs of abuse.

BRIEF SUMMARY

The present invention provides a method for reversal of the effects of intoxication agents. The method comprises administering a composition comprising a compound of the invention to an individual in need thereof such that the effects of the agent(s) are partially or fully reduced. The compositions used in the present invention contain compound(s) having the following structure:

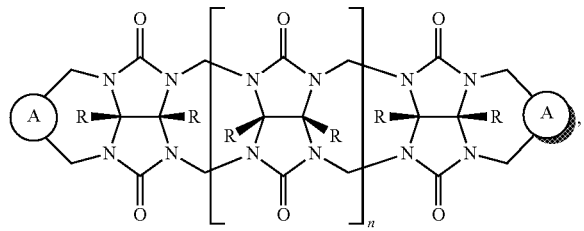

where each R is independently hydrogen, $C_1$ to $C_{20}$ alkyl group, $C_3$ to $C_{20}$ carbocyclic group, $C_1$ to $C_{20}$ heterocyclic group, carboxylic acid group, ester group, amide group, hydroxy, or ether group. Optionally, adjacent R groups form a $C_3$ to $C_{20}$ carbocyclic ring or heterocyclic ring. Each

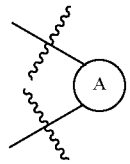

is independently a $C_5$ to $C_{20}$ carbocyclic ring system or $C_2$ to $C_{20}$ heterocyclic ring system, where the ring system comprises one or more rings. At least one of the ring systems has at least one solubilizing group selected from sulfonic acid, sulfonate salt, phosphonic acid, phosphonate salt, and polyethylene glycol. Optionally, the ring system has a targeting group. The value of n is 1 to 5. The method comprises administering to an individual an effective amount of a compound of this disclosure such that one or more of the effects of an intoxicating agent in the individual is reduced. In embodiments, the individual is in need of a reduction of the effect of cocaine, fentanyl, methamphetamine, or any combination thereof. In an embodiment the disclosure includes a proviso that the individual is not in need of reversal of ketamine.

Box-plot showing median, interquartile range, 10 and 90 percent percentile, as well as outer fence. Methamphetamine compared to placebo (saline) markedly increased total distance traveled of living rats in an open field. Calabadion 2 dose-dependently inhibited these methamphetamine-induced effects such that at the highest calabadion 2 dose total distance traveled did not differ between rats given methamphetamine and those who did not receive methamphetamine.

Figure 72:
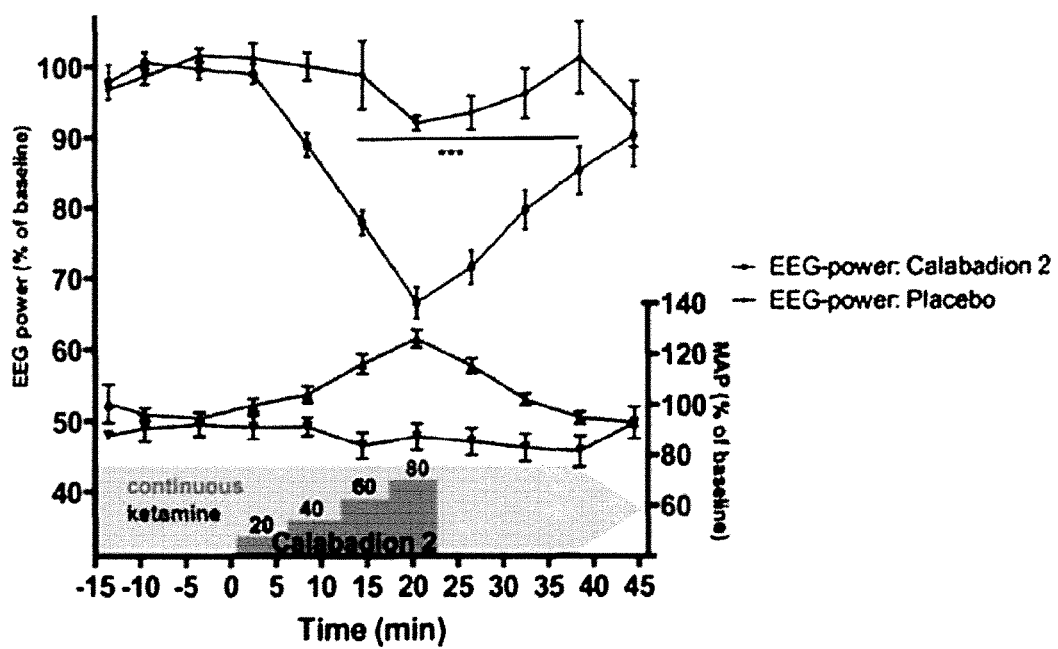

FIG. 72. Calabadion 2 decreases levels of unconsciousness during continuous administered anesthesia with ketamine. Effect of an escalating Calabadion 2 i.v. infusion on electroencephalographic power (EEG-power) and mean arterial blood pressure (MAP) during continuous ketamine infusion (titrated to an average dose of 122.3 µg/kg/min; n=13). Calabadion 2 decreased EEG power during ketamine infusion in a dose dependent fashion and increased the MAP accordingly (*p<0.001). EEG power is displayed as % values from baseline (average value during continuous etomidate/ketamine infusion before test drug infusion). MAP is displayed as % of mean MAP before start of ketamine administration. Data are ±SEM.

Figure 73:
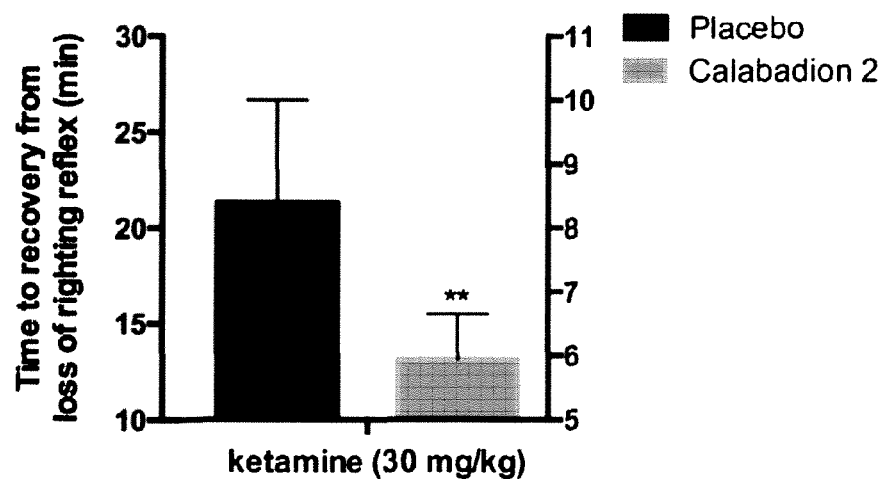

FIG. 73. Calabadion 2 accelerated recovery from single bolus anesthesia with ketamine. Effect of Calabadion 2 (80 mg/kg, i.v.) on time to recovery from LORR following administration of a single i.v. bolus of ketamine (30 mg/kg, n=7, **p=0.023). Data are ±SD.

Figure 74:
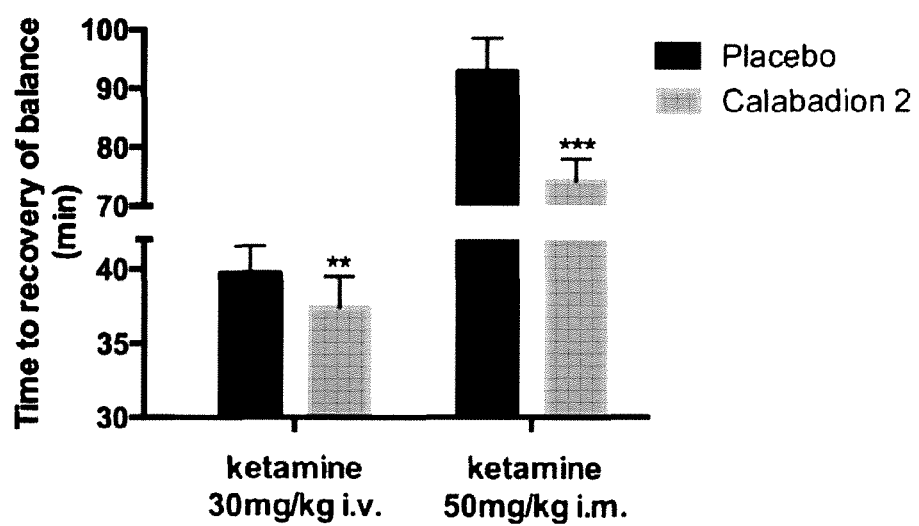

FIG. 74: Calabadion 2 accelerated recovery from post-ketamine functional mobility impairment. Effect of Calabadion 2 on time to recovery of balance following administration of a single bolus of ketamine (30 mg/kg i.v.; n=7; 50 mg/kg i.m.; n=7) vs. placebo. Recovery time was significantly shorter following Calabadion 2 vs. placebo (*p<0.001, p=0.009). Data are ±SEM.

Figure 75:
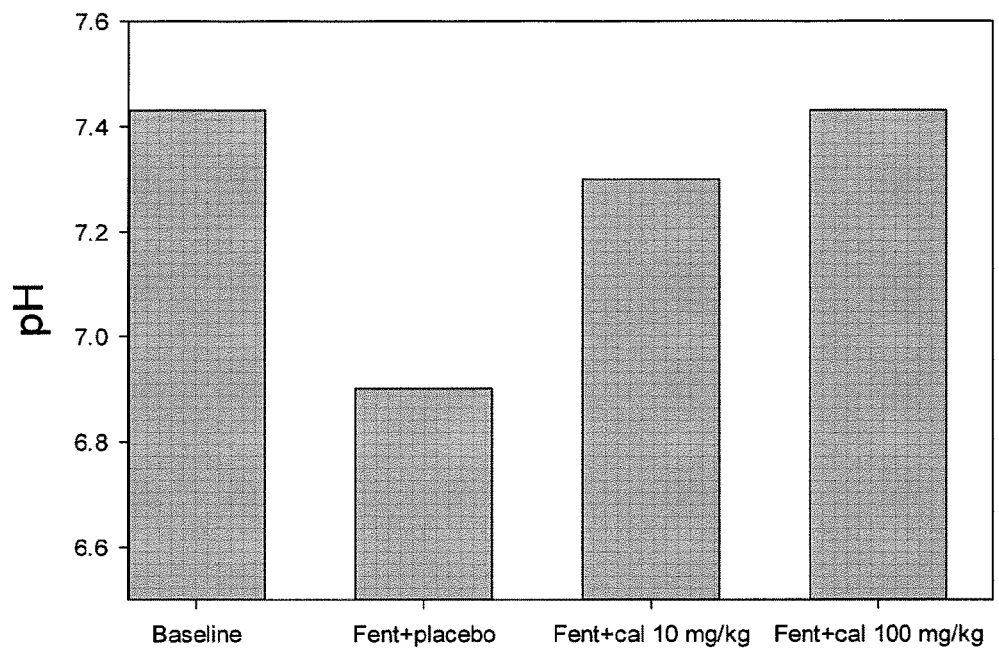
Figure 75:
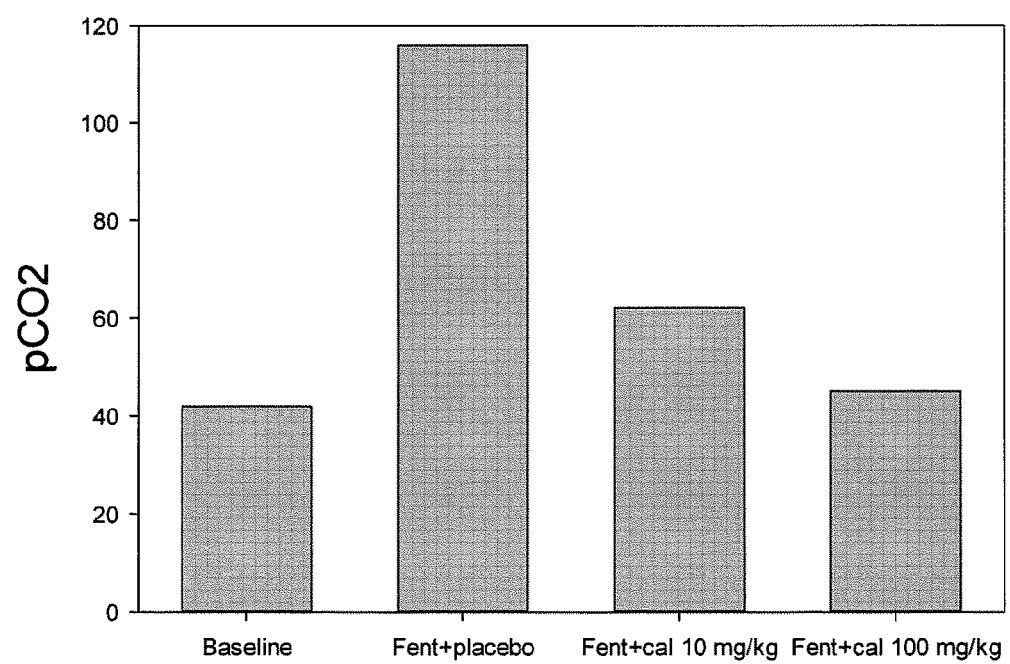

FIG. 75: Calabadion 2 reverses fentanyl-induced respiratory depression. Individual data from three different rats are shown (baseline: average from three rats). Fentanyl induces a substantial decrease in pH and arterial carbon dioxide concentration (in mm Hg). Calabadion 2 decreases these respiratory depressant effects of fentanyl in a dose dependent fashion such that values of pH and arterial carbon dioxide concentration observed at calabadion 100 mg/kg with fentanyl did not differ from values observed at baseline in the absence of opioid effects.

Figure 76:
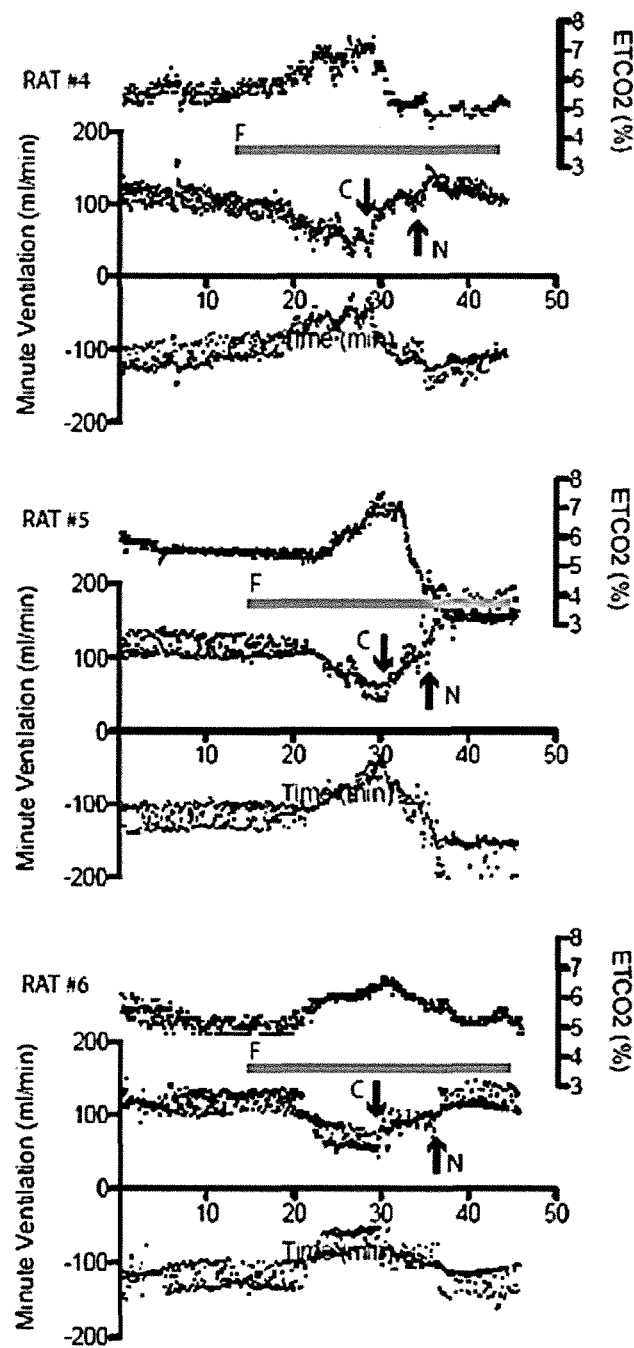

FIG. 76: Calabadion 2 reverses fentanyl-induced respiratory depression. Individual data from three different rats are shown. Exhaled end-tidal $CO_2$ (in % atmosphere) is shown at the top of each figure. Minute ventilation (in ml/min), both exhaled and inhaled, are reported. The blue bar indicates fentanyl infusion. F, fentanyl infusion (25 mcg/kg IV over 30 mins); C, calabadion 2 (100 mg/kg IV bolus); and N, naloxone (1 mg/kg IV bolus). Each data point was derived from 4 seconds of data.

Figure 77:
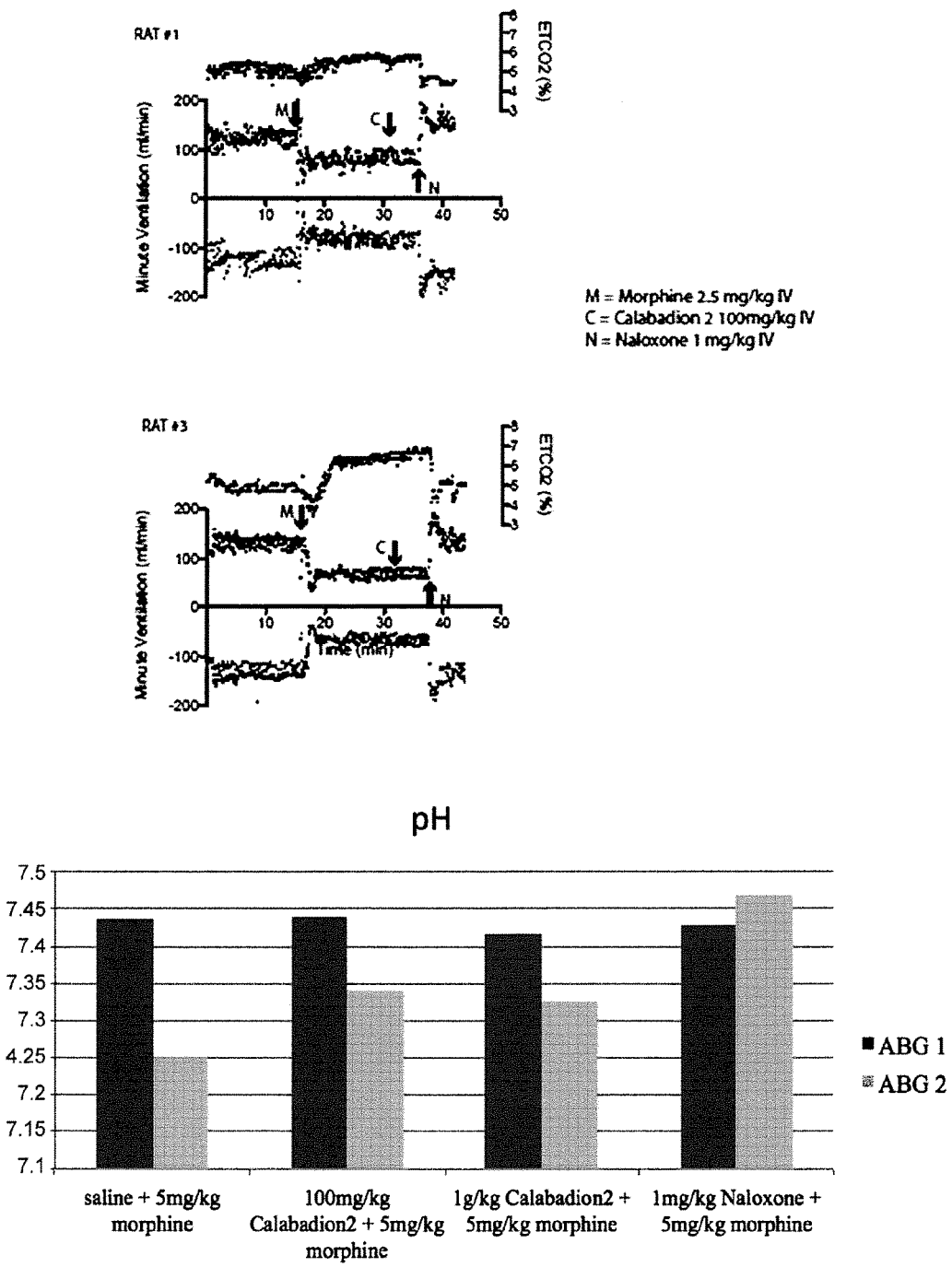

FIG. 77: Calabadion does not reverse the effects of the opioid morphine. The top panel summarizes data showing Assessment of breathing and Co2 via pneumothachograph. Morphine (M) was given following calabadion 100 mg/kg (C) and the opioid antagonist naloxone (N). Experiments were conducted in living rats. Calabadion 100 mg/kg did not reverse the respiratory depressant effects of morphine. Following Naloxone, in contrast to calabadion, carbon dioxide and minute volume almost recovered to baseline. The bottom panel shows data obtained from 4 living rats with arterial lines and results from treating with Calabadion 100 mg/kg, 1 g/kg, placebo, or saline (placebo). It is apparent that Calabadion up to 1 g/kg did not affect morphine-induced respiratory depression (low pH) using methods similar to demonstrate efficacy of compounds of this disclosure for reversal of effects of fentanyl.

DETAILED DESCRIPTION

The present invention is related to the use of compositions that are further described below for reversal of the effects of intoxicating agents, as well as for reversal of the effects of other agents that are more fully described herein. In various embodiments the invention is suitable for use in reversal of drug-induced neuromuscular block, or for reversal of anesthesia, or for reversal of the effects of ingestion of a drug of abuse, or an antidepressant or other agents which will be apparent to those skilled in the art given the benefit of the present specification. In embodiments, the disclosure includes reversing the effect of one or more agents which include but are not limited to cocaine, an amphetamine, ketamine, methamphetamine, phencyclidine [PCP]), a drug used in inperioperative medicine, including but not necessarily limited to local anesthetics, beta-blockers, neurolepts, anticholinergic agents, or a combination of any of said agents. In non-limiting and illustrative embodiments, the reversal is achieved by administering to the individual a composition comprising Calabadion 1 or Calabadion 2 which are further described below. In one embodiment the method encompasses reversal of intoxication by cocaine, fentanyl, or methamphetamine, or any combination thereof. Thus in embodiments, a composition comprising one or a combination of compounds described herein is administered to an individual in need of treatment due to ingestion of at least one of cocaine, fentanyl, or methamphetamine. While certain aspects of the disclosure are illustrated using ketamine, the disclosure includes a proviso that the individual to which a composition of this disclosure is administered is not in need for a reduction of the effect of ketamine, or for other anesthetic agents generally. In this regard, it will be evident to those skilled in the art that ketamine is a general anesthetic meaning it suppresses central nervous system activity and results in unconsciousness and lack of sensation. Its mechanism of action is well known to act through antagonism of the N-methyl-D-aspartate (NMDA) receptor. Ketamine is typically injected either intravenously or intramuscularly. At low doses, ketamine can induce systemic analgesia, and also has an antidepressant effect. Ketamine can also produce hallucinations. Thus, in one example, the disclosure is not used to treat an individual in need of treatment for ingestion of an NMDA receptor antagonist.

In contrast to ketamine and other anesthetic agents, cocaine and methamphetamine do not provide anesthesia. Instead, methamphetamine and cocaine belong to the broad class of drugs called psychostimulants that also includes amphetamine and methylphenidate. The two drugs often are compared to each other because they produce similar mood-altering effects and both have a high potential for abuse and dependence.

The present disclosure also provides for reversal of the effects of fentanyl. This is in contrast to the demonstration that compounds of this disclosure are not effective in reversing the effects of morphine (e.g., see FIG. 77), and thus the disclosure presents unexpected results.

The invention provides for partial or full reversal of the effects of the agents. The degree of reversal of the effect of any particular agent can be determined, for instance, for any particular dosage or time point using techniques known to the skilled artisan.

In general, Neuromuscular blocking agents (NMBAs), the effects of which can be reversed by the invention, can be divided into two categories that relate to their mechanism of action on certain cellular receptors. These categories are depolarizing NMBA and non-depolarizing NMBAs.

Without intending to be constrained by any particular theory, depolarizing NMBAs are considered to act by binding to nicotinic acetylcholine receptors (nAChRs) at the neuromuscular junction, which results in an initial opening of the ion channel associated with the particular nAChR. Thus, depolarizing NMBAs mimic the activity of acetylcholine, which is an endogenously produced neurotransmitter. However, depolarizing NMBAs are metabolized relatively slowly by cholinesterase enzymes, which stands in contrast to the rapid hydrolysis of endogenous acetylcholine by acetylcholinesterases. Accordingly, depolarizing NMBAs bind to nAChRs for a much longer time period than acetylcholine. Consequently they effect a persistent depolarization of the plasma membrane of skeletal muscle fiber, which makes the muscle fiber resistant to further stimulation by acetylcholine, which in turn results in a neuromuscular block.

In contrast to depolarizing NMBAs, non-depolarizing NMBAs are competitive inhibitors of nAChRs which do not activate the ion channel when bound to the nAChR. Instead, they block the activation of the channel by acetylcholine and thereby prevent cell membrane depolarization. This results in flaccid muscle tissue.

In various embodiments, the invention facilitates reversal of neuromuscular block induced by an NMBA that is a competitive inhibitor of nAChRs (which prevents the physiological agonist, acetylcholine, from depolarizing the skeletal muscles). Consequently, the invention will restore the skeletal muscle function in various embodiments within a few seconds.

Most clinically-used NMBAs belong to the non-depolarizing category. These include but are not necessarily limited to steroidal and benzylisoquinoline-type neuromuscular blocking agents. Those skilled in the art will readily recognize the structures of commercially available non-depolarizing NMBAs, the effects of any of which can be reversed by performing the method of the invention. Such NMBAs include but are not necessarily limited to those agents which are generally referred to in the art as rocuronium, tubocurarine, atracurium, atracurium besylate, cisatracurium, mivacurium, gallamine, pancuronium, vecuronium, doxacurium, metocurine, and rapacuronium. Therefore, the invention is suitable for reversing the effects of each of the compounds individually, or the effects of combinations of these compounds. Illustrative structures of each of these compounds are as follows:

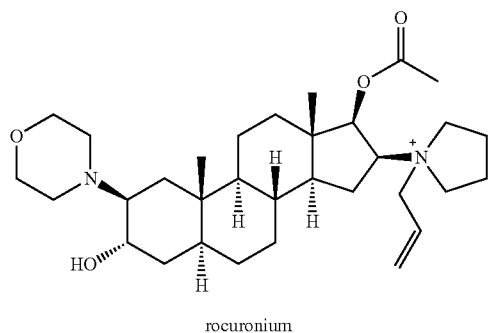

rocuronium

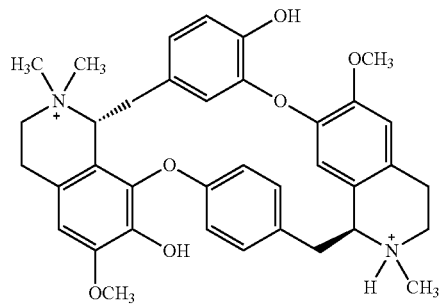

tubocurarine

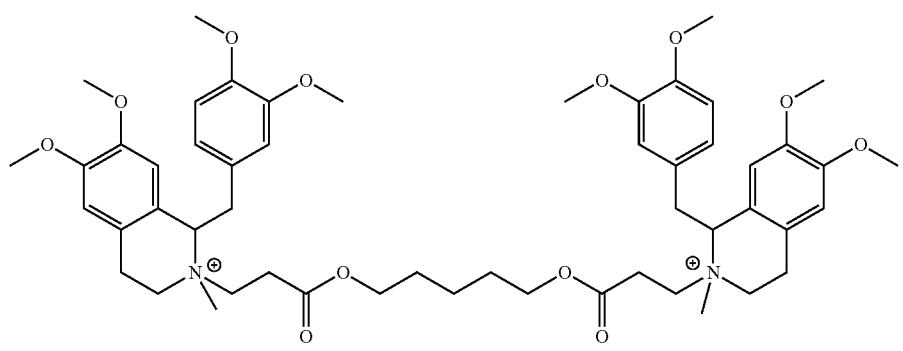

atracurium

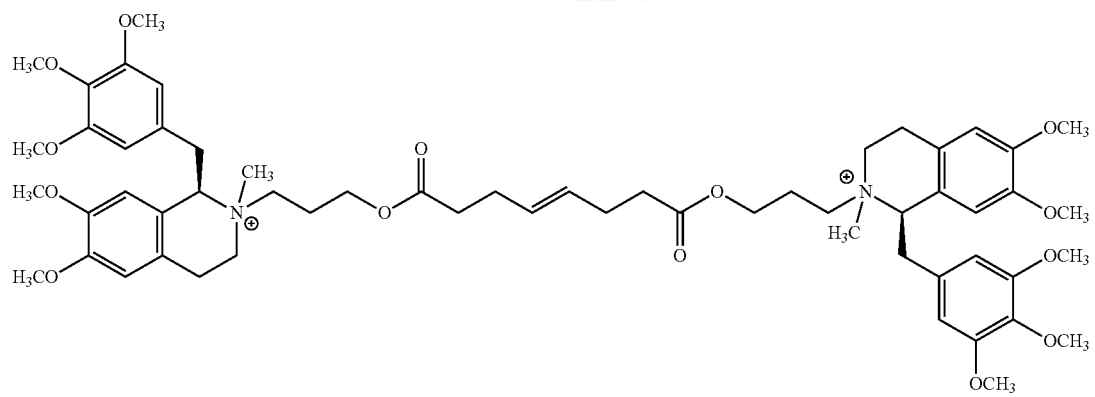
mivacurium
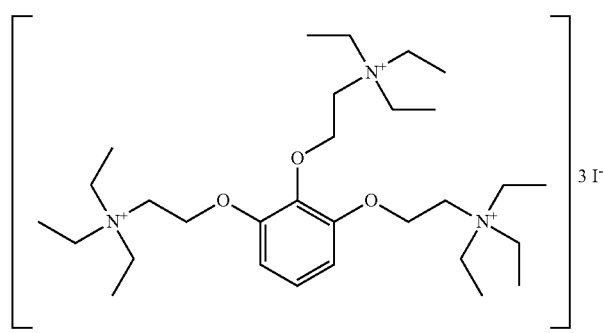
gallamine
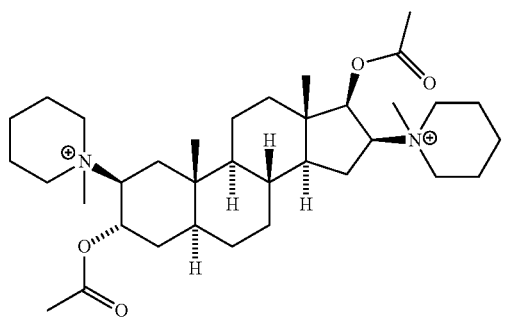
pancuronium
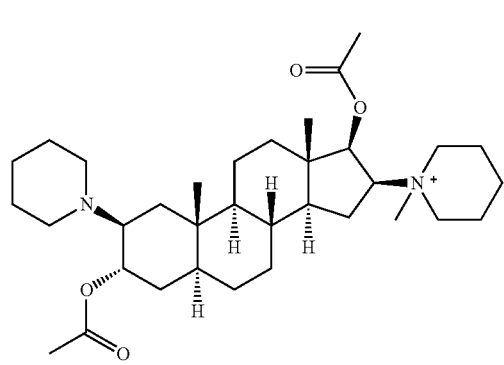
vecuronium
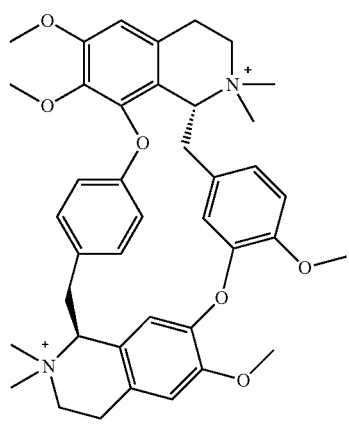
metocurine

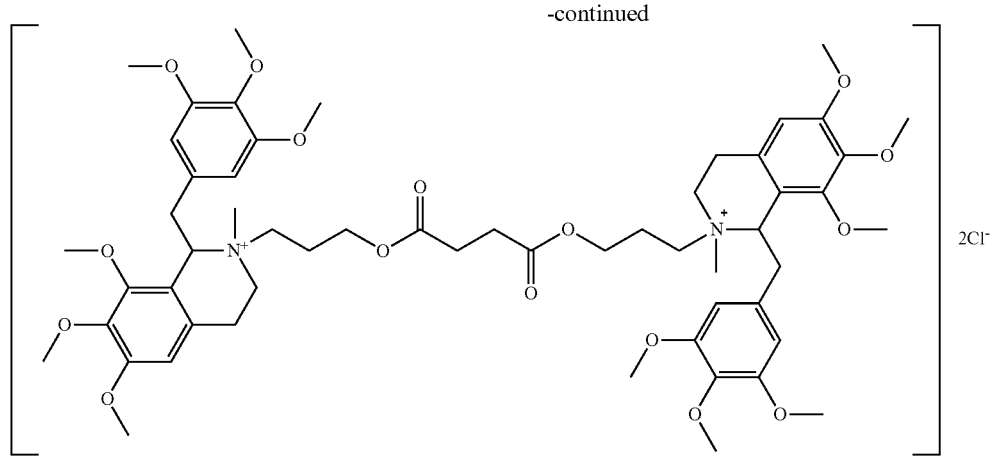

doxacurium

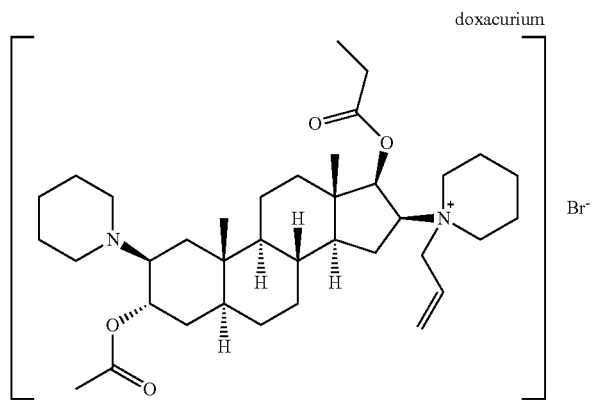

rapacuronium

In various embodiments, the compound for which the effects are reversed according to the method of the invention is provided in a form according to the foregoing structures, and includes salts, partial salts, hydrates, polymorphs, stereoisomers or a mixtures thereof. Each compound can be provided as a racemic mixture, a single enantiomer, a single diastereomer, mixture of enantiomers, or mixture of diastereomers.

Since NMBAs are used during surgery and/or for muscle relaxation during intensive care, and in Emergency Medicine, at or near the end of these treatment modalities, it is desirable to reverse the effects of the NMBA so that the patient can regain voluntary control over muscular contractions. Thus, in one embodiment, the present invention comprises administering a composition comprising a compound of the invention to an individual who is in need of reversal of a chemically induced muscular block. Accordingly, in various embodiments, the compounds of the invention can be considered to be NMBA reversal agents, or NMBA sequestrants.

The present invention also includes a method for reversing the activity of certain anesthetic agents and other intoxicating agents as described further in Example 6. In this regard, in the United States, nearly 60,000 patients per day receive general anesthesia for surgery. The most severe anesthesia-related patient injuries are death or permanent brain damage, which frequently results from adverse effects of anesthetics on breathing. Further, anesthetics decrease respiratory drive and place the upper airway at risk for collapse. Typically, skilled anesthesiologists can artificially ventilate the patient in a situation where the patient is unable to breathe because of adverse effects of anesthetics and neuromuscular blocking agents. However, in some patients, artificial ventilation is difficult or impossible because the patient has an airway anatomy that does not allow inflation of the lung. The second most common life threatening side effects of anesthetics relates to depression of cardiovascular function, which can be associated with insufficient oxygen supply to the heart, leading to myocardial infarction and/or cardiac arrest. In such emergent situations, it would be desirable to reverse the effects of anesthesia and NMBAs, but this typically requires waiting until emergence (the time of recovery of consciousness and neuromuscular transmission from drug effects), such that breathing and adequate circulation of blood are restored. Emergence from general anesthesia has been treated as a passive process whereby anesthetic drugs are merely discontinued at the end of surgery and no drugs are administered to actively reverse their effects on the brain and central nervous system. The timing of emergence can be unpredictable because many factors, including the type of surgery and the age, physical condition of the patient affects the pharmacokinetics and pharmacodynamics of general anesthetics. Although the actions of many drugs used in anesthesiology are reversed pharmacologically when no longer desired (e.g., some muscle relaxants, or opioids such as morphine), this is not the case for general anesthetic induced loss of consciousness. Until the previous invention, there was no agent available to actively induce emergence from general anesthesia. However, we now demonstrate feasibility of the present invention for reversing activity of anesthetics.

In particular, we show that the effects of a certain group of anesthetics, N-methyl D-aspartate (NMDA) receptor antagonists, such as ketamine, can be reversed using the instant method. Ketamine is primarily used for the induction and maintenance of general anesthesia. It is also used for monitored anesthesia care, also known as conscious sedation, and as an analgesic, both in humans and in veterinary medicine. In the present case, we administered by continuous infusion ketamine to rats to induce steady-state, deep anesthesia, resulting in depression of respiratory and cardiovascular function. The effects of Motor2 induced reversal of ketamine anesthesia are striking: the rat woke up within 2 minutes following injection of Motor2 (200 mg). Respiratory rate and arterial blood pressure increased, an electroencephalogram (EEG) showed wakefulness-like electrical activity. Thus, since ketamine is frequently used for human and non-human animal anesthesia, in various embodiments of the invention, the individual in which a reversal of the effects of an NMBA or an anesthetic agent can be a human or a non-human animal, and includes but is not necessarily limited to any mammal. In certain embodiments, the animal in need of a composition of the invention is a human, a feline, a canine, an equine or a bovine animal. Thus, the invention has broad applicability in a variety of medical interventions and across various species.

In certain embodiments, the invention is also useful for reversing the effects of short acting anesthetics, such as etomidate. Etomidate, similar to ketamine, is a short acting anesthetic agent which is typically administered intravenously for the induction of general anesthesia for medical procedures which can be performed in relatively short time frames, such as for correction of dislocated joints.

Extracorporal application of the compositions of the invention is also contemplated. For instance, compounds of the invention could be used by mixing the compositions with a biological fluid from an individual, such as during dialysis or during plasmapheresis. Therefore, in various embodiments, the invention provides an extracorporal composition comprising a compound of the invention. The extracorporal composition, to the extent it contains a biological fluid that has been transiently separated from the body, can be considered an isolated composition according to the invention. The extracorporal composition can in various embodiments can comprise or consist of blood, urine or plasma (in addition to a compound provided by the invention).

In one embodiment, the invention provides for formation of a guest-host complex comprising a non-covalently associated complex of a compound of the invention and an NMBA. The guest-host complex can therefore be considered to be an organized chemical entity resulting from the association of two or more components of the NMBA and the host held together by non-covalent intermolecular forces. Without intending to be bound by theory, we believe we have shown in an animal model that the binding of this guest-host complex is very stable, such that reversal of drug effects is stable and the guest-host complex is eliminated in urine within 2-3 hours. This unique pharmacokinetic-pharmakodynamic constellation has important implications for clinical anesthesia, critical care medicine and emergency medicine where respiratory side effects of anesthetics and neuromuscular blocking agents need to be reversed in due time in order to restore breathing and cardiovascular function.

For use in the invention, the compositions described herein can be administered as pharmaceutical preparations. Thus, they can be provided in a variety of solutions of various compositions, and can be combined with one or more standard pharmaceutically acceptable carriers. Some examples of pharmaceutically acceptable carriers can be found in: Remington: The Science and Practice of Pharmacy (2005) 21st Edition, Philadelphia, Pa. Lippincott Williams & Wilkins.

Various methods known to those skilled in the art may be used to introduce the compositions of the invention to an individual. These methods include but are not limited to intravenous, intramuscular, intracranial, intrathecal, intradermal, subcutaneous, and oral routes. In one embodiment, the composition is administered intravenously. The composition can be provided as a liquid, a solution, or a solid, and may be provided in combination with any suitable delivery form or vehicle, examples of which include but are not limited to caplets, capsules, tablets, an inhalant or aerosol, etc. The dose of the composition to be used will necessarily be dependent upon the needs of the individual to whom the composition of the invention is to be administered. These factors include but are not necessarily limited to the weight, age, sex, medical history, muscular composition of the individual, and the degree of muscular activity and/or level of consciousness to be restored. In this regard, our data show high in-vitro binding affinity of compounds of the invention to NMBAs and anesthetics translates to higher speed of reversal for these drugs. In embodiments a composition comprising one or more compounds of this disclosure is administered in an amount effective to reduce the effects of the intoxicating agent. Those skilled in the art will be able to readily recognize a reduction in the effect of an intoxicating agent. In embodiments, the amount of a compound of this disclosure administered to an individual is from 0.1 mg/kg to 1000 mg/kg inclusive, and including all integers to the first decimal point there between. In embodiments the effective amount comprises a compound of this disclosure in mg/kg of 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, and all ranges there between. In embodiments, the effective amount comprises 10, 20, 30, 40, 50, 60, 70, 80, 90, 100, 110, 120, 130, 140, 150, 160, 170, 180, 190, 200, 210, 220, 230, 240 or 250 mg/kg. In non-limiting examples, the dosage is at least or is 100 mg/kg. In non-limiting examples, for an individual intoxicated by fentanyl, the effective amount is at least or is 100 mg/kg. In non-limiting examples, for an individual intoxicated by cocaine, the effective amount is between and 100 mg/kg to 200 mg/kg, inclusive. In a non-limiting example, for an individual intoxicated by methamphetamine, the effective amount is from 65 mg/kg to 130 mg/kg. An effective amount can be administered once in a single dose, or can be administered over time, and/or in successive dosages with differing, i.e., increasing or decreasing amounts of the compound such that the intoxication is reversed. The disclosure includes complete and partial reversal of intoxication.

To perform the present invention, a composition comprising a compound of the invention is administered to the individual as detailed above. The compounds used in the method are acyclic CB[n]-type compounds.

In embodiments, the disclosure comprises kits for prophylaxis and/or therapy for drug intoxication. The kits can comprise one or more compounds of this disclosure in, for example, a pharmaceutical formulation comprising a suitable buffer and pharmaceutically acceptable excipients, carriers and the like. The compositions can be included on or more sterile containers, such as vials, ampules, tubes, a bolus, etc. The kits may comprise, for example, a needle suitable for administration of a composition of this disclosure to individual, and a syringe, and/or other components for use in administration. The kits can comprise printed material, such as instructions, and/or an indication that the kit is for use in treating, treating an individual intoxicated with a drug of abuse, including but not necessarily limited to cocaine, fentanyl, methamphetamine, or a combination thereof.

In performing the present invention, we demonstrate formation of complexes of compounds of the invention and NMBAs and certain anesthetic agents and provide a characterization of certain reaction kinetics associated therewith as more fully described below. Further, we demonstrate that compounds of the invention are non-toxic to human cells. Further still, we tested an embodiment of the invention by administration of the commonly used NMBA rocuronium 3.5 mg/kg and cisatracurium 0.5 mg/kg to 10 anesthetized, tracheostomized, mechanically ventilated rats, which induced complete atonia of all skeletal muscles, resulting in long-lasting apnea. More specifically, for surgical procedures described in the Examples presented herein, rats were anesthetized (isoflurane 5% induction, 1,5% maintenance, in 70% $N_2O$/30% $O_2$) and tracheotomized. Spontaneous breathing was maintained during surgery and if possible according to normal protocol. Rats lay in the supine position with the head supported in a neutral position in the midline on a soft piece of tissue. The left femoral vein and artery were cannulated for drug infusion and blood sampling. Arterial blood gases and pH were measured every 10 or 30 minutes (Corning 178; Corning, N.Y., USA) and continuous measurement of blood pressure (PowerLab; ADInstruments, Colorado Springs, Mo.) and heart rate were performed. If mechanical ventilation was necessary animals were ventilated through a tracheostomy (SAR-830; CWE, Ardmore, Pa., USA). Rectal temperature was kept at 37.0±0.1° C. using a thermostatic heating pad (FHC, Bowdoinham, Me.). Level of anesthesia was maintained throughout the experiment to eliminate cardiovascular response to tail pinch. In all treatment groups, systemic physiological parameters were kept well within normal range. The right leg was shaved and the femoral nerve was stimulated supramaximally with subcutaneous needle electrodes, and the evoked response of the quadriceps femoris muscle was measured by accelerometry, with the TOF-Watch SX Monitor (Organon Ireland Ltd, a part of Schering-Plough Corporation, Dublin, Ireland), as described previously (Fassbender et al, Anesthesiology 2007). The transducer was fixed to the skin ventromedially at the proximal end of the thigh, next to the tibial tuberosity (insertion point of the patellar ligament).

After determination of the supramaximal stimulation current and calibration of the TOF-Watch (cal 1 mode), we stimulated the femoral nerve continuously at 1 Hz (10 mA±2 mA) for at least 10 minutes until twitch height reached a stable plateau. We then re-calibrated the TOF-Watch SX monitor, took a baseline train-of-four (TOF) at 2 Hz, and continued to stimulate the femoral nerve at 1 Hz with the single twitch mode until drugs were infused.

To obtain an estimate of the efficacy of rocuronium at the rat quadriceps femoris muscle and its reversibility by Motor1, all rats were anaesthetized with isoflurane 2-5 vol % during induction and surgery (inspiratory gas: 30% $O_2$ and 70% $N_2O$), and 1.5 vol % during measurement.

After pre-stimulation rats were paralyzed with rocuronium 3.5 mg kg$^{-1}$ (two times the ED90) as reported before (BJA 2008) and mechanically ventilated to achieve normocapnia confirmed by an arterial blood gas analysis. 30 s after onset of complete neuromuscular block we injected Motor1 (30 mg kg$^{-1}$, n=5, 60 mg kg$^{-1}$, n=5 or 90 mg kg$^{-1}$, n=5) or placebo (saline 0.5 ml, n=5). In ten more rats, following administration of cisatracurium 0.5 mg/g, we administered Motor1 15 mg, 30 mg, and 60 mg. Finally, in four more rats, we administered Motor2 following rocuronium and atracurium induced complete neuromuscular blockade.

Endpoints included time to recovery of spontaneous breathing, twitch height as well as TOF-ratio. Arterial pressure and heart rate were measured continuously, and arterial blood gas was measured directly before application of Motor1 and 30 minutes later. Arterial blood samples were collected at baseline, 2, 5, 10, 15, 20 and 60 minutes and subsequently processed for plasma samples which were stored at −80° C. until analyzed. At 60 min after the injection of Motor1 urine was collected and stored at −80° C. until analysis.

For the urine samples, we took 0.1 mL from each urine sample and dried them under high vacuum. Then they were dissolved in 0.5 mL $D_2O$, and 0.1 mL of 60 mM reference solution (1,3,5-tricarboxylate benzene) was added. NMR spectra were taken and the concentration of Motor1 in urine was calculated from the ratio between the integration of diagnostic peak for reference (8.3 ppm, 3H) and Motor1 (1.9-1.5 ppm, 12H).

We determined that Motor1 reversed rocuronium effectively, in a dose-dependent fashion. Normal breathing recovered after 720±s [placebo, i.e., 1 cc of normal saline), 120±15s, 15±5s, and 8±3 seconds after Motor1 10 mg, 20 mg, and 30 mg, respectively, were administered. The quadricepts femors twitch height was normalized after 960±s [placebo], 240±s, 120±s, and 60±s, respectively, after Motor1 10 mg, 20 mg, and 30 mg, respectively, were administered. Motor 1 did not have any side effects on arterial blood-gas analysis, EKG, arterial blood pressure, or heart rate. Additionally, we have analyzed blood and urine samples from all the tested rats and did not observe any allergic reactions or adverse effects on coagulation.

Following cisatracurium, normal breathing recovered after 750(17)s(+/−s shown in parenthesis) [placebo, normal saline], 28 (6)s, and 11(4) seconds (means(SD) after 30 mg, and 60 mg Motor1, respectively. The quadirecps femors twitch height was normalized after 1002 (122) s [placebo, normal saline], 266 (17)s, 130 (14) s, and 68 (10)s, respectively. Motor1 and 2 did not have any side effects on: arterial blood-gas analysis, EKG, arterial blood pressure, and heart rate. We have taken blood and urine samples from all rats and observed that Motor 1 is eliminated via urine. We did not observe any evidence of allergic actions and/or adverse effects on coagulation.

To evaluate the effectiveness to reverse ketamine, anesthesia was induced with 3% isoflurane, and maintained for surgical instrumentation with 1.5% isoflurane. We cannulated the femoral vein (times 2) for subsequent ketamine infusion and reversal agent injection), cannulated the artery for invasive blood pressure measurement, transected the trachea, and cannulated it with PE240 tubing through which the rat spontaneously breathed. Rats lay in the supine position with the head supported in a neutral position in the midline on a soft piece of tissue. A temperature probe was inserted into the rectum and core temperature was regulated at 37+/−1 degree Celsius using a heating pad. Two screw electrodes (Plastics One Inc., Roanoke, Va.) were inserted into holes drilled into the skull, one approximately 1.0 mm anterior and one approximately 3 mm posterior to the bregma and approximately 1 mm lateral to the midline. The free ends of the leads were connected to an amplifier and EEG activity was filtered by a low-pass (100 Hz) filter. We also measured EKG, and videotaped the rat in order to evaluate respiratory rate, and movements. In two rats, traheostomy was not performed as to be able to evaluate noise indicating recovery from anesthesia After surgery, we discontinued isoflurane and started an infusion of either ketamine (1500 µg/kg/min). Motor2 200 mg was administered 60 minutes after discontinuation of isoflurane under steady state ketamine anesthesia while ketamine infusion was still running at a constant rate. We observed that Motor2 reverses ketamine anesthesia: increase in heart rate, blood pressure and respiratory rate to pre-anesthesia values, movements, spontaneous urination, and distress calls.

The following provides a characterization of the compounds used to reverse the effects of NMBAs and anesthetics according to the method of the invention. The terms Motor 1 and Motor 1 as used herein are interchangeable. The terms Motor2 and Motor 2 and used herein are also interchangeable.

As used herein, "alkyl group" refers to branched or unbranched hydrocarbons. Examples of such alkyl groups include methyl groups, ethyl groups, butyl groups, nonyl groups, neopentyl groups, and the like. For example, the alkyl group can be a $C_1$ to $C_{20}$ alkyl group, including all integer numbers of carbons and ranges of numbers of carbons therebetween.

As used herein, "carbocyclic group" refers to a cyclic compound having a ring or multiple rings in which all of the atoms forming the ring(s) are carbon atoms. The rings of the carbocyclic group can be aromatic or nonaromatic, and include compounds that are saturated and partially unsaturated, and fully unsaturated. Examples of such groups include benzene, naphthalene, 1,2-dihydronaphthalene, cyclohexane, cyclopentene, and the like. For example, the carbocyclic group can be a $C_3$ to $C_{20}$ carbocyclic group, including all integer numbers of carbons and ranges of numbers of carbons therebetween.

As used herein, "heterocyclic group" refers to a cyclic compound having a ring or multiple rings where at least one of the atoms forming the ring(s) is a heteroatom (e.g., oxygen, nitrogen, sulfur, etc.). The rings of the heterocyclic group can be aromatic or nonaromatic, and include compounds that are saturated, partially unsaturated, and fully unsaturated. Examples of such groups include imidazolidin-2-one, pyridine, quinoline, decahydroquinoline, tetrahydrofuran, pyrrolidine, pyrrolidone, and the like. For example, the heterocyclic group can be a $C_1$ to $C_{20}$ heterocyclic group, including all integer numbers of carbons and ranges of numbers of carbons therebetween.

As used herein, "carbocyclic ring system" refers to a cyclic compound having a ring or multiple rings in which all of the atoms forming the ring(s) are carbon atoms. Examples of such groups include benzene, naphthalene, 1,2-dihydronaphthalene, cyclohexane, cyclopentene, and the like. The rings of the carbocyclic ring system or heterocyclic ring system can be aromatic or nonaromatic, and include compounds that are saturated, partially unsaturated, and fully unsaturated. For example, the carbocyclic ring system can be a $C_3$ to $C_{20}$ carbocyclic group, including all integer numbers of carbons and ranges of numbers of carbons therebetween. In another example, the carbocyclic ring system can be a phenyl group or naphthyl group. The phenyl group or naphthyl group is attached to the compound via adjacent carbons of the phenyl group or naphthyl group.

As used herein, "heterocyclic ring system" refers to a cyclic compound having a ring or multiple rings in which at least one of the atoms forming the ring(s) is a heteroatom (e.g., oxygen, nitrogen, sulfur, etc.). The rings of the carbocyclic ring system or heterocyclic ring system can be aromatic or nonaromatic, and include compounds that are saturated, and fully unsaturated. Examples of the heterocyclic ring system include imidazolidin-2-one, pyridine, quinoline, decahydroquinoline, tetrahydrofuran, pyrrolidine, pyrrolidone, and the like. For example, the heterocyclic ring system can be a $C_1$ to $C_{20}$ heterocyclic group, including all integer numbers of carbons and ranges of numbers of carbons therebetween.

Any of these groups and/or rings may each be substituted with alkyl groups and other substituents such as, for example, nitro, cyano, keto, carboxy, alkoxy, hydroxyl, amine, amide, halide (e.g., bromide, chloride, fluoride, and iodide), and alkoxy groups. For example, the alkyl groups or aryl groups may be further substituted. For example, the alkyl group can be halide substituted (e.g., a 2-chloroethyl group). As another example, a carbocyclic group can be cyano substituted (e.g., 3-cyano naphthalene).

In an aspect, the present invention provides acyclic CB[n]-type compounds having the following structure:

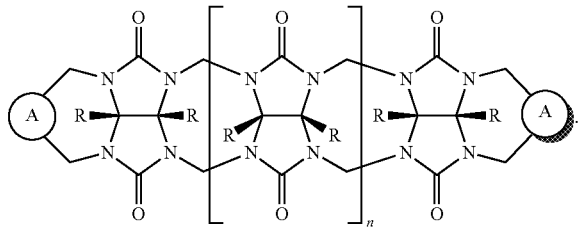

Each R is independently hydrogen, $C_1$ to $C_{20}$ alkyl group, $C_3$ to $C_{20}$ carbocyclic group, $C_1$ to $C_{20}$ heterocyclic group, carboxylic acid group, ester group, amide group, hydroxyl, or ether group. The carboxylic acid, ester, amide, and ether groups can have from 1 to 20 carbons, including all integer values and ranges therebetween. Optionally, adjacent R groups form a $C_3$ to $C_{20}$ carbocyclic ring or heterocyclic ring, where the carbocyclic ring is a ring in which all of the atoms forming the ring(s) are carbon atoms and the heterocyclic ring is a ring where at least one of the atoms forming the ring(s) is a heteroatom (e.g., oxygen, nitrogen, sulfur, etc.). These rings may each be substituted with alkyl groups and other substituents such as, for example, nitro, cyano, keto, carboxy, alkoxy, hydroxyl, amine, amide, halide (e.g., bromide, chloride, fluoride, and iodide), and alkoxy groups.

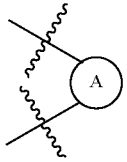

Each is independently a $C_5$ to $C_{20}$ carbocyclic ring system or $C_2$ to $C_{20}$ heterocyclic ring system. At least one

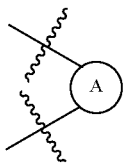

of the compound has at least one solubilizing group. In an embodiment, both

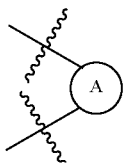

s of the compound have at least one solubilizing group. In an embodiment, one

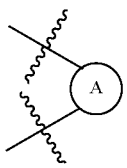

of the compound has at least one solubilizing group. In various embodiments, the ring system has 1, 2, 3, 4, 5, or 6 solubilizing groups. Optionally, the ring system has a targeting group. The value of n is 1 to 5, including all integer values therebetween. In an embodiment, the

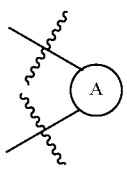

groups are the same.

In various embodiments, the compound is a salt, a partial salt, a hydrate, a polymorph, a stereoisomer or a mixture thereof. The compounds can have stereoisomers. For example, the compound can be present as a racemic mixture, a single enantiomer, a single diastereomer, mixture of enantiomers, or mixture of diastereomers.

Without intending to be bound by any particular theory, it is considered that the solubilizing group (or groups) increase (or impart) solubility of compounds in water or aqueous solvent systems. The solubilizing group can be a functional group that can be deprotonated over a broad pH range. The solubilizing group can have a cationic (e.g., ammonium and sulfonium groups), anionic (e.g., sulfate, sulfonate, phosphate, and phosphonate groups) or neutral group (e.g., sulfonic acids, phosphonic acids, polyethylene glycol (PEG) ethers (including PEG ether oligomers), crown ethers, and cyclam groups). Another example of a neutral solubilizing group is a zwitterionic group (e.g., a group with both an ammonium group and a sulfonate group), where both ionic groups are covalently bonded to the compound. It is desirable that cationic solubilizing groups not interact with cavity of the compound. The compound can have mixtures of solubilizing groups. In an embodiment, the solubilizing group selected from sulfonic acid, sulfonate salt, phosphonic acid, phosphonate salt, and polyethylene glycol. The solubilizing group can be connected to the linking group though a heteroatom, such as oxygen or sulfur. For example, the PEG group can be connected to the compound through a sulfur atom forming a thioether moiety. For example, the polyethylene glycol group can have a molecular weight of from 107 to 100,000, including all integer values and ranges therebetween.

In one embodiment, the solubilizing group or groups are not carboxylic acids or carboxylic acid salts. In one embodiment, at least one of the solubilizing groups is not a carboxylic acid or carboxylic acid salt.

The targeting group is a moiety that interacts with, for example, a cell. A targeting group (TG) is a moiety that targets, for example, tumor cells by either passive or active targeting by methods known in the art. Examples of targeting groups include dendrons, dendrimers, PEG groups, peptides, polypeptides, folates, amidines, antibodies, proteins, steroids, mono or oligosaccharides, and the like.

In an embodiment, each

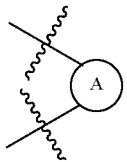

of the compound is independently a $C_5$ to $C_{20}$ carbocyclic ring system having one of the following structures:

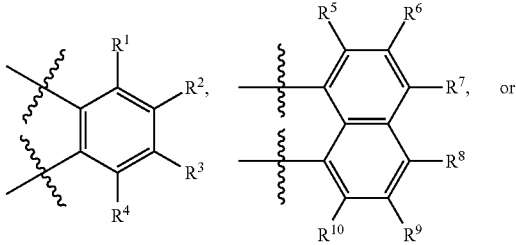

-continued

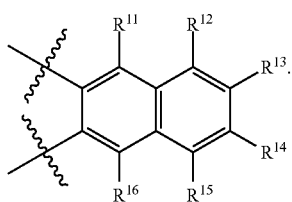

At each occurrence of

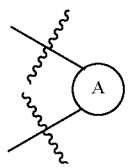

$R^1$ to $R^{16}$ is independently hydrogen, $C_1$ to $C_{20}$ alkyl group, halo group, hydroxyl group, nitro group, carboxylic acid group, ester group, amide group, ether group, $C_3$ to $C_{20}$ carbocyclic group, or $C_1$ to $C_{20}$ heterocyclic group. For example, the carboxylic acid group, ester group, amide group, and ether groups can have from 1 to 20 carbons, including all integer values and ranges therebetween. At least one of $R^1$ to $R^{16}$ in the compound has the following structure:

LG is a linking group and X is the solubilizing group. Optionally, one or more adjacent $R^1$ to $R^{16}$ groups are connected forming a carbocyclic or heterocyclic ring, and the ring can be substituted or unsubstituted.

As used herein, "adjacent" refers to groups attached through 2 or 3 carbons as depicted by, for example,

● in the structures:

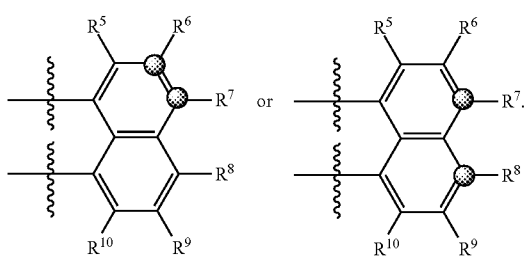

It is contemplated that groups can be attached through any two adjacent carbons.

A linking group (LG) is a group that connects with a solubilizing group (X) or a targeting group (TG). The linking group can be, for example, an alkoxy moiety or an alkyl moiety. The linking group can have independently at each occurrence a thioether linkage, ether linkage, amino linkage, amide linkage, ester linkage, triazole ring linkage, or a combination thereof. For example, these linkages can join the linking group and solubilizing group or targeting group. In an embodiment, the linking group, LG, is a 1-substituted triazole.

In an embodiment,

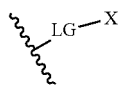

has the following structure:

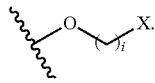

The value of each i is independently 1 to 20, including all integer values therebetween.

In an embodiment, at least one of the $R^1$ to $R^{16}$ groups in the compound has the following structure:

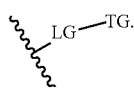

LG is a linking group and TG is a targeting group.

In an embodiment, the compound has one of the following structures:

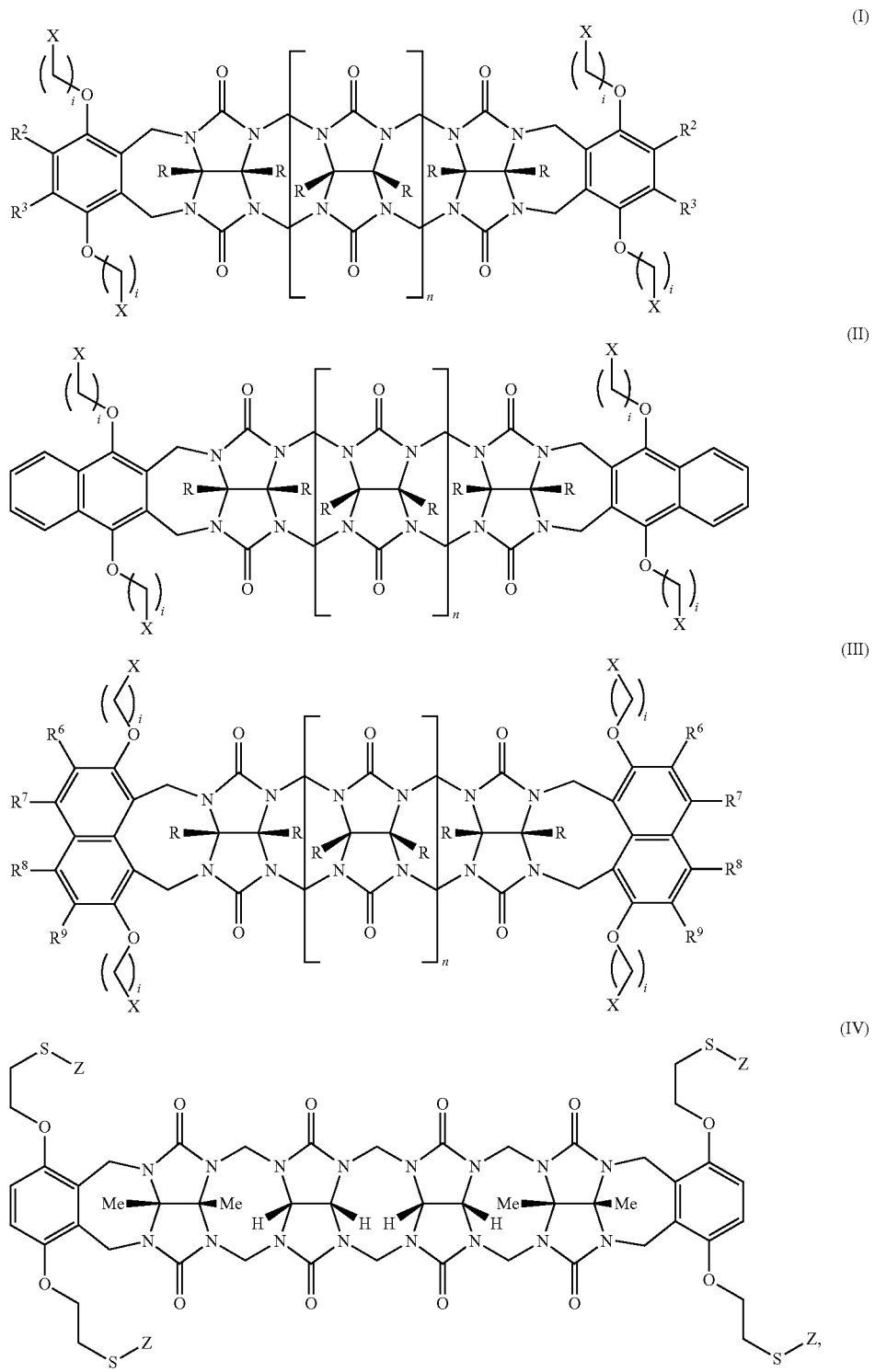

wherein Z is PEG group. In an embodiment, the PEG group has a molecular weight of 200 to 10,000, including all integers and ranges therebetween. In an embodiment, the PEG group has a molecular weight of 350 (PEG350), 750 (PEG750), 1900 (PEG1900), or 5000 (PEG5000).

Compounds having the structures of formulae I-IV can be prepared, for example, by the synthetic methodology described in Examples 1-2. In this embodiment, R, $R^2$, $R^3$, $R^6$, $R^7$, $R^8$ and $R^9$ are as defined herein.

In various embodiments, the compounds have the following structures:
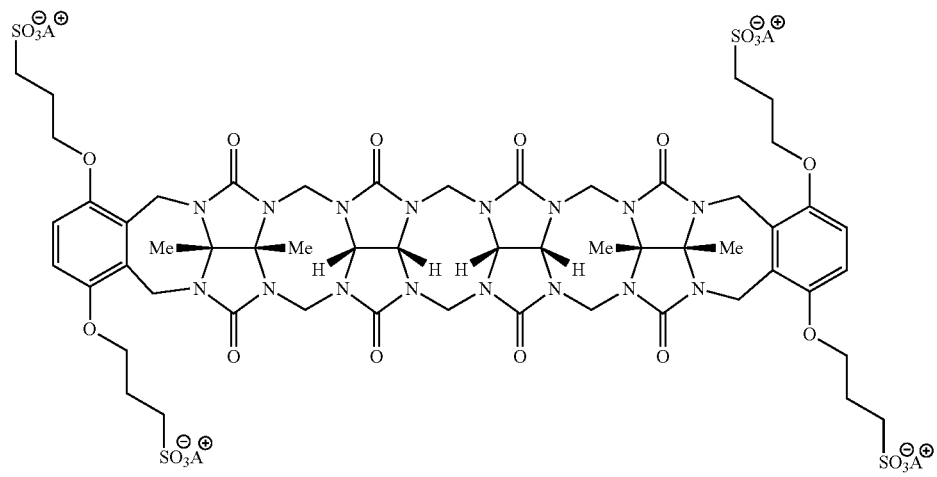
(referred to herein as Motor1),
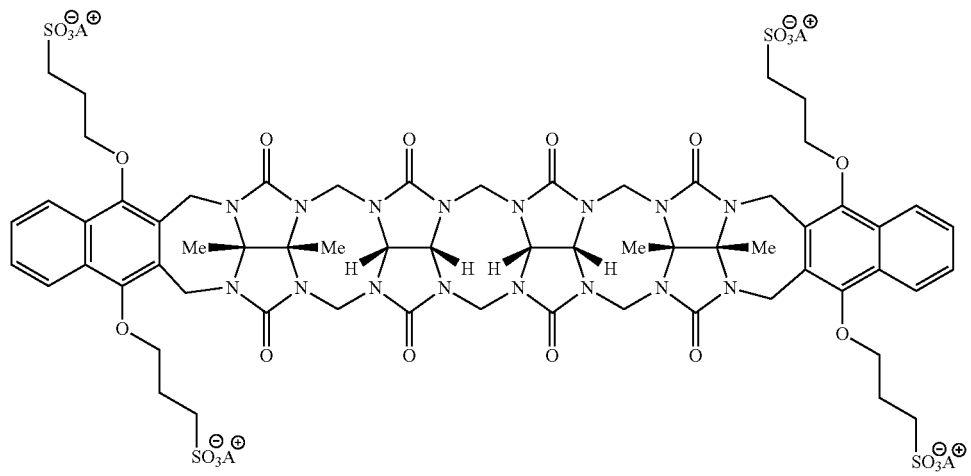
(referred to herein as Motor2),
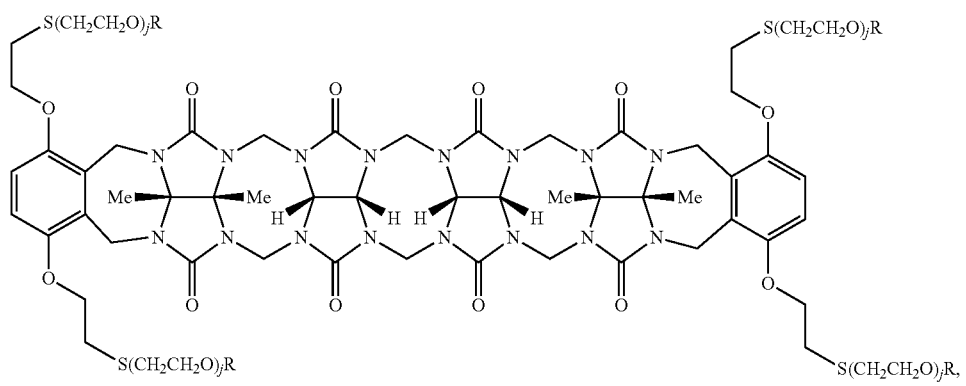

where j is, for example, 1 to 2250, including all integer values and ranges therebetween, and R in this example is hydrogen or an alkyl group,
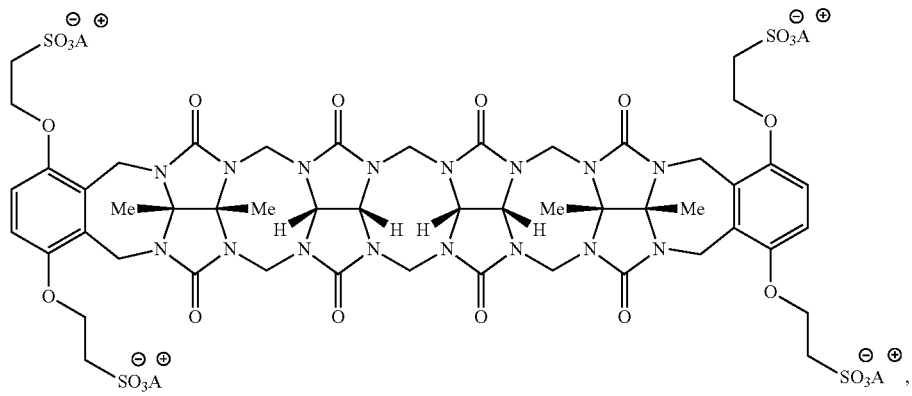
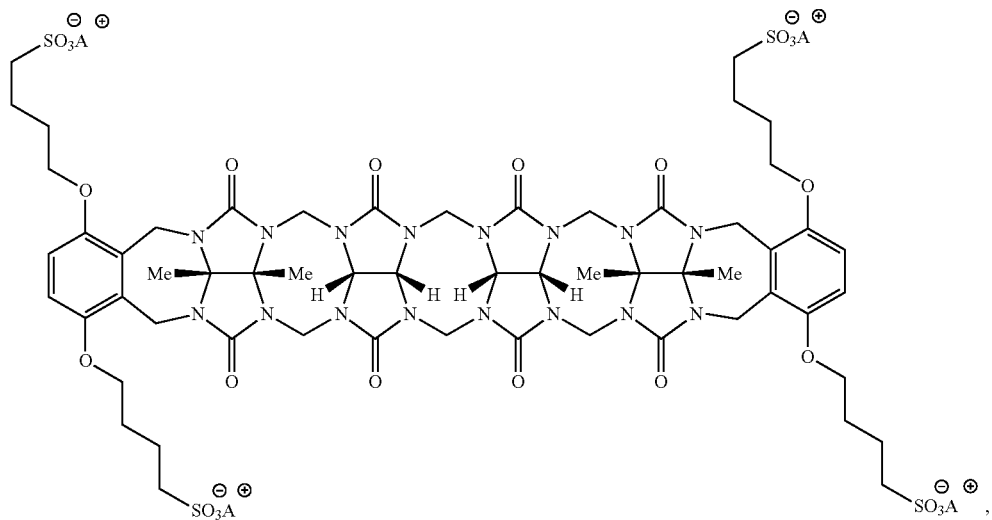
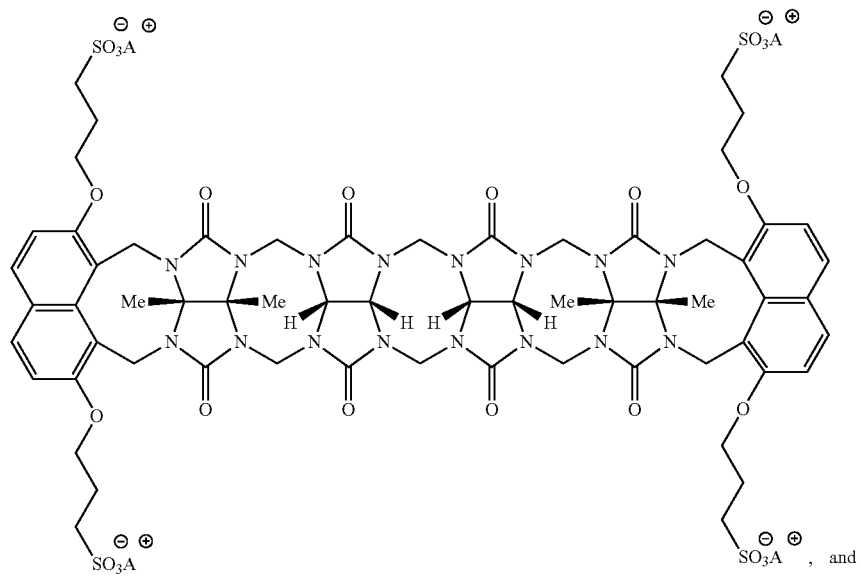
, and -continued

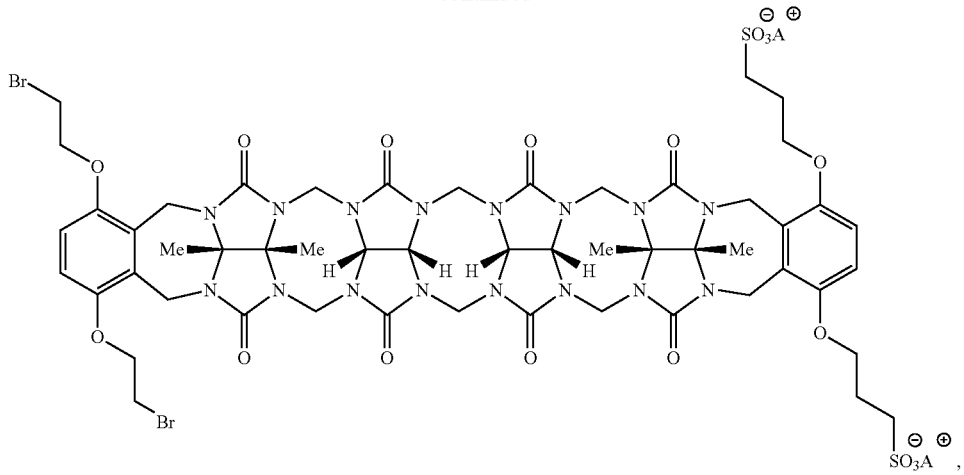

where $A^+$ can be $H^+$, $Na^+$, $K^+$, $Ca^{2+}$, $Mg^{2+}$, $Zn^{2+}$, $H_4N^+$, $Et_3NH^+$, $Me_4N^+$, $(HOCH_2CH_2)_3NH^+$, or a cationic form of ethylenediamine, piperazine, and trishydroxymethyl aminomethane (TRIS).

An example of a general method for the preparation of the compounds of the present invention is provided in the following. The method comprises the following steps:

1) Providing a compound (1) of the following structure:

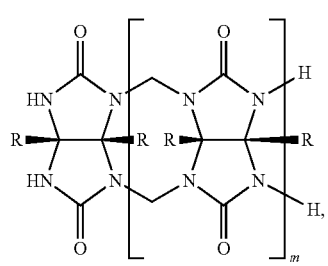

(1)

where m is from 0 to 4,

2) Forming a reaction mixture comprising compound (1), an acid (e.g., $MeSO_3H$, HCl, $CF_3CO_2H$, $H_2SO_4$, or TsOH) and a compound (2) having the following structure:

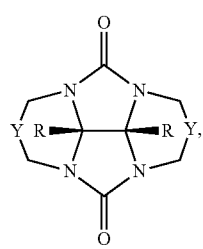

(2)

where each R is independently hydrogen, $C_1$ to $C_{20}$ alkyl group, $C_3$ to $C_{20}$ carbocyclic group, $C_1$ to $C_{20}$ heterocyclic group, carboxylic acid group, ester group, amide group, hydroxyl group or ether group. Optionally, adjacent R groups form a $C_3$ to $C_{20}$ carbocyclic ring or heterocyclic ring, where the carbocyclic ring is a ring in which all of the atoms forming the ring(s) are carbon atoms and the heterocyclic ring is a ring where at least one of the atoms forming the ring(s) is a heteroatom (e.g., oxygen, nitrogen, sulfur, etc.). These rings may each be substituted with alkyl groups and other substituents such as, for example, nitro, cyano, keto, carboxy, alkoxy, hydroxyl, amine, amide, halide (e.g., bromide, chloride, fluoride, and iodide), and alkoxy groups. Y is oxygen or nitrogen substituted with a $C_1$ to $C_{20}$ alkyl group. (2) is added to the reaction mixture such that a compound (3), of the following structure is formed:

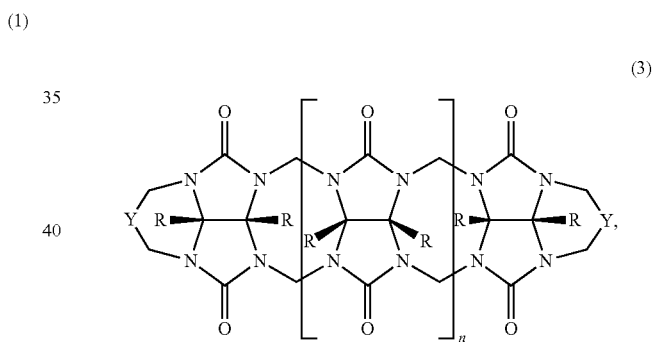

(3)

3) Contacting said compound (3) with TFA and

which can be a $C_5$ to $C_{20}$ carbocyclic ring system or $C_2$ to $C_{20}$ heterocyclic ring system, where the ring system comprises one or more rings. The ring system, optionally, has at least one solubilizing group.

Optionally, the ring system has a targeting group. Compound (3), a solvent, and (A)

are combined such that the following structure is formed:

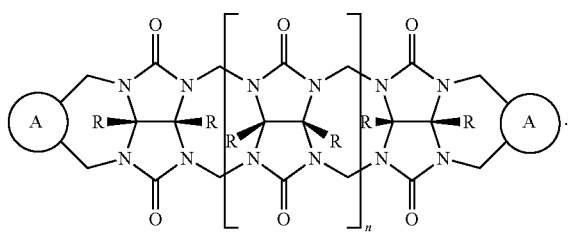

In an embodiment,

can be derivatized with the solubilizing group and/or targeting group after step 3). For example, one of the building block compounds can be derivatized to form a compound of the present invention. For example, an alkyl bromide component of one of the building block compounds can be reacted with a PEGylated thiol to make a compound with a PEG solubilizing group.

Examples of

include but are not limited to:

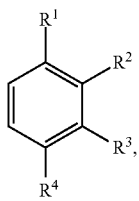 (4)

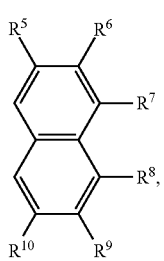 and (5)

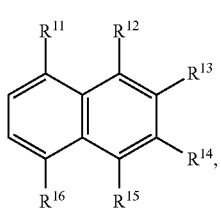 (6)

where each $R^1$ to $R^{16}$ is independently hydrogen, $C_1$ to $C_{20}$ alkyl group, halo group, hydroxyl group, nitro group, carboxylic acid group, ester group, amide group, ether group, $C_3$ to $C_{20}$ carbocyclic group, or $C_1$ to $C_{20}$ heterocyclic group. For example, the carboxylic acid group, ester group, amide group, and ether groups can have from 1 to 20 carbons, including all integer values and ranges therebetween. At least one of the $R^1$ to $R^{16}$ groups in the structure has the following structure:

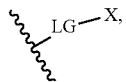

where LG is the linking group and wherein X is the solubilizing group. In an embodiment, LG can have the formula:

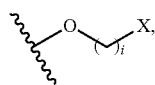

where each i is 1 to 20. Optionally one or more adjacent $R^1$ to $R^{16}$ groups are connected forming a carbocyclic or heterocyclic ring, and the ring can be substituted or unsubstituted. In an embodiment, at least one of the $R^1$ to $R^{16}$ groups in the structure has the following structure:

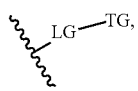

where LG is a linking group and wherein TG is the targeting group.

It is desirable for the

group to be reactive in electrophilic aromatic substitution reactions. Thus, in an embodiment, the

group is an aromatic ring having at least one alkyl ether moiety.

The determination of suitable reaction conditions (e.g., solvent, reaction time and reaction temperature) is within the purview of one having skill in the art. A wide range of solvent can be used. Examples of suitable solvents include TFA, HCl, $H_2SO_4$, TsOH, HBr, $MeSO_3H$, and mixtures thereof. For example, it may be desirable to add acetic anhydride as a co-solvent. Reaction time can vary. Generally, a reaction time of 3 hours is sufficient to provide a desired extent of reaction. A wide range of reaction temperatures can be used. For example, reaction temperatures of 25° C. to 100° C. can be used.

In an embodiment, the compounds can be made from building block compounds (i.e., intermediates). The building block compounds have functional groups (e.g., halogen (e.g., fluoro, chloro, bromo, or iodo), hydroxy, carboxylic acid, alkenyl, alkynyl, nitro, cyano, keto, amino, amido, thioether, thioate and triazole groups) that can be reacted to form solubilizing groups or targeting groups. Examples of building block compounds include:

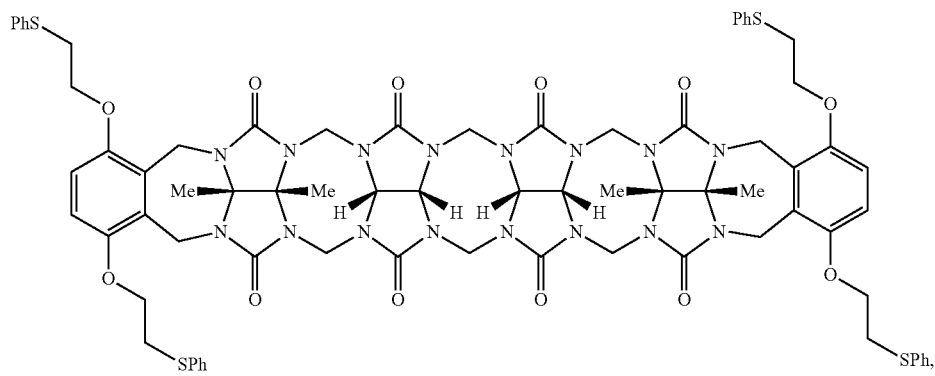
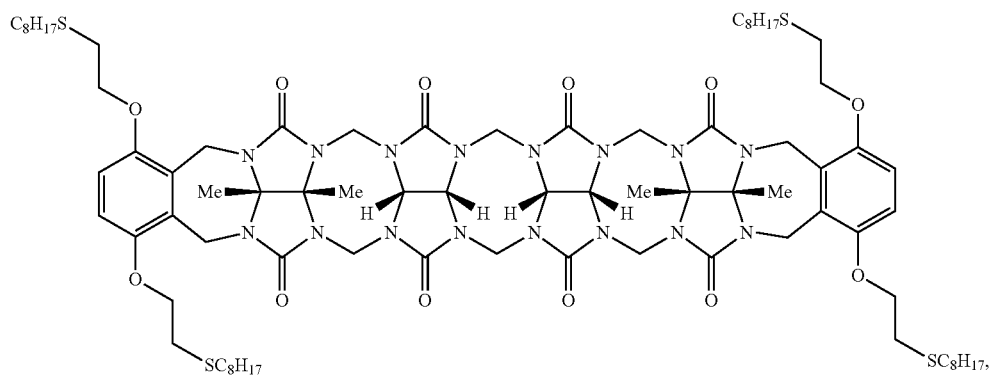
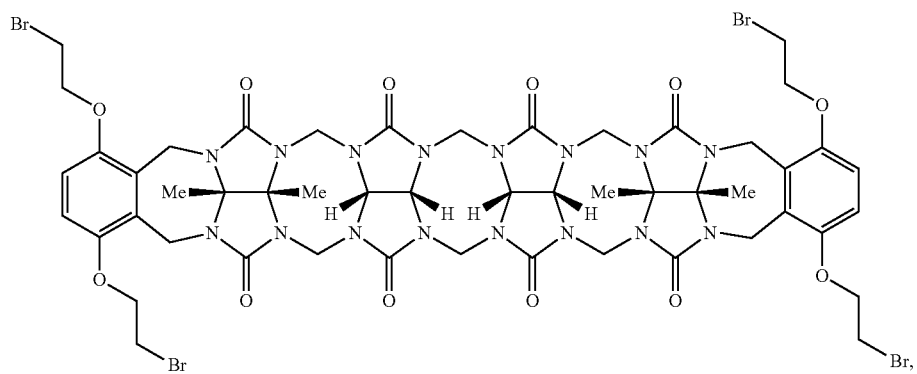
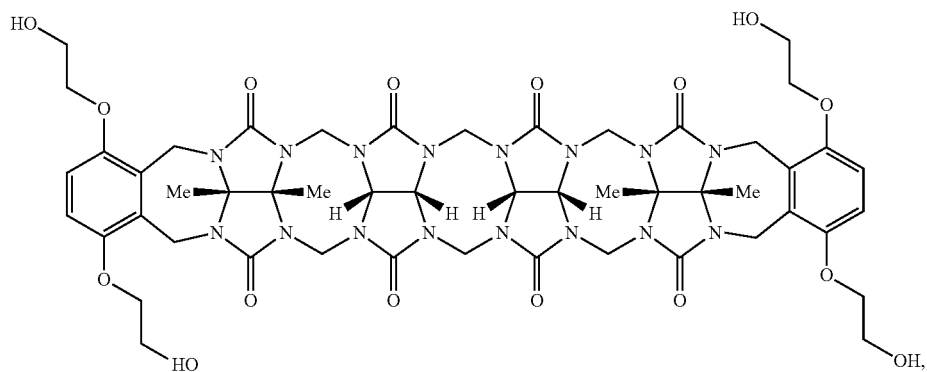

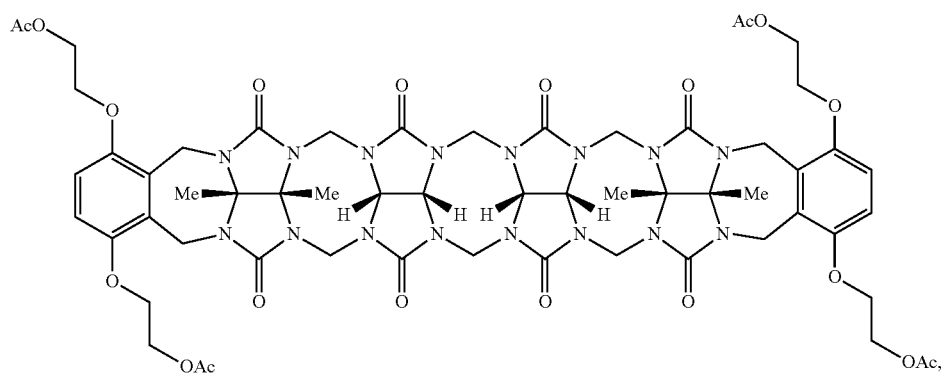
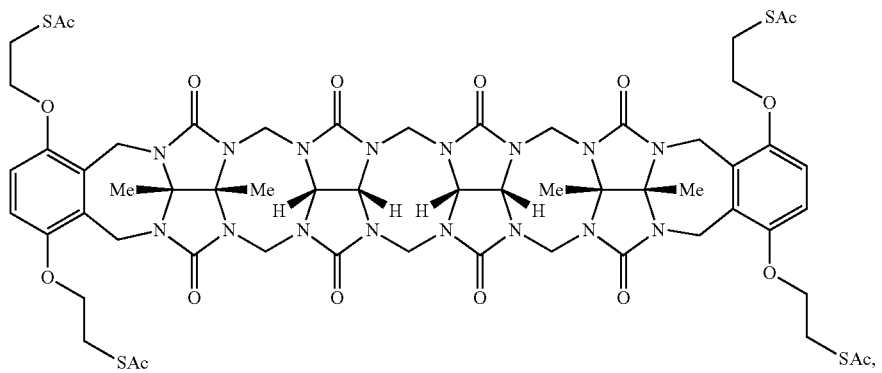
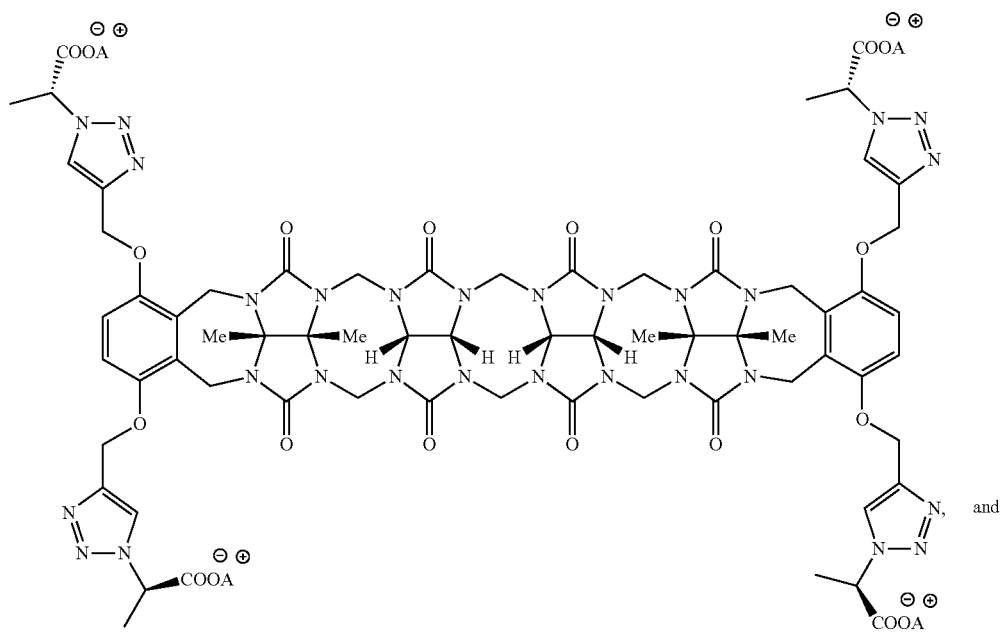

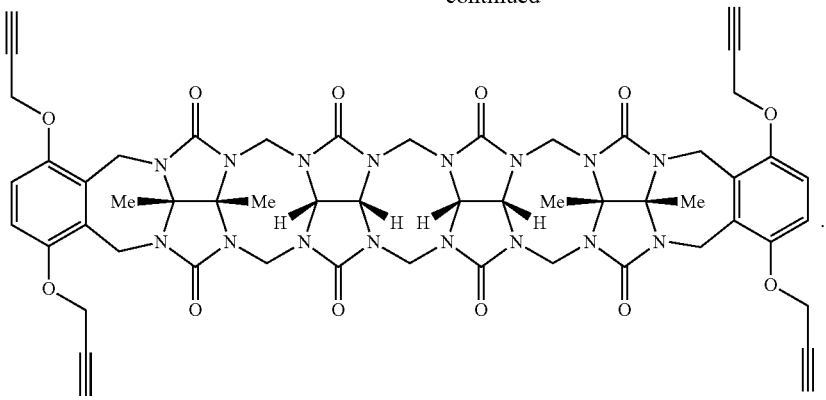

For example, the tetra propargyl compound can be reacted with azides to form for example a triazole compound.

The following examples are presented to illustrate the present invention. They are not intended to be limiting in any manner.

EXAMPLE 1

General Experimental.

Starting materials were purchased from commercial suppliers and were used without further purification or were prepared by literature procedures. Melting points were measured on a Meltemp apparatus in open capillary tubes and are uncorrected. IR spectra were recorded on a JASCO FT/IR 4100 spectrometer and are reported in cm$^{-1}$. NMR spectra were measured on Bruker DRX-400 instrument operating at 400 MHz for $^1$H and 100 MHz for $^{13}$C. Mass spectrometry was performed using a JEOL AccuTOF electrospray instrument (ESI). UV-Vis absorbance was measured on Varian Cary 100 UV spectrophotometer.

Synthetic Procedures and Characterization. Glycoluril Dimer.

A mixture of glycoluril (500 g, 3.51 mol) and paraformaldehyde (105 g, 3.51 mol) in HCl (8 M, 70 mL) was heated at 50° C. for 48 h. The reaction mixture was cooled and filtered. The solid was washed with water (500 mL) and then recrystallized with TFA (1.5 L) to yield Glycoluril Dimer as a white solid (334 g, 62%).

Dimethyl Glycoluril.

Into a solution of urea (1140 g, 19.0 mol) in HCl (0.3 M, 2.8 L), 2, 3-butanedione (500 g, 5.8 mol) was added. The solution was stirred at RT for 12 h. The reaction mixture was filtered and the solid was washed with water (2.0 L×2) and then ethanol (2.0 L) to yield Dimethyl glycoluril as a white solid (749 g, 76%).

Dimethyl Glycoluril Bis(Cyclic Ether).

A mixture of Dimethyl glycoluril (749 g, 4.4 mol) and paraformaldehyde (650 g, 21.7 mol) in HCl (9 M, 3.8 L) was stirred for 24 h. Water (14.0 L) was added and the mixture was stirred for an additional 12 h. The mixture was then filtered and washed with water (2 L) and ethanol (2 L) to yield Dimethyl glycoluril bis(cyclic ether) as a white solid (719 g, 65%).

Figure 1:
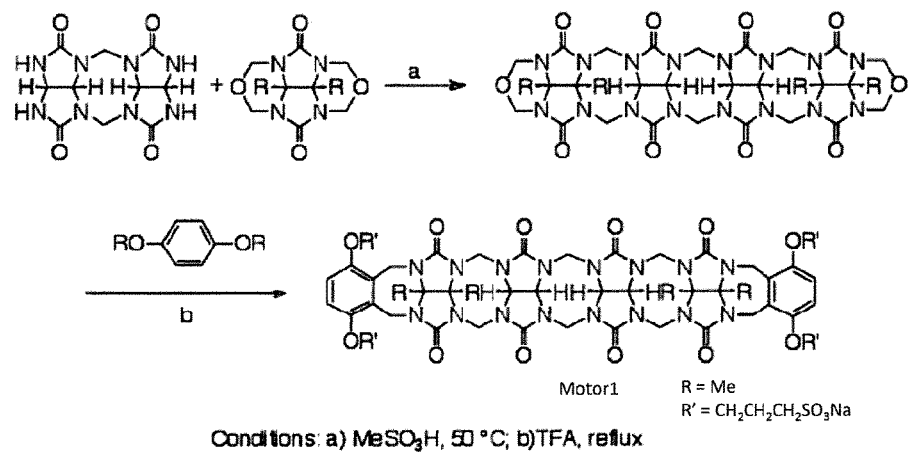
FIG. 1. Example of a Synthesis of Motor1
FIG. 2. Example of a Synthesis of Motor2
FIG. 3. Example of a Synthesis of Propargyl Host
FIG. 4. Example of a Synthesis of Ethanesulfonate Wall
FIG. 5. Example of a Synthesis of Butanesulfonate Wall
FIG. 6. Example of a Synthesis of 2,7-naphthalene sulfonate Wall
FIG. 7. Example of a Syntheses of Ethanesulfonate Host and Butanesulfonate Host
FIG. 8. Example of a Synthesis Napthalene Propanesulfonate Host
FIG. 9. Example of a Synthesis of Tetrabromo Host
FIG. 10. Example of a Synthesis of Tetrathiophenyl Host
FIG. 11. Example of a Synthesis of Tetraoctanethioether Host
FIG. 12. Example of a Syntheses of PEG350, PEG750, PEG1900, PEG5000 Hosts
FIG. 13. Example of a Synthesis of Dibromo Dipropanesulfonate Host
FIG. 14. Example of a Synthesis of Tetraester Host
FIG. 15. Example of a Synthesis of Tetrahydroxy Host
FIG. 16. Example of a Synthesis of Tetrathioacetate Host
FIG. 17. Example of a Synthesis of Tetratriazole Host
FIG. 18. An example of a Job plot of Motor1 and Rocuronium bromide (total concentration 10 mM, 20 mM $NaH_2PO_4$ buffer, pH 7.4): (A) Stack plot of $^1H$ NMR spectra; (B) Job plot of Rocuronium bromide (constructed using the chemical shift of the acetate singlet).

Methyl Tetramer. (FIG. 1)

Into a solution of Glycoluril Dimer (84 g, 0.27 mol) in anhydrous MeSO$_3$H (600 mL), Dimethyl glycoluril bis (cyclic ether) (304 g, 1.20 mol) was added. The mixture was stirred and heated at 50° C. for 3 h. The reaction mixture was poured into water (6.0 L). After filtration, the crude solid was dried in high vacuum. The crude solid was recrystallized from TFA (350 mL) and water (1.4 L) to yield Methyl tetramer as a white solid (76 g, 36%).

Propanesulfonate Wall.

Into a solution of hydroquinone (100 g, 0.91 mol) in aqueous NaOH solution (2.5 M, 1.4 L), a solution of propanesultone (275 g, 2.25 mol) in 1, 4-dioxane (1.8 L) was added. The mixture was stirred at RT for 12 h. The mixture was filtered. The solid was washed with acetone (2 L×2) to yield 3,3'-(1,4-phenylenebis (oxy))bis(propane-1-sulfonic acid) as white solid (294 g, 81%).

Motor1. (FIG. 1)

Into a solution of methyl tetramer (76 g, 97 mmol) in TFA (700 mL), propanesulfonate wall (154 g, 387 mmol) was added. The mixture was stirred and heated at 70° C. for 3 h. The solvent was removed by rotary evaporation and the solid was dried in high vacuum. The solid was washed with the mixture of water and acetone (1:2, v/v, 1.5 L×2). The solid was dissolved in water (500 mL) and adjusted to pH=7 by adding 1 M aqueous NaOH. The solvent was removed with rotary evaporation and then the solid was further dried under high vacuum to yield Motor1 as a white solid (60 g, 40%). M.p.>320° C. (decomposed). IR (ATR, cm-1): 3000 w, 1711 s, 1456 s, 1313 m, 1225 s, 1178 s, 1076 s, 972 m, 920 m, 822 m, 797 s, 756 m, 665 m. $^1$H NMR (400 MHz, D$_2$O): 6.72 (s, 4H), 5.50 (d, J=15.2, 2H), 5.38 (d, J=15.7, 4H), 5.31 (d, J=9.0, 2H), 5.25 (d, J=8.9, 2H), 5.19 (d, J=16.2, 4H), 4.10 (d, J=11.1, 4H), 4.06 (d, J=11.7, 4H), 3.97 (d, J=15.4, 2H), 3.91 (m, 4H), 3.79 (m, 4H), 2.98 (m, 8H), 2.06 (m, 8H), 1.64 (m, 6H), 1.61 (s, 6H). $^{13}$C NMR (100 MHz, D$_2$O, 1, 4-dioxane as internal reference): δ157.5, 157.3, 150.8, 128.3, 115.3, 79.7, 78.6, 72.3, 72.1, 69.2, 53.8, 49.4, 49.0, 35.9, 25.5, 17.1, 16.0. MS (ESI): m/z 1473.3232 ([M−H]$^-$), calculated 1473.3216.

Figure 2:
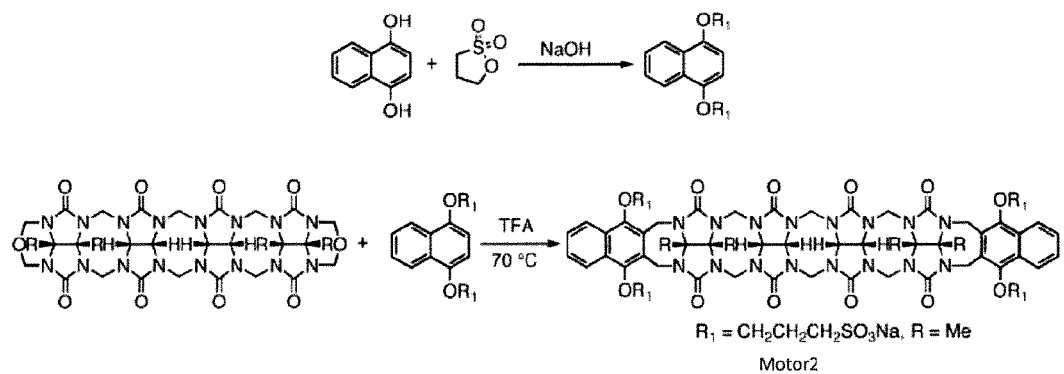

1,4-Naphthalene propanesulfonate Wall (FIG. 2).

Into a solution of 1,4-dihydroxynaphathelene (2.0 g, 12.5 mmol) in NaOH (10 wt %, 16 mL), a solution of propanesultone (3.8 g, 31.2 mmol) in 1,4-dioxane (24 mL) was added. This solution was stirred at RT for 12 h. After filtration, the solid was dissolved in H2O (10 mL) and then precipitated with MeCN (60 mL) to yield a blue solid (1.5 g, 3.3 mmol, 27%). M.p.>227° C. (dec.). IR (ATR, cm$^{-1}$): 2988 w, 2902 w, 1597 w, 1462 w, 1377 w, 1273 m, 1240 m, 1222 m, 1183 s, 1155 m, 1100 m, 946 s, 800 w, 765 m, 613 m. $^1$H NMR (600 MHz, D2O): 8.01 (m, 2H), 7.43 (m, 2H), 6.63 (s, 2H), 4.02 (t, 4H), 3.02 (t, 4H), 2.16 (m, 4H). $^{13}$C NMR (125 MHz, D$_2$O, 1,4-dioxane as internal reference):

δ148.0, 126.4, 125.9, 121.4, 106.3, 67.5, 48.1, 24.2. High-Res MS (ESI): m/z 427.0528 ([M+Na]$^+$), calculated 427.0497.

Motor2 (FIG. 2).

To a solution of methyl tetramer (2.67 g, 3.42 mmol) in TFA (25 mL), 1,4-Naphthalene propanesulfonate wall (6.13 g, 13.7 mmol) was added. This solution was stirred and heated at 70° C. for 3 h. The solvent was removed with rotary evaporation and the solid was dried in high vacuum. The crude mixture was refluxed in EtOH (60 mL) overnight and then filtered. The solid was dissolved in hot water (20 mL). The solution was adjusted to pH=7 with 1 M NaOH. The solution was cooled down to RT and filtered to yield Motor2 as a white solid (1.7 g, 30%). M.p.>196° C. (decomposed). IR (ATR, cm$^{-1}$): 3433 w, 1717 s, 1471 s, 1425 m, 1383 m, 1349 m, 1317 m, 1179 s, 1082 s, 1036 s, 922 w, 881 w, 827 m, 801 s, 757 m, 728 m, 676 m. $^1$H NMR (600 MHz, D$_2$O): 7.72 (m, 4H), 7.27 (m, 4H), 5.48 (d, J=15.3, 2H), 5.42 (d, J=15.7, 4H), 5.31 (d, J=8.9, 2H), 5.25 (d, J=8.9, 2H), 5.12 (d, J=16.0, 4H), 4.30 (d, J=16.0, 4H), 4.12 (d, J=15.7, 4H), 4.00 (m, 4H), 3.96 (d, J=15.3, 2H), 3.74 (m, 4H), 3.08 (m, 8H), 2.13 (m, 8H), 1.66 (s, 6H), 1.61 (s, 6H). $^{13}$C NMR (125 MHz, D$_2$O, 1, 4-dioxane as internal reference): δ156.7, 156.3, 148.2, 127.7, 127.0, 126.1, 122.3, 78.6, 77.6, 74.1, 71.5, 71.2, 52.9, 48.5, 36.5, 25.1, 16.4, 15.2. High-Res MS (ESI): m/z 777.1986 ([M+2H]$^{2+}$), calculated 777.1972.

EXAMPLE 2

Figure 3:
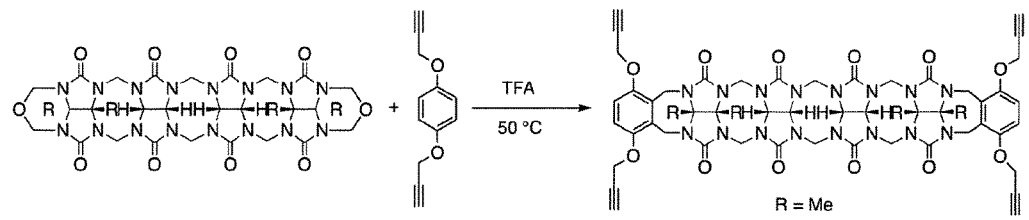

Propargyl Host (FIG. 3).

Methyl tetramer (1.70 g, 2.18 mol) in TFA (5 mL), 1,4-bis(prop-2-yn-1-yloxy)benzene (1.62 g, 8.71 mmol) was added. The solution was heated at 50° C. for 4 h. The solvent was removed with rotary evaporation. The crude product was further dried on high vacuum and then washed with water (50 mL). The solid was washed with acetone (50 mL×2) and filtered. Then this solid was dissolved in concentrated HCl (50 mL) and then precipitated by adding water (100 mL) to yield a white solid (1.1 g, 1.0 mmol, 45%). M.P.>260° C. (decomposed). IR (ATR, cm$^{-1}$): 2939 w, 1721 m, 1463 m, 1380 m, 1314 w, 1231 m, 1211 m, 1186 m, 1090 m, 941 s, 848 w, 796 m, 758 m, 616 m. $^1$H NMR (400 MHz, D$_2$O): 6.92 (s, 4H), 5.54 (d, J=14.9, 2H), 5.45 (d, J=15.0, 4H), 5.34 (d, J=9.0, 2H), 5.23 (d, J=9.0, 2H), 5.15 (d, J=15.8, 4H), 4.79 (d, J=15.0, 4H), 4.72 (d, J=15.0, 4H), 4.10 (d, J=15.8, 4H), 4.03 (d, J=15.0, 4H), 4.03 (d, J=14.9, 2H), 3.52 (s, 4H), 1.65 (s, 6H), 1.61 (s, 6H). $^{13}$C NMR (125 MHz, DMSO-d$^6$): δ156.6, 155.2, 150.7, 129.6, 115.6, 81.3, 79.1, 78.5, 77.5, 71.9, 71.5, 59.0, 54.2, 49.4, 35.6, 18.0, 16.9. HR-MS (ESI): m/z 1117.4007 ([M+H]$^+$), calculated 1117.4029.

Figure 4:
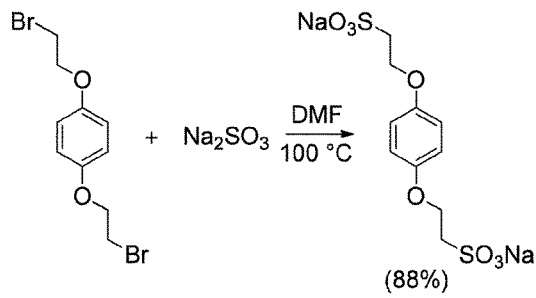

Ethanesulfonate Wall (FIG. 4).

1,4-bis(2-bromoethoxy)benzene (2.00 g, 6.13 mmol) and sodium sulfite (3.10 g, 24.5 mmol) were mixed and dissolved in DMF (20 mL). The mixture was stirred at 100° C. under N$_2$ for 12 h and then water (20 mL) was added. The mixture was allowed to cool to RT and the product precipitated as white crystals. The solid was collected by filtration and then purified by recrystallization from water. Drying under high vacuum gave Sodium 2,2'-(1,4-phenylenebis (oxy))diethanesulfonate as a white solid (2.01 g, 88%). $^1$H NMR (400 MHz, D$_2$O): 7.03 (s, 4H), 4.39 (t, J=6.2, 4H), 3.36 (t, J=6.2, 4H). $^{13}$C NMR (125 MHz, D$_2$O, 1,4-dioxane as internal reference): δ151.5, 115.5, 63.3, 49.3.

Figure 5:
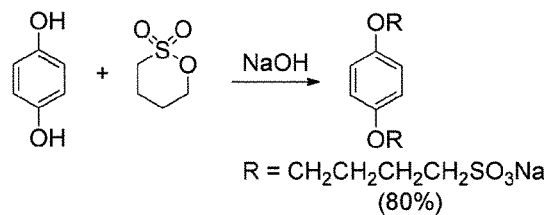

Butanesulfonate Wall (FIG. 5).

A solution of butanesultone (24.5 g, 200 mmol) in 1,4-dioxane (160 mL) was added into a solution of hydroquinone (8.80 g, 80.0 mmol) in aqueous NaOH solution (10 wt %, 120 mL). The mixture was stirred at RT for 12 h then filtered to collect the crude solid. The solid was stirred with acetone (200 mL) then dried under high vacuum to yield Sodium 4,4'-(1,4-phenylenebis(oxy))dibutane-1-sulfonate as a white solid (25.1 g, 80%). $^1$H NMR (400 MHz, D$_2$O): 7.02 (s, 4H), 4.09 (t, J=5.7, 4H), 2.99 (t, J=7.4, 4H), 1.85-2.00 (m, 8H). $^{13}$C NMR (125 MHz, D$_2$O, 1,4-dioxane as internal reference): δ152.1, 115.8, 68.3, 50.2, 26.8, 20.4.

Figure 6:
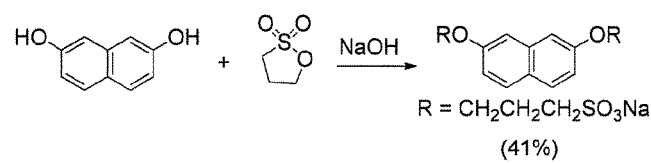

2,7-Naphthalenesulfonate Wall (FIG. 6).

A solution of propanesultone (38.0 g, 300 mmol) in 1,4-dioxane (240 mL) was added into a solution of naphthalene-2,7-diol (20.0 g, 124 mmol) in NaOH (10 wt %, 160 mL). This solution was stirred at RT for 12 h. After filtration, the solid was collected and then dissolved in H$_2$O (100 mL) and then was precipitated by the addition of CH$_3$CN (600 mL). The solid was collected by filtration and then dried under high vacuum to yield a pale green solid (23.2 g, 41%). $^1$H NMR (400 MHz, D$_2$O): 7.77 (d, J=8.9, 2H), 7.23 (m, 2H), 7.07 (dd, J=8.9, 2.4, 2H), 4.24 (t, J=6.4, 4H), 3.05-3.15 (m, 4H), 2.15-2.30 (m, 4H). $^{13}$C NMR (125 MHz, D$_2$O, 1,4-dioxane as internal reference): δ156.2, 135.0, 128.9, 123.9, 115.8, 106.3, 66.0, 47.4, 23.7.

Figure 7:
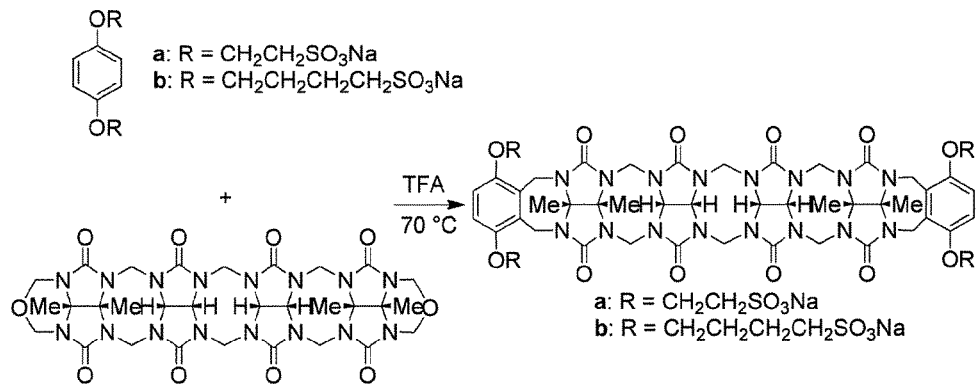

Ethanesulfonate Host a (FIG. 7).

Sodium 2,2'-(1,4-phenylenebis (oxy))diethanesulfonate (1.81 g, 0.23 mmol) was added into a solution of methyl tetramer (0.64 g, 0.77 mmol) in TFA (2 mL). The mixture was stirred and heated at 70° C. for 4 h. The solvent was removed with under reduced pressure and the solid was further dried under high vacuum. The solid was washed with the mixture of water and acetone (1:2, v/v, 30 mL) twice and then dissolved in water and adjusted to pH=7 by adding 1 M aqueous NaOH. The solvent was removed under reduced pressure and then the solid was further dried under high vacuum to yield product a as a white solid (0.72 g, 61%). $^1$H NMR (400 MHz, D$_2$O): 6.94 (s, 4H), 5.67 (d, J=15.5, 2H), 5.56 (d, J=16.0, 4H), 5.44 (d, J=7.6, 2H), 5.38 (d, J=7.6, 2H), 5.35 (d, J=16.3, 4H) 4.45-4.25 (m, 8H), 4.24 (d, J=16.0, 4H), 4.21 (d, J=16.3, 4H) 4.10 (d, J=15.5, 2H), 3.55-3.40 (m, 4H), 3.35-3.20 (m, 4H), 1.79 (s, 6H), 1.75 (s, 6H). $^{13}$C NMR (125 MHz, D$_2$O, 1,4-dioxane as internal reference): δ156.4, 155.9, 149.6, 127.8, 114.4, 78.4, 77.1, 70.9, 70.8, 65.2, 52.2, 50.1, 48.0, 34.8, 15.6, 14.6.

Butanesulfonate Host b (FIG. 7).

Sodium 4,4'-(1,4-phenylenebis (oxy))bis(butane-1-sulfonate) (6.50 g, 15.4 mmol) was added into a solution of methyl tetramer (3.00 g, 3.84 mmol) in TFA (30 mL). The mixture was stirred and heated at 70° C. for 4 h. The solvent was removed under reduced pressure and the solid was further dried under high vacuum. The solid was washed twice with the mixture of water and acetone (1:2, v/v, 300 mL) and then dissolved in water and adjusted to pH=7 by adding 1 M aqueous NaOH. The solvent was removed under reduced pressure and then the solid was further dried under high vacuum to yield product b as a white solid (2.33 g, 40%). $^1$H NMR (400 MHz, D$_2$O): 7.01 (s, 4H), 5.62 (d, J=15.2, 2H), 5.51 (d, J=16.0, 4H), 5.45 (d, J=8.9, 2H), 5.35 (d, J=8.9, 2H), 5.24 (d, J=16.0, 4H), 4.30 (d, J=16.0, 4H), 4.25 (d, J=16.0, 4H), 4.04 (d, J=15.2, 2H), 3.90-3.75 (m, 8H), 2.90-2.75 (m, 4H), 2.70-2.55 (m, 4H), 1.79 (s, 12H), 1.79-1.30 (m, 16H).

Figure 8:
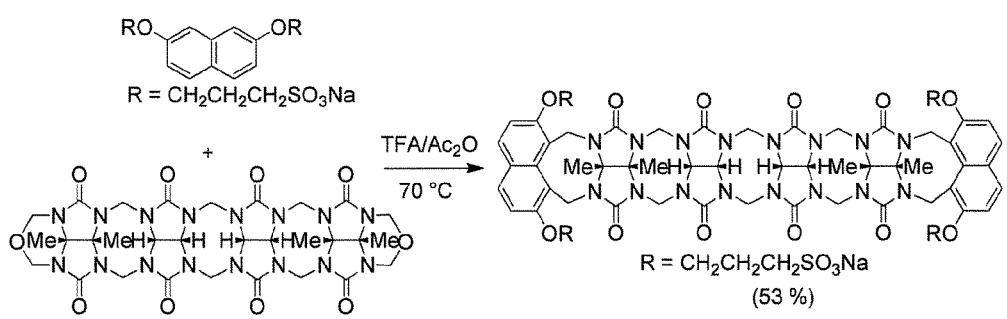

Naphthalene propanesulfonate Host (FIG. 8).

Sodium 3,3'-(naphthalene-2,7-diylbis (oxy))dipropane-1-sulfonate (229 mg, 0.152 mmol) was added into a solution of methyl tetramer (100 mg, 0.128 mmol) in a mixture of TFA/Ac$_2$O (1:1, 2 mL). The mixture was stirred and heated at 70° C. for 3 h and then was poured into acetone (30 mL).

The solid was collected with filtration. The crude solid was dissolved in H₂O (10 mL), and then precipitated by the addition of acetone (30 mL). The product was then collected by filtration and then recrystallized from water and acetone (1:1, v/v, 5 mL). The purified product was obtained as a pale beige solid after drying under high vacuum (112 mg, 53%). $^1$H NMR (400 MHz, D₂O): 6.95 (d, J=8.9, 4H), 6.48 (d, J=8.9, 4H), 5.60 (d, J=16.3, 4H), 5.58 (d, J=15.4, 6H), 5.30 (d, J=9.0, 2H), 5.20 (d, J=9.0, 2H), 4.72 (d, J=16.3, 4H), 4.16 (d, J=15.4, 4H), 4.00-3.85 (m, 8H), 3.30-3.05 (m, 8H), 2.35-2.10 (m, 8H), 1.76 (s, 12H). $^{13}$C NMR (125 MHz, D₂O, 1,4-dioxane as internal reference): δ156.4, 156.1, 155.0, 131.6, 127.3, 116.3, 112.6, 76.8, 75.4, 70.8, 68.1, 52.2, 48.0, 47.9, 33.1, 29.7, 24.4, 16.6, 15.2, (only 19 out of the 20 expected resonances were observed).

Figure 9:
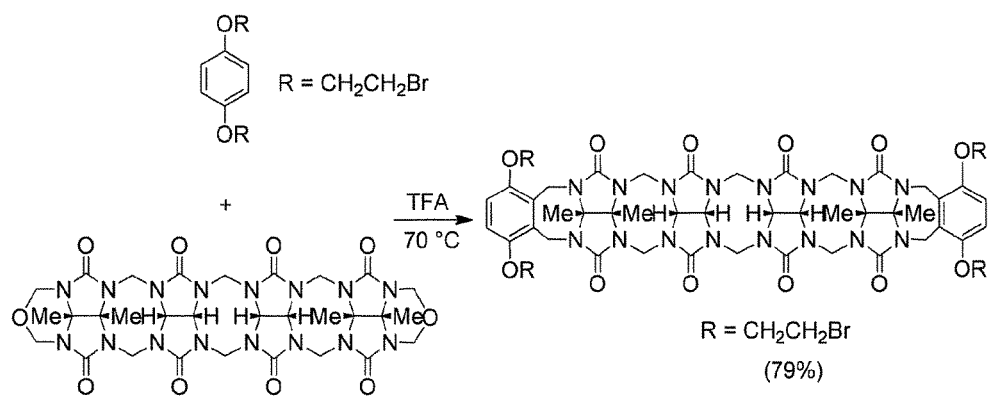

Tetrabromo Host (FIG. 9).

1,4-bis(2-bromoethoxy)benzene (1.70 g, 5.21 mmol) and methyl tetramer (1.20 g, 1.53 mmol) were mixed in a round bottom flask. TFA (12 mL) was added, and the mixture was stirred at 70° C. for 3 h. The reaction mixture was poured into MeOH (100 mL), and the solid was collected by filtration. The crude product was stirred with water (150 mL) and then acetone (150 mL) at RT and the solid was isolated by filtration. Drying at high vacuum gave the product as a white powder (1.71 g, 79%). M.p. 283-285° C. IR (ATR, cm⁻¹): 3000 br, 1704 m, 1456 m, 1311 m, 1225 s, 1177 s, 1080 s, 966 m, 922 m, 818 m, 794 s, 754 m, 666 m. $^1$H NMR (400 MHz, DMSO): 6.91 (s, 4H), 5.59 (d, J=14.4, 2H), 5.51 (d, J=15.2, 4H), 5.38 (d, J=9.0, 2H), 5.30-5.25 (m, 6H), 4.50-4.40 (m, 4H), 4.25-4.20 (m, 10H), 4.06 (d, J=15.2, 4H), 3.90-3.80 (m, 8H), 1.69 (s, 6H), 1.66 (s, 6H). $^{13}$C NMR (125 MHz, DMSO, 1,4-dioxane as internal reference): δ156.0, 154.6, 151.0, 129.5, 116.7, 78.0, 76.8, 71.5, 71.4, 71.0, 53.6, 48.9, 35.2, 33.5, 17.2, 16.3.

Figure 10:
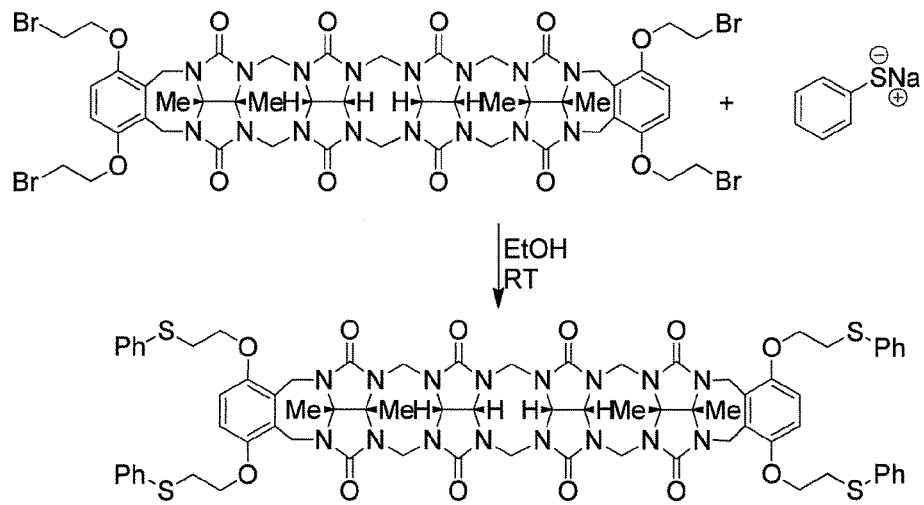

Tetrathiophenyl Host (FIG. 10).

Sodium benzenethiolate (48 mg, 0.36 mmol) was dissolved in EtOH (2 mL). Tetrabromohost (100 mg, 0.072 mmol) was added and the reaction mixture was stirred at RT for 12 h. The reaction mixture was centrifuged to collect the crude product. The solid was washed with EtOH (10 mL) and then H₂O (10 mL). A pale yellow solid was obtained after drying under high vacuum (63 mg, 58%). $^1$H NMR (400 MHz, DMSO): 7.45-7.05 (m, 20H), 6.68 (s, 4H), 5.62 (d, J=15.3, 2H), 5.51 (d, J=14.8, 4H), 5.39 (d, J=8.0, 2H), 5.27 (d, J=8.0, 2H), 5.24 (d, J=15.7, 4H), 4.25-4.10 (m, 4H), 4.10-3.85 (m, 14H), 3.45-3.30 (m, 8H), 1.69 (s, 6H), 1.63 (s, 6H).

Figure 11:
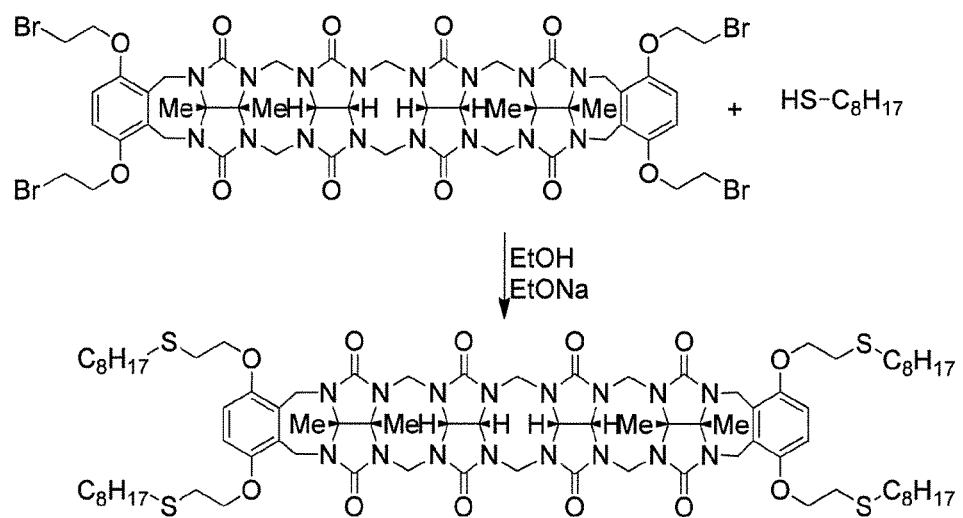

Tetra Octanethioether Host (FIG. 11).

Octane-1-thiol (53 mg, 0.36 mmol) was dissolved in EtOH (2 mL). Tetrabromohost (100 mg, 0.072 mmol) was added and the reaction mixture was stirred at RT for 3 h. The reaction mixture was centrifuged to collect crude solid. The solid was washed with EtOH (10 mL) and then H₂O (10 mL). A white solid was obtained after drying under high vacuum (103 mg, 72%). $^1$H NMR (400 MHz, DMSO): 6.82 (s, 4H), 5.59 (d, J=12.2, 2H), 5.48 (d, J=14.8, 4H), 5.35 (d, J=8.6, 2H), 5.24 (d, J=8.6, 2H), 5.24 (d, J=16.4, 4H), 4.25-4.20 (m, 4H), 4.08 (d, J=16.4, 4H), 4.04 (d, J=14.8, 4H), 4.10-4.00 (m, 4H), 3.99 (d, J=12.2, 2H), 2.88 (t, J=5.6, 8H), 2.63 (t, J=7.2, 8H), 1.66 (s, 6H), 1.62 (s, 6H), 1.56 (m, 8H), 1.40-1.15 (m, 40H), 0.83 (t, J=7.2, 12H).

Figure 12:
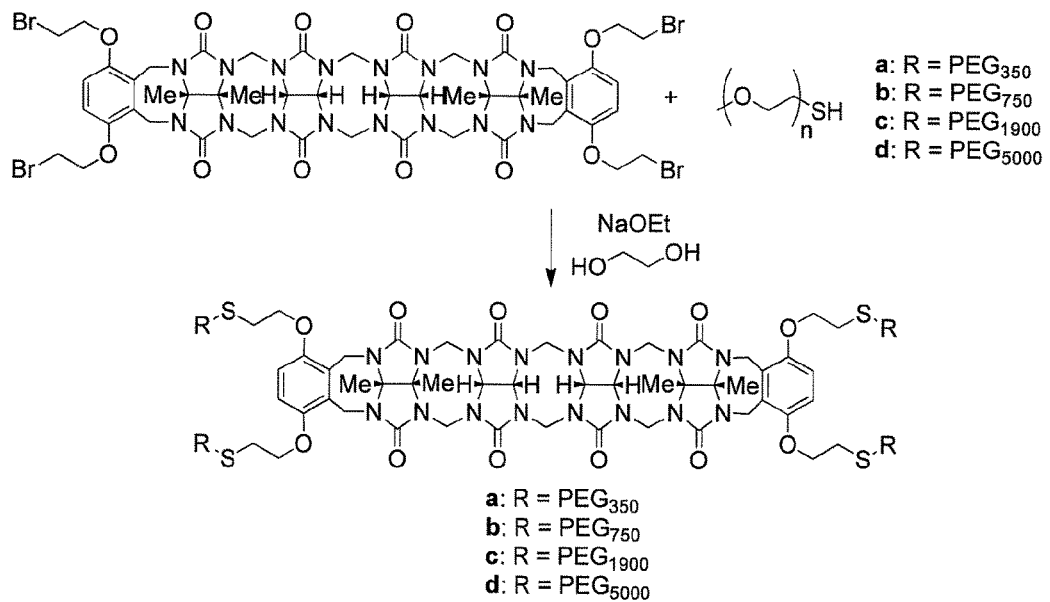

PEG 350 Host (FIG. 12).

PEG 350 (176 mg, 0.43 mmol) and NaOEt (29 mg, 0.43 mmol) was dissolved in ethylene glycol (2 mL). Tetrabromo Host (100 mg, 0.072 mmol) was added and the reaction mixture was stirred and heated at 50° C. for 12 h. The reaction mixture was centrifuged to remove insoluble material and the clear solution was concentrated and poured into diethyl ether (10 mL). The white precipitate was collected by centrifugation. A dark yellow gel was obtained after drying under high vacuum (150 mg, 82%). $^1$H NMR (400 MHz, D₂O): 6.64 (s, 4H), 5.64 (d, J=16.0, 4H), 5.60-5.35 (m, 8H), 5.34 (d, J=8.4, 2H), 4.35 (d, J=16.0, 4H), 4.20-4.10 (m, 12H), 4.05, (d, J=12.3, 2H), 3.95-3.55 (m, 160H), 3.38 (s, 12H), 3.11 (t, J=6.0, 8H), 2.96 (t, J=6.0, 8H), 1.89 (s, 6H), 1.86 (s, 6H).

PEG 750 Host (FIG. 12).

PEG 750 (349 mg, 0.43 mmol) and NaOEt (29 mg, 0.43 mmol) was dissolved in ethylene glycol (2 mL). Tetrabromo Host (100 mg, 0.072 mmol) was added and the reaction mixture was stirred and heated at 70° C. for 12 h. The reaction mixture was centrifuged to remove insoluble material and a mixture of CH₂Cl₂ and MeOH (5 mL, 4:1) was added to the supernatant. Diethyl ether (10 mL) was added and then the mixture was centrifuged to isolate a white precipitate. A pale yellow solid was obtained after drying under high vacuum (172 mg, 58%). $^1$H NMR (400 MHz, D₂O): 7.03 (s, 4H), 5.68 (d, J=16.2, 2H), 5.56 (d, J=15.6, 4H), 5.45-5.25 (m, 8H), 4.30-4.00 (m, 18H), 3.95-3.55 (m, 320H), 3.32 (s, 12H), 3.00-2.75 (m, 8H), 2.65 (t, J=6.0, 8H), 1.76 (s, 6H), 1.72 (s, 6H).

PEG 1900 Host (FIG. 12).

PEG 1900 (823 mg, 0.43 mmol) and NaOEt (29 mg, 0.43 mmol) was dissolved in ethylene glycol (2 mL). Tetrabromo Host (100 mg, 0.072 mmol) was added and the reaction mixture was stirred and heated at 70° C. for 12 h. The reaction mixture was centrifuged to remove insoluble material and a mixture of CH₂Cl₂ and MeOH (5 mL, 4:1) was added to the supernatant. Diethyl ether (10 mL) was added and then the mixture was centrifuged to isolate a white precipitate. The product was further purified by GPC using Sephadex-G25. A pale yellow solid was obtained after drying under high vacuum (213 mg, 34%). $^1$H NMR (400 MHz, D₂O): 6.49 (s, 4H), 5.46 (d, J=16.4, 4H), 5.40-5.20 (m, 8H), 5.19 (d, J=8.4, 2H), 4.15 (d, J=16.0, 4H), 4.10-3.85 (m, 16H), 3.95-3.55 (m, 800H), 3.22 (s, 12H), 2.96 (t, J=6.2, 8H), 2.81 (t, J=6.2, 8H), 1.73 (s, 6H), 1.71 (s, 6H).

PEG 5000 Host (FIG. 12).

PEG 5000 (2.16 g, 0.43 mmol) and NaOEt (29 mg, 0.43 mmol) was dissolved in ethylene glycol (4 mL). Tetrabromo Host (100 mg, 0.072 mmol) was added and the reaction mixture was stirred and heated at 70° C. for 12 h. The reaction mixture was centrifuged to remove insoluble material and a mixture of CH₂Cl₂ and MeOH (5 mL, 4:1) was added to the supernatant. Diethyl ether (10 mL) was added and then the mixture was centrifuged to isolate a white precipitate. The product was further purified by GPC using Sephadex-G25. A pale yellow solid was obtained after drying under high vacuum (351 mg, 23%). $^1$H NMR (400 MHz, D₂O): 7.05 (s, 4H), 5.71 (d, J=15.5, 2H), 5.62 (d, J=15.6, 4H), 5.60-5.25 (m, 8H), 4.30-4.00 (m, 18H), 3.95-3.55 (m, 1840H), 3.32 (s, 12H), 3.00-2.75 (m, 8H), 2.66 (t, J=6.0, 8H), 1.76 (s, 6H), 1.74 (s, 6H).

Figure 13:
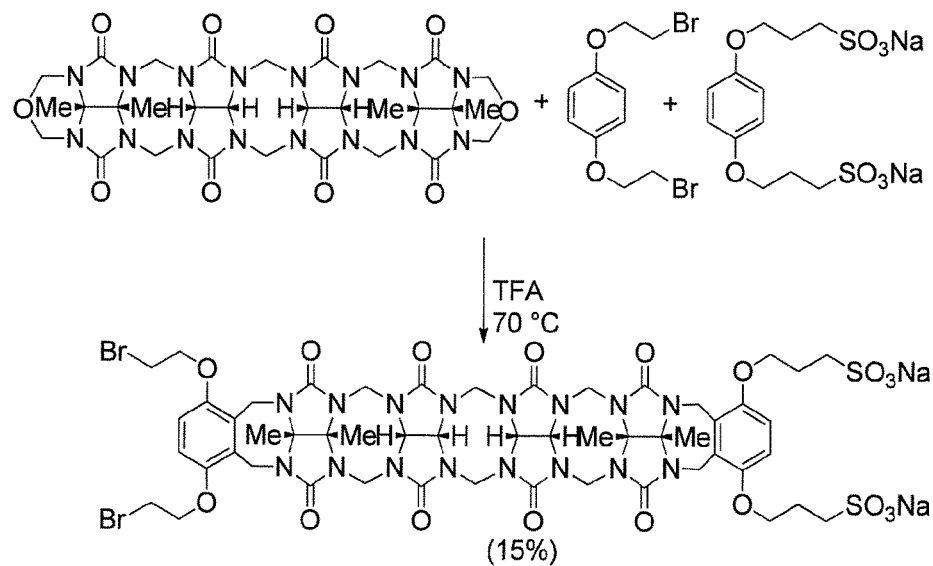

Dibromo Dipropanesulfonate Host (FIG. 13).

1,4-bis(2-bromoethoxy) benzene (250 mg, 0.768 mmol) and sodium 3,3'-(1,4-phenylenebis (oxy))bis(propane-1-sulfonate) (102 mg, 0.256 mmol) were added into a solution of methyl tetramer (200 mg, 0.256 mmol) in TFA (2.5 mL). The mixture was stirred and heated at 70° C. for 3 h and then was poured into acetone (150 mL). The solid was collected by filtration. The crude solid was stirred with water (30 mL×3) at RT for 4 hr. The filtrate was collected and the solvent was removed under reduced pressure. The product was purified by recrystallization from H₂O and MeOH (1:1, 15 mL). The product was obtained as a white solid after drying under high vacuum (112 mg, 53%). $^1$H NMR (400 MHz, D$_2$O): 6.97 (s, 2H), 6.72 (s, 2H), 5.62 (d, J=15.9, 2H), 5.60 (d, J=15.9, 2H), 5.53 (d, J=16.4, 2H), 5.45 (d, J=5.8, 2H), 5.43 (d, J=15.9, 2H), 5.40 (d, J=5.0, 2H), 5.21 (d, J=10.8, 2H), 4.27 (d, J=16.4, 2H), 4.25-4.20 (m, 8H), 4.15-4.05 (m, 8H), 3.95-3.75 (m, 4H), 3.45-3.35 (m, 2H), 3.25-3.20 (m, 2H), 3.14 (t, J=7.7, 4H), 2.35-2.15 (m, 4H), 1.87 (s, 3H), 1.81 (s, 3H), 1.67 (s, 3H), 1.66 (s, 3H).

Figure 14:
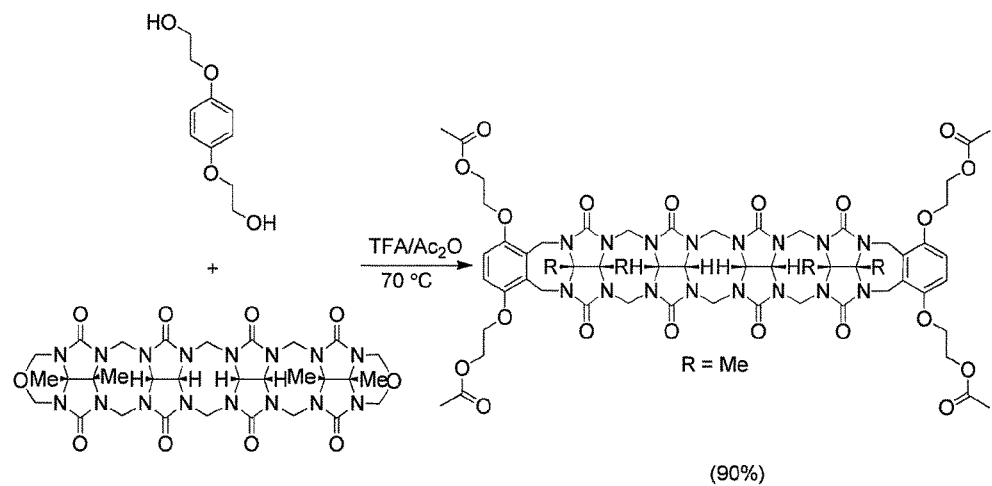

Tetra Ester Host (FIG. 14).

2,2'-(1,4-phenylenebis(oxy))diethanol (1.02 g, 5.12 mmol) and methyl tetramer (1.00 g, 1.28 mmol) were mixed as solid and then dissolved in a mixture of TFA and Ac$_2$O (1:1, 10 mL). The mixture was stirred at 70° C. for 3.5 h and then was poured into MeOH (150 mL). The solid was collected by filtration and was washed with acetone (100 mL) and water (100 mL). After drying under high vacuum, the product was obtained as a white powder (1.51 g, 90%). M.p.>300° C. IR (ATR, cm$^{-1}$): 3000 w, 1711 s, 1456 s, 1313 m, 1225 s, 1178 s, 1076 s. $^1$H NMR (400 MHz, DMSO): 6.85 (s, 4H), 5.58 (d, J=16.3, 2H), 5.48 (d, J=15.6, 4H), 5.37 (d, J=9.0, 2H), 5.27 (d, J=9.0, 2H), 5.23 (d, J=16.0, 4H), 4.45-4.30 (m, 4H), 4.30-4.05 (m, 14H), 3.50-3.45 (m, 8H), 2.06 (s, 12H), 1.76 (s, 12H).

Figure 15:
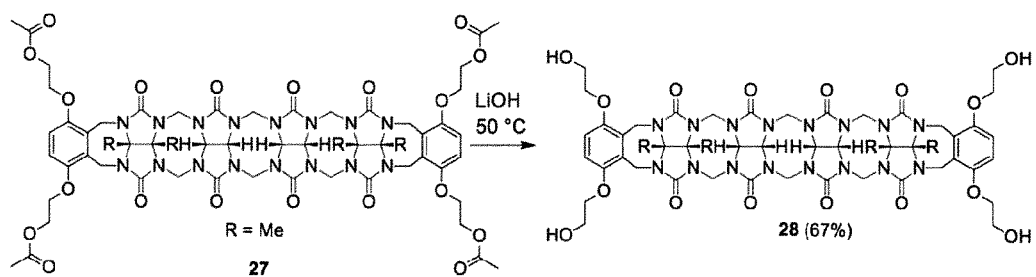

Tetra Hydroxy Host (FIG. 15).

Tetra Ester Host (0.400 g, 0.305 mmol) was added into an aqueous solution of LiOH (2.5 M, 7.5 mL). The mixture was stirred at 50° C. for 0.5 h and then the solid was collected by filtration. The solid was wash with 0.1 M HCl to neutral and then stirred with EtOH (30 mL), and water (30 mL). After drying under high vacuum, a white solid was obtained (0.234 g, 67%). $^1$H NMR (400 MHz, D$_2$O): 6.95 (s, 4H), 5.62 (d, J=15.3, 2H), 5.52 (d, J=15.7, 4H), 5.43 (d, J=8.0, 2H), 5.20 (d, J=8.0, 2H), 4.72 (d, J=16.2, 4H), 4.28 (d, J=15.7, 4H), 4.23 (d, J=16.2, 4H), 4.19 (d, J=15.3, 2H), 3.85-3.50 (m, 8H), 3.45-2.85 (m, 8H), 1.76 (s, 12H).

Figure 16:
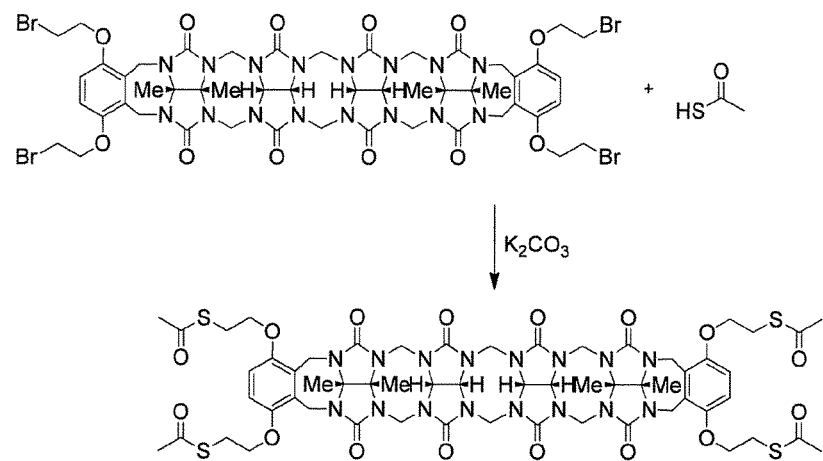

Tetrathioacetate Host (FIG. 16).

K$_2$CO$_3$ (99 mg, 0.43 mmol) and thiolacetic acid (55 mg, 0.43 mmol) was added into DMF (2 mL) and was stirred at RT for 15 min under N$_2$. Tetrabromo Host (100 mg, 0.072 mmol) was added as a solid. The mixture was stirred at 50° C. for 12 h and then was poured into H$_2$O (6 mL). The solid was collected by filtration and was then washed with H$_2$O (5 mL) and acetone (5 mL). A beige solid was obtained after drying under high vacuum (73 mg, 74%). $^1$H NMR (400 MHz, DMSO): 6.85 (s, 4H), 5.58 (d, J=16.3, 2H), 5.48 (d, J=15.6, 4H), 5.38 (d, J=9.0, 2H), 5.27 (d, J=9.0, 2H), 5.22 (d, J=16.0, 4H), 4.25-4.10 (m, 4H), 4.15-3.90 (m, 14H), 3.35-3.25 (m, 8H), 2.37 (s, 12H), 1.68 (s, 6H), 1.64 (s, 6H).

Figure 17:
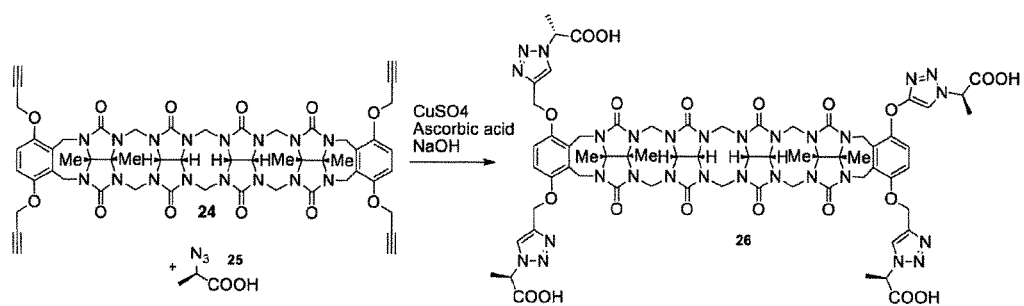
Figure 18:
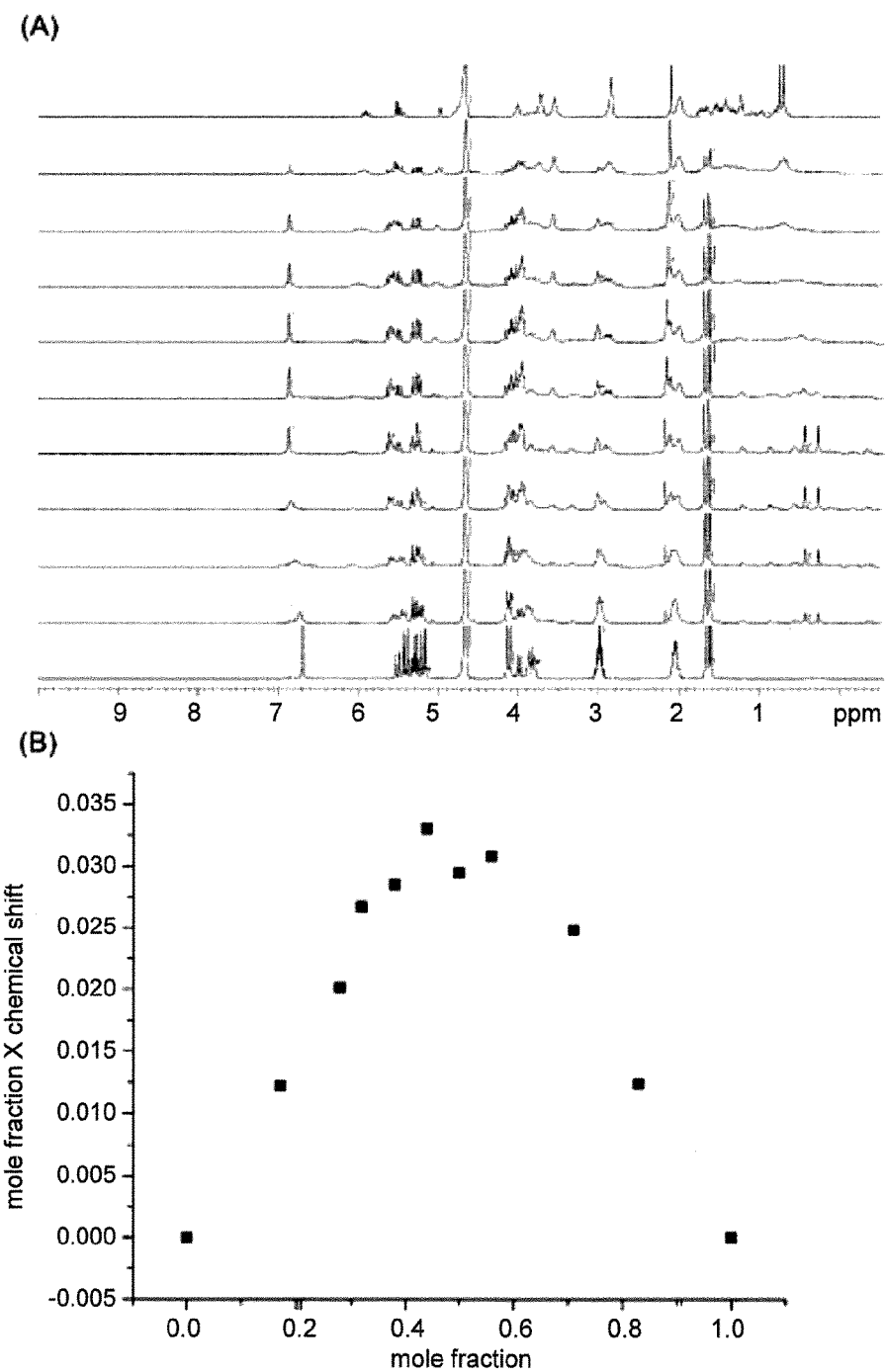
Figure 19:
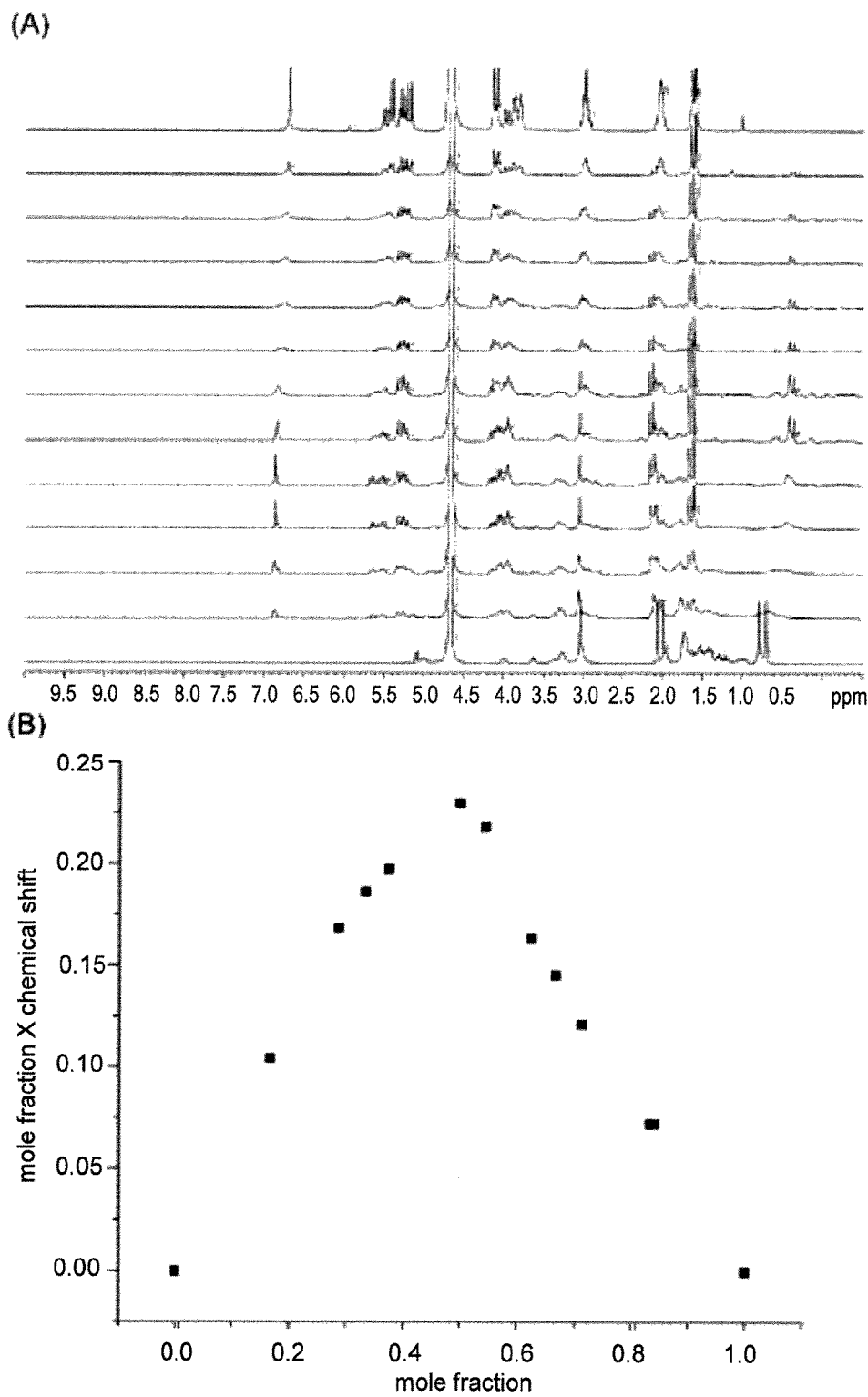
FIG. 19. An example of a Job plot of Motor1 and Vecuronium bromide (total concentration 5 mM, 20 mM $NaH_2PO_4$ buffer, pH 7.4): (A) Stack plot of $^1H$ NMR spectra; (B) Job plot of Motor1 (constructed using the chemical shift of the downfield singlet).
Figure 20:
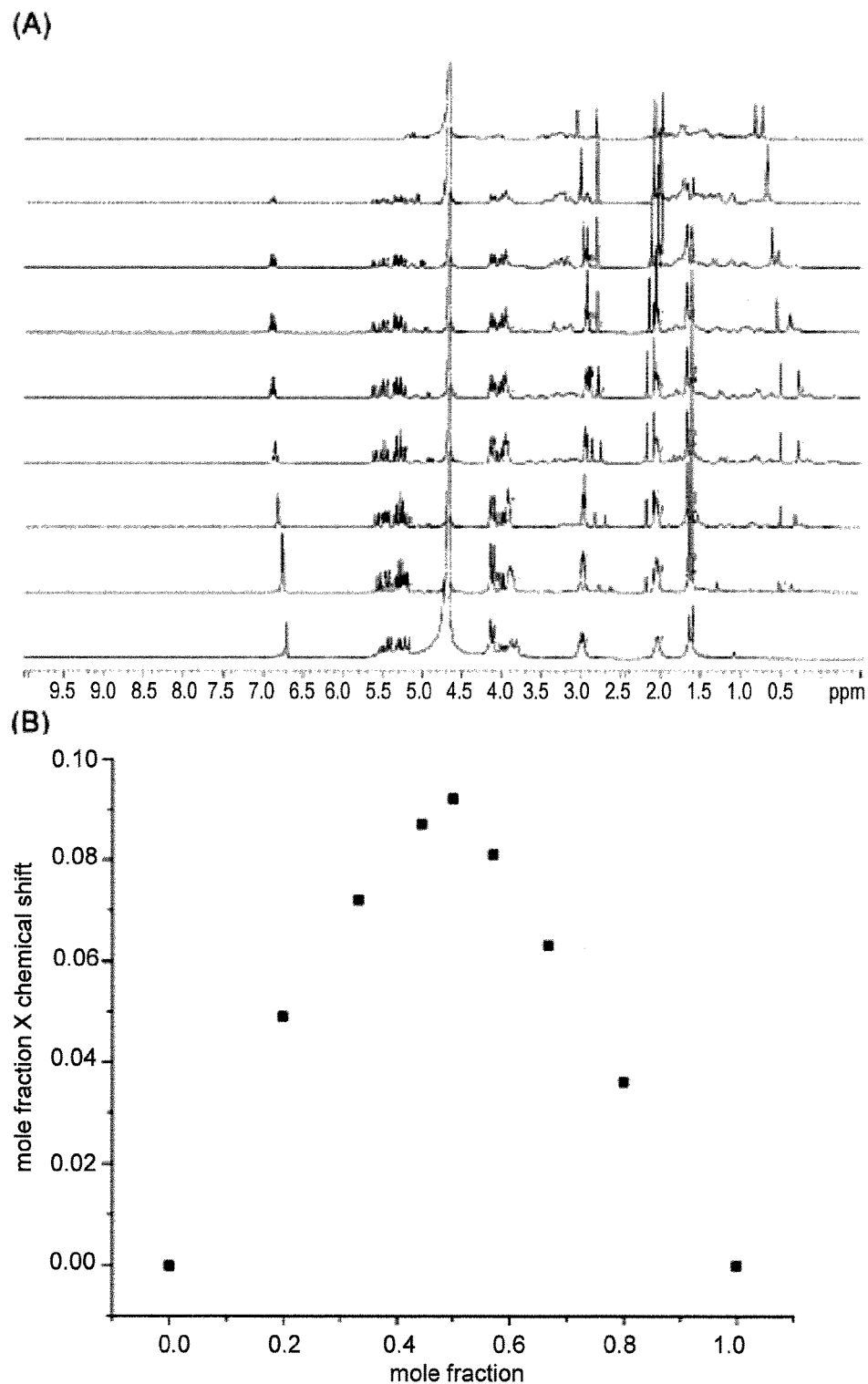
FIG. 20. An example of a Job plot of Motor1 and Pancuronium bromide (total concentration 5 mM, 20 mM $NaH_2PO_4$ buffer, pH 7.4): (A) Stack plot of $^1H$ NMR spectra; (B) Job plot of Motor1 (constructed using the chemical shift of the aromatic proton on Motor1).
Figure 21:
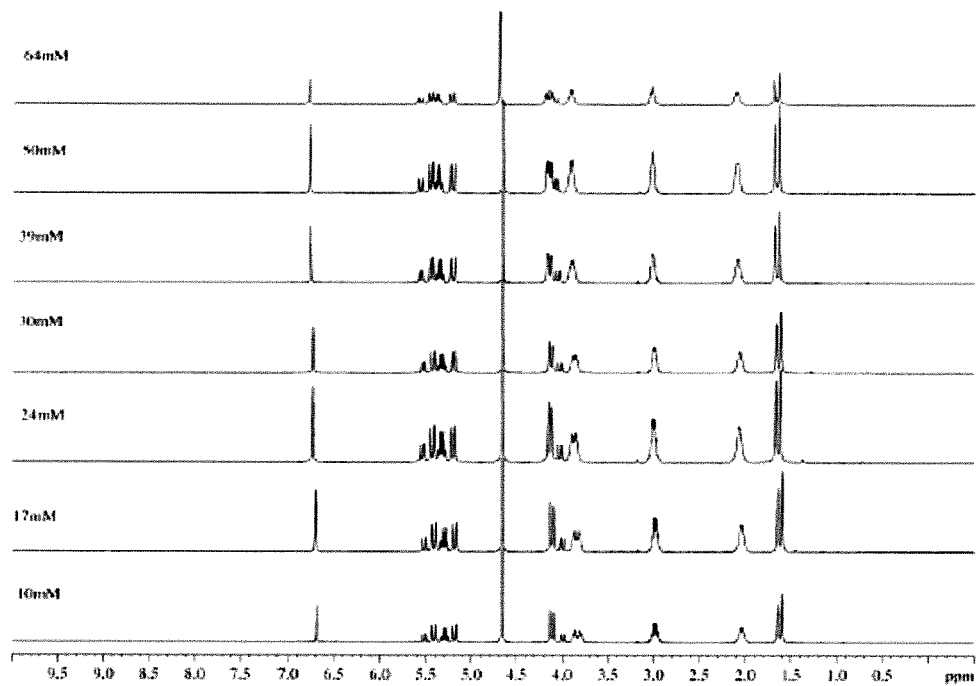
FIG. 21. An example of $^1$H NMR spectra recorded for Motor1 at varied concentration (400 MHz, 20 mM NaD$_2$PO$_4$, pD=7.4) for self-association study.
Figure 22:
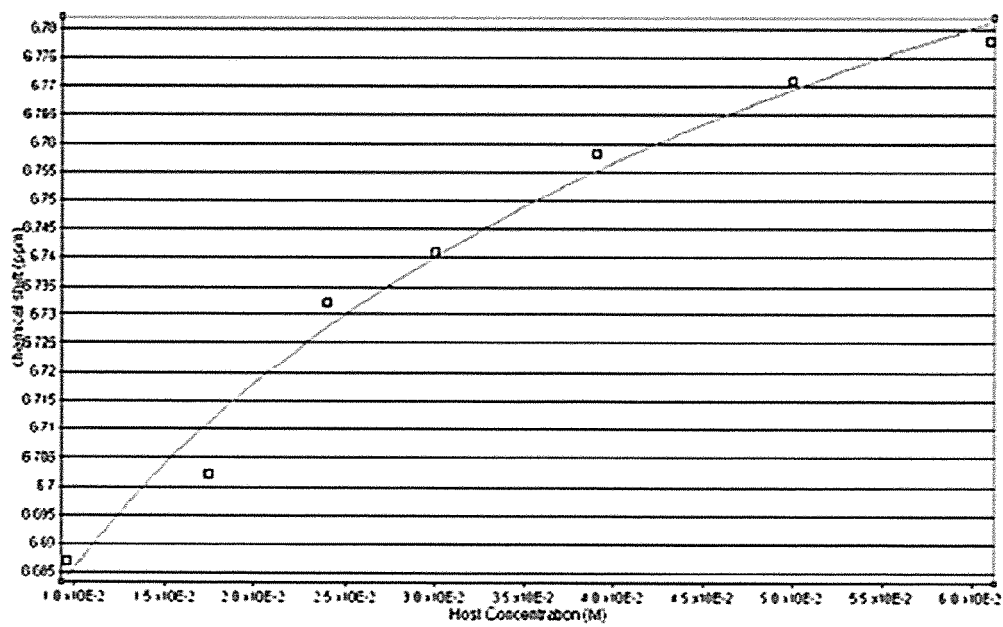
FIG. 22. An example of a plot of chemical shift of Motor1 versus [Motor1]. The solid line represents the best non-linear fitting of the data to a two-fold self-association model with $K_a$=47 M.
Figure 23:
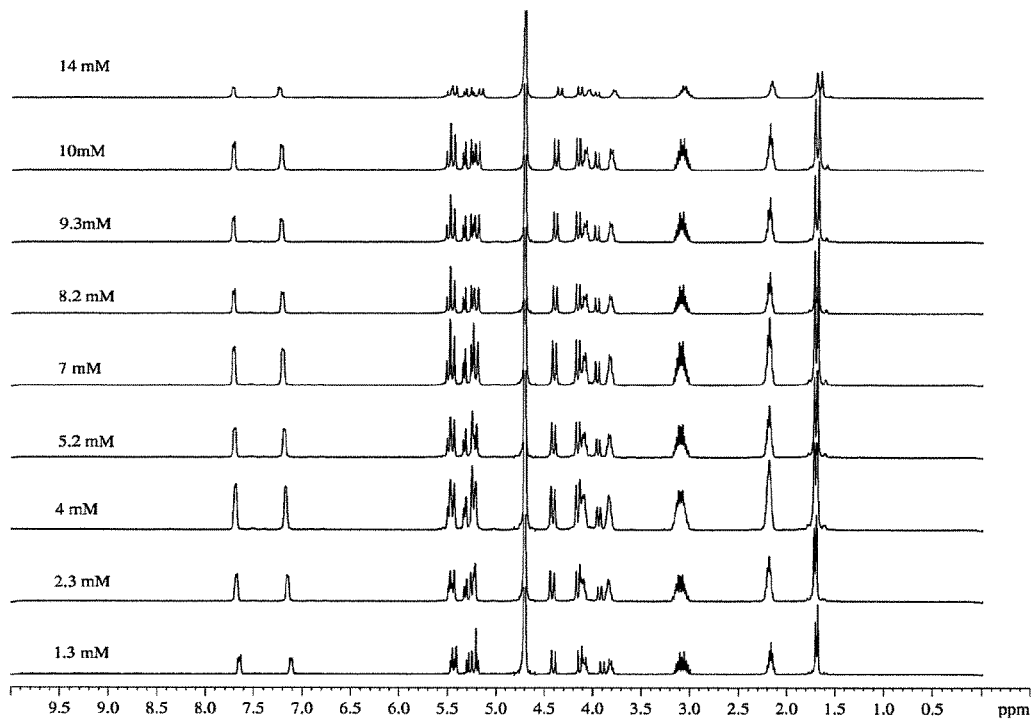
FIG. 23. An example of $^1$H NMR spectra recorded for Motor2 at varied concentration (400 MHz, 20 mM NaD$_2$PO$_4$, pD=7.4) for self-association study.
Figure 24:
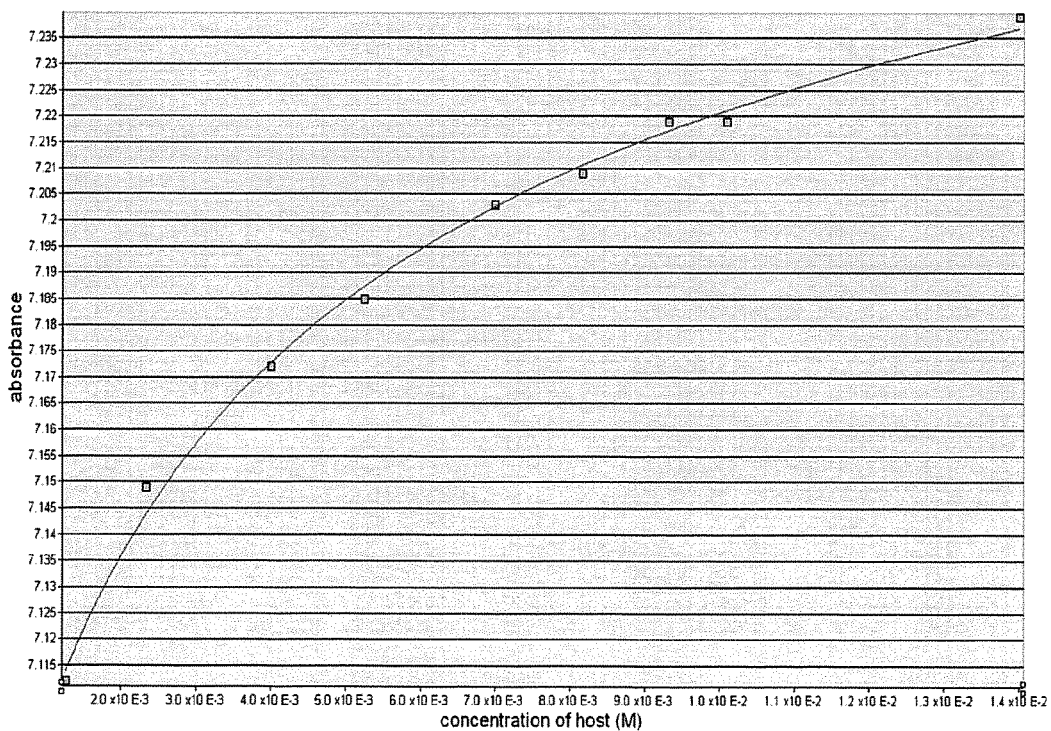
FIG. 24. An example of a plot of chemical shift of Motor2 versus [Motor2]. The solid line represents the best non-linear fitting of the data to a two-fold self-association model with $K_a$=624 M$^{-1}$.
Figure 25:
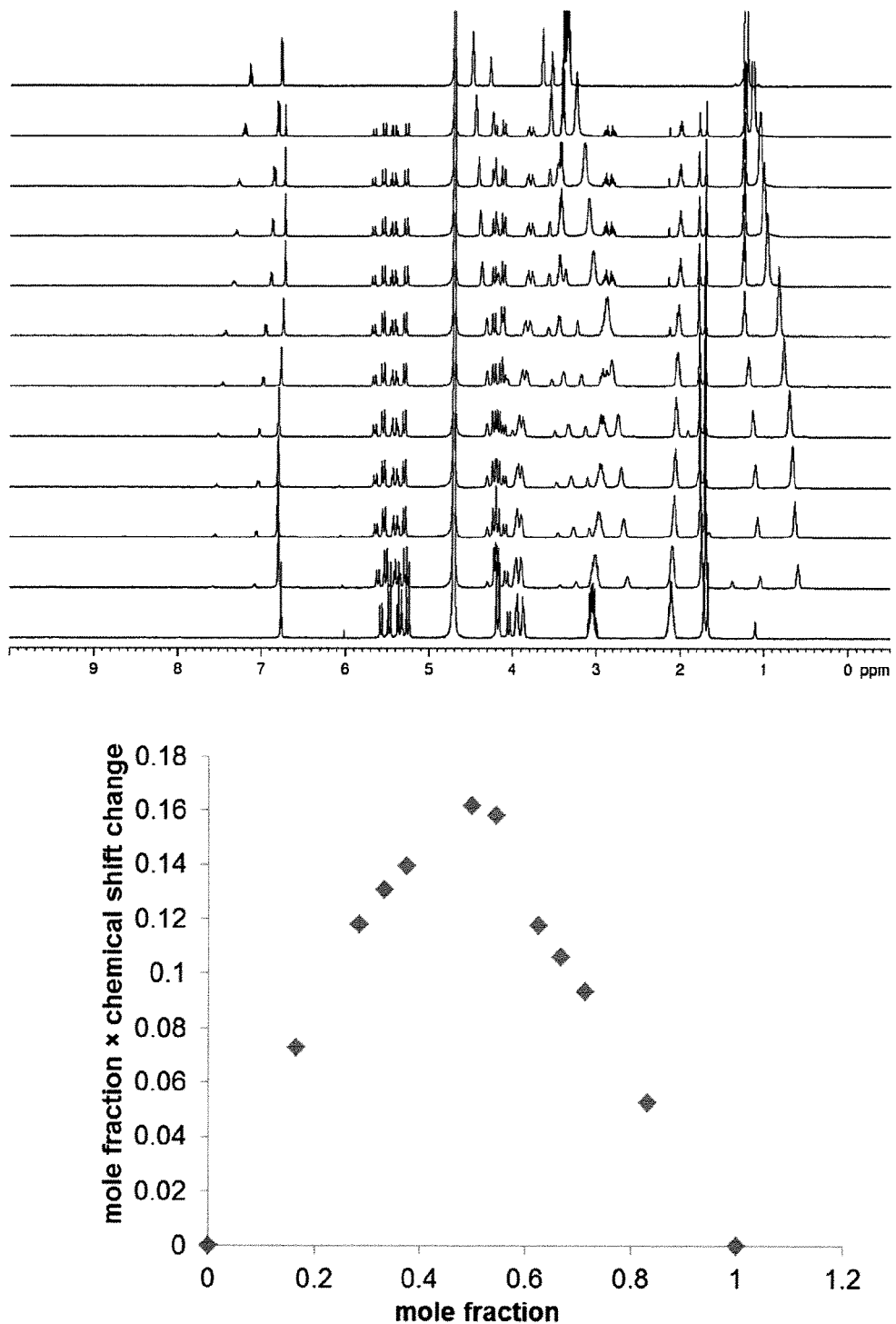
FIG. 25. An example of a Job plot of Motor1 and Gallamine (total concentration 5 mM, 20 mM NaH$_2$PO$_4$ buffer, pH 7.4): (A) Stack plot of $^1$H NMR spectra; (B) Job plot of Motor1 (constructed using the chemical shift of the aromatic proton peak on Motor1).
Figure 26:
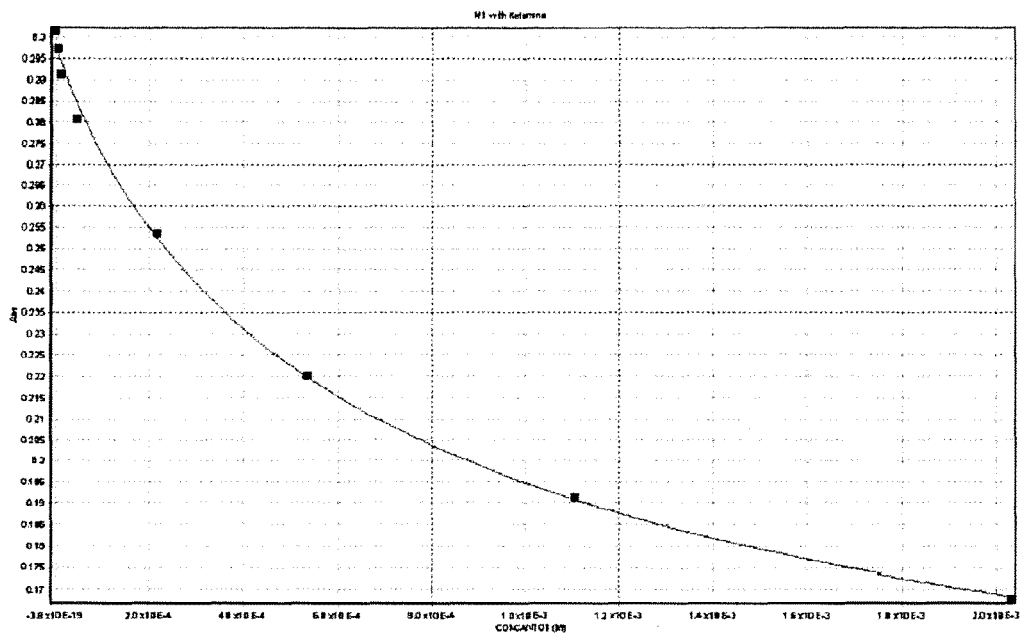
FIG. 26. An example of a non-linear fitting plot of absorbance versus concentration for the displacement titration of Motor1 complexed to Rhodamine 6G by the addition of Ketamine with Scientist™ (Conditions: Rhodamine 6G=0.010 mM, Motor1=0.009 mM, 20 mM phosphate buffer pH 7.4). $K_a$ for the complex between Motor1 and Ketamine was evaluated as 39020 M$^{-1}$.

Tetra Triazole Host (FIG. 17).

Ascorbic acid (7 mg, 0.04 mmol), NaOH (2 mg, 0.04 mmol) and CuSO$_4$ (2 mg, 0.01 mmol) was mixed and then dissolved in a mixture of H$_2$O and EtOH (1 mL, 1:1). Alkyne Host (26 mg, 0.024 mmol) and (R)-2-azidopropanoic acid (22 mg, 0.19 mmol) was added as solid. The mixture was heated with microwave at 80° C. for 30 min, and then solvent was removed under reduced pressure. The crude solid was washed with MeOH (2 mL). A yellowish solid was obtained after drying under high vacuum (15 mg, 40%). $^1$H NMR (400 MHz, DMSO): 8.44 (s, 2H), 8.34 (s, 2H), 6.97 (m, 4H), 5.65-5.45 (m, 12H), 5.39 (d, J=8.4, 2H), 5.25-5.05 (m, 18H), 4.25-4.00 (m, 4H), 1.72 (m, 12H), 1.69 (s, 6H), 1.64 (s, 6H).

EXAMPLE 3

TABLE 1

Binding constants of Motor1 towards guests:

| Guest | K$_a$ |
|---|---|
| vecuronium | 5.8 ± 0.9 × 10$^6$ |
| pancuronium | 4.5 ± 0.1 × 10$^5$ |
| atracurium | 1.4 ± 0.1 × 10$^6$ |
| tubocurarine | 4.7 ± 0.2 × 10$^5$ |
| gallamine | 6.2 ± 0.5 × 10$^6$ |
| acetylcholine | 2.4 ± 0.1 × 10$^4$ |

TABLE 2

Compounds used and their binding affinities towards Motor2.

| Compound Name | Ka (M$^{-1}$) with Motor2 |
|---|---|
| Rhodamine 6G | 2.3 ± 0.2 × 10$^6$ |
| Cyclohexanediamine | 2.1 ± 0.2 × 10$^6$ |
| Proflavin | 7.8 ± 0.8 × 10$^6$ |
| Rocuronium | 3.48 ± 0.6 × 10$^9$ |
| Vecuronium | 1.6 ± 0.2 × 10$^9$ |
| Pancuronium | 5.3 ± 0.5 × 10$^8$ |
| Atracurium besilate | 1.0 ± 0.1 × 10$^8$ |
| Gallamine | 3.2 ± 0.4 × 10$^8$ |
| Turbocurium | 2.2 ± 0.3 × 10$^5$ |
| Acetylcholine | 1.8 ± 0.2 × 10$^5$ |

EXAMPLE 4

Testing of the binding abilities of Motor1 and Motor2 with Ketamine, and Etomidate respectively.

For the binding of Motor1 and Ketamine, Rhodamine 6G was used as an indicator to perform a competition experiment to determine the binding constant. A solution of Rhodamine 6G (0.010 mM), Motor1 (0.009 mM, 2.4 mL) was titrated by a stock solution of Rhodamine 6G (0.010 mM) and Motor1 (0.009 mM) and Ketamine (2.10 mM) in Phosphate buffer (20 mM, pH=7.4). The absorbances of the solution at 550 nm were monitored by UV-VIS spectroscopy, and then used to calculate the binding constant.

TABLE 3

Remaining binding constants for Motor1 and Motor2 with Ketamine and Etomidate.

| | Ketamine | Etomidate |
|---|---|---|
| Motor1 | 39020M$^{-1}$ | 35318M$^{-1}$ |
| Motor2 | 193490M$^{-1}$ | 36812M$^{-1}$ |

For urine samples (Table 4), we took 0.1 mL from each urine sample and dried them under high vacuum. Then they were dissolved in 0.5 mL D$_2$O, and 0.1 mL of 60 mM reference solution (1,3,5-tricarboxylate benzene) was added. NMR spectra were taken and the concentration of Motor1 in urine was calculated from the ratio between the integration of diagnostic peak for reference (8.3 ppm, 3H) and Motor1 (1.9-1.5 ppm, 12H).

TABLE 4

| Sample No. | Urine volume (μL) | Integral * | [Motor1] (mM) | [Motor1] (mg/mL) | Mass (Motor1) (mg) | Notes |
|---|---|---|---|---|---|---|
| R1U | 930 | 3.34 | 6.958 | 10.723 | 9.972 | |
| R2U | 530 | 0.06 | 0.125 | 0.193 | 0.102 | Blood in urine |
| R3U | 580 | 10.25 | 21.354 | 32.907 | 19.086 | |
| R4U | 240 | 8.88 | 18.500 | 28.509 | 6.842 | Precipitate in urine |
| R5U | 1350 | 0.00 | 0.000 | 0.000 | 0.000 | |
| R6U | 415 | 0.00 | 0.000 | 0.000 | 0.000 | |
| R7U | 725 | 5.72 | 11.917 | 18.364 | 13.314 | |
| R8U | 610 | 13.78 | 28.708 | 44.240 | 26.986 | |
| R9U | 950 | 4.21 | 8.771 | 13.516 | 12.840 | |
| R10U | 315 | 8.70 | 18.125 | 27.931 | 8.798 | |
| R11U | 560 | 1.03 | 2.146 | 3.307 | 1.852 | |
| R12U | | | | | | N/A |
| R13U | 815 | 0.00 | 0.000 | 0.000 | 0.000 | |
| R14U | 355 | 10.62 | 22.125 | 34.095 | 12.104 | |
| R15U | 305 | 6.88 | 14.333 | 22.088 | 6.737 | Blood in urine |
| R16U | 455 | 12.28 | 25.583 | 39.424 | 17.938 | |
| R17U | 255 | 10.74 | 22.375 | 34.480 | 8.792 | |
| R18U | 610 | 0.00 | 0.000 | 0.000 | 0.000 | |
| R19U | 615 | 1.27 | 2.646 | 4.077 | 2.507 | Precipitate in urine |
| R20U | 190 | 5.39 | 11.229 | 17.304 | 3.288 | Precipitate in urine |
| R21U | 585 | 2.40 | 5.000 | 7.705 | 4.507 | |
| R22U | 390 | 0.00 | 0.000 | 0.000 | 0.000 | Precipitate in urine |

* Peak from 1.65-1.9 ppm, with reference peak integral for benzene-1,3,5-tricarboxylic acid (5 mM) at 8.3 ppm set to 3

EXAMPLE 5

Toxicity Studies:

To measure the cellular toxicity of Motor1 we use two complementary assays: an MTS (CellTiter 96 AQueous Kit®) assay that measures cellular metabolism, and a cytotoxicity assay (Toxilight® BioAssay Kit) that measures cell death via the release of the cytosolic enzyme adenylate kinase into the supernatant. Both assays were used with two different cell lines commonly used in drug toxicity studies, HEK293 and HepG2 cell lines. HEK293, a human kidney cell line, is used to assess the effect of the drug candidate on the renal system and HepG2, a human hepatocyte cell line, is used to assess the response of liver cells where drugs are metabolized. Both assays included the use of an untreated population, and cells treated with distilled water, erythromycin and erythromycin estolate. Erythromycin is a commercially available drug widely used to treat bacterial infections. Erythromycin estolate, however, is a derivative with high toxicity. Erythromycin, with an $EC_{50}$ value of 594 (±194) μM is significantly less toxic compared to erythromycin estolate, which has an $EC_{50}$ of 109 (±7) μM. These two drugs were chosen specifically to serve as a point of comparison for the levels of cytotoxicity resulting from Motor1.

Both cell lines were incubated with the containers (0.01, 0.1, 1 and 10 mM) for 2 days prior to analysis with the two assays. Relative absorbance and luminescence data was normalized to percent cell viability (MTS) and cell death (AK). For the MTS assay, the untreated cells were set at 100% cell viability while the cell population treated with distilled water was set at a 100% cell death for the AK assay.

Figure 27:
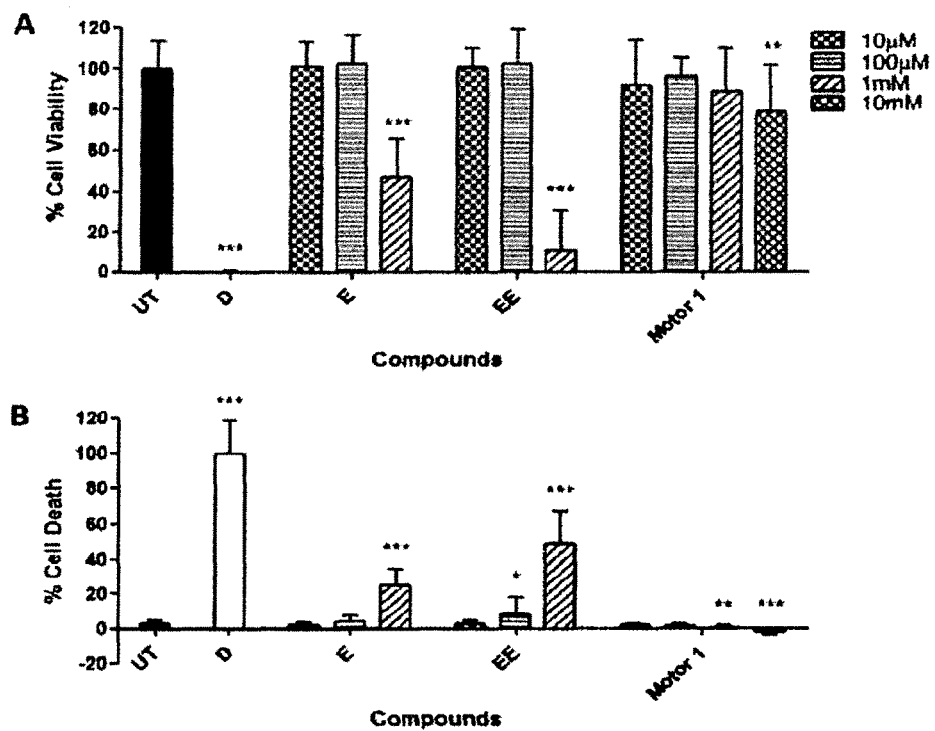
FIG. 27. Toxicology of Motor1 using the human kidney cell line HEK293. Results from (A) MTS assay (B) AK assay. Untreated population (UT), Distilled water (D), Erythromycin (E), Erythromycin Estolate (EE).

The MTS assay conducted on the HEK293 (FIG. 27A) cell line showed high cell survival in the all concentrations of Motor1 at 92, 96, 89 and 79% cell viability. However, cell populations treated with distilled water (0.2%), 1 mM of erythromycin (47%) and erythromycin estolate (11%) showed significant decrease in cell viability. The AK assay (FIG. 27B) performed on this cell line reflected these results. Percent cell death observed in the cells treated with 1 mM erythromycin and erythromycin estolate were 25 and 49% respectively. However, cell death in the untreated population and all concentrations of Motor1 was below 5%.

Figure 28:
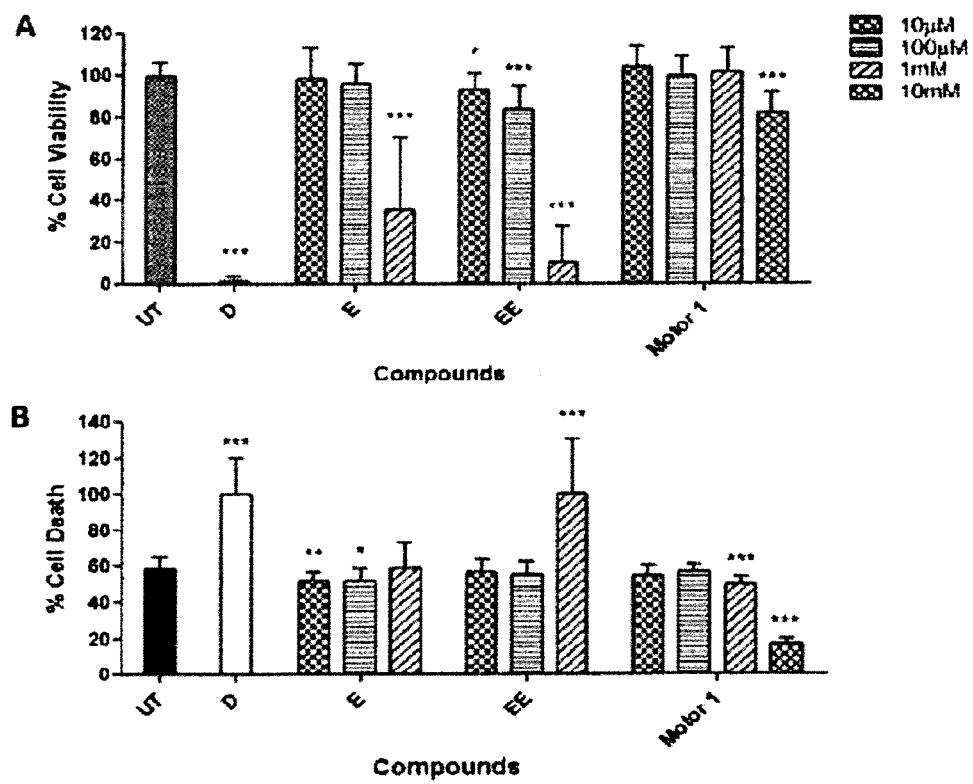
FIG. 28. Toxicology of Motor1 using the human liver cell line HepG2. Results from (A) MTS assay (B) AK assay. Untreated population (UT), Distilled water (D), Erythromycin (E), Erythromycin Estolate (EE).

Similar results were observed in the HepG2 cell line (FIG. 28). The HepG2 cells treated with increasing concentrations of Motor1 showed high cell viability at 104, 100, 102 and 82% respectively in the MTS assay (FIG. 28A). These results were comparable to cell viability observed in the untreated population. However, HepG2 cells treated with distilled water (1%), 1 mM erythromycin (36%) and erythromycin estolate (10%) showed significant decreases in cell viability. These results were confirmed in the AK assay (FIG. 28B) performed using the HepG2 cell line. High percentage of cell death was observed with samples treated with erythromycin estolate at 1 mM (100% cell death). HepG2 cells exhibited high background levels in this assay as indicated by the 60% cell death in the untreated population. All cell samples treated with increasing concentrations of Motor1 show low cytotoxicity (55, 56, 50 and 17% cell death) in comparison to the untreated samples.

Overall Motor1 was found to be non-toxic in both human kidney and liver cells up to a concentration of 10 mM.

Figure 29:
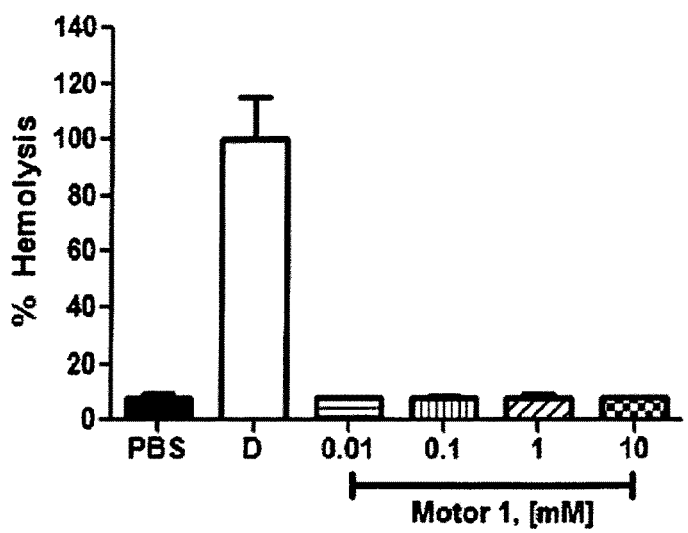
FIG. 29. Percent hemolysis at 3 h caused by increasing concentrations of the compound Motor1. Phosphate Buffer Saline (PBS), Distilled water (D).

A hemolysis assay (FIG. 29) was conducted to assess any toxic effects of Motor1 on human erythrocytes. These assays used pooled blood from two healthy donors from which red blood cells were isolated through centrifugation. Erythrocytes were exposed to phosphate buffered saline (PBS), distilled water, and increasing concentrations of Motor1 (1) (0.01, 0.1, 1 and 10 mM). The erythrocytes were incubated shaking at 37° C. for 3 h following treatment. The release of hemoglobin from damaged red blood cells was quantified by measuring the relative absorbance of the samples at 405 nm. Data collected was converted to percent hemolysis by setting the cell population treated with distilled water at a 100% hemolysis.

This assay showed that while erythrocytes treated with distilled water resulted in a high percentage of hemolysis, samples incubated with PBS, and increasing concentrations of Motor1 did not result in hemolysis above 20%. The hemolysis assay presented data towards the conclusion that the Motor1 is non-toxic to human erythrocytes up to a concentration of 10 mM.

Figure 30:
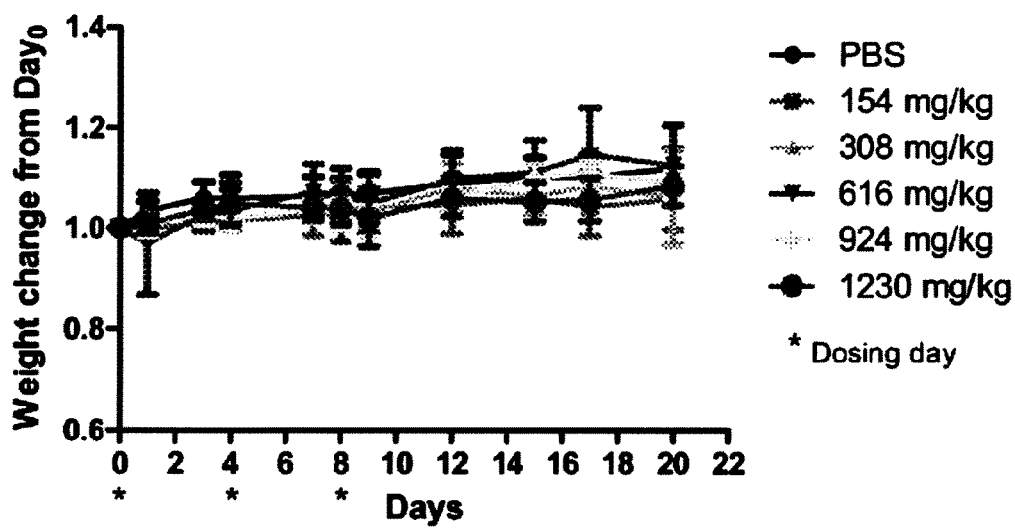
FIG. 30. Motor1 is well tolerated in mice. Indicated amounts of Motor1 were injected into the tail vein of outbred Swiss Webster mice at day 0, 4 and 8. The weight of each mouse was monitored over time and there were 5 mice per experimental group.
Figure 31:
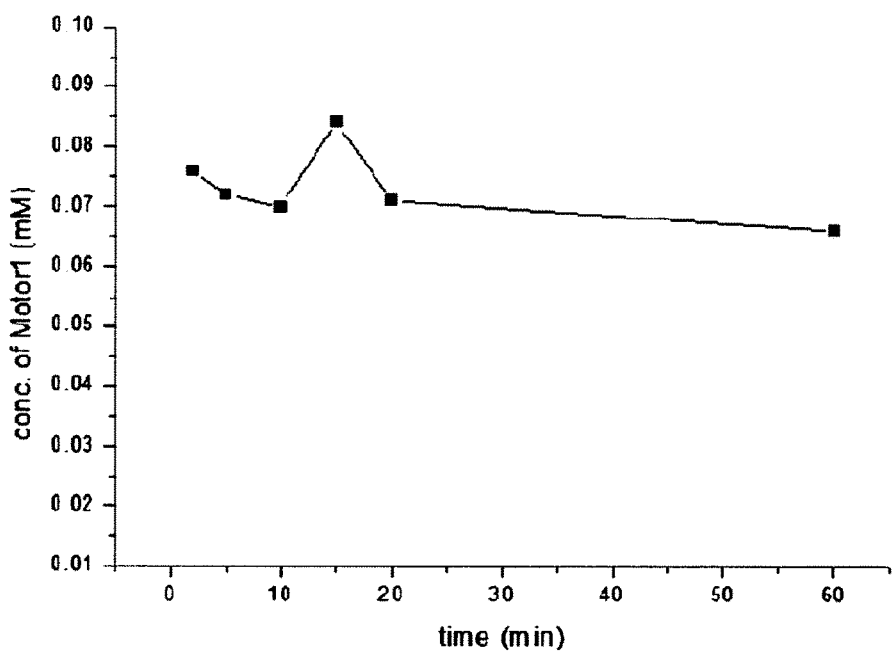
FIG. 31. An example of a plot of concentration (mM) of Motor1 in plasma versus time (min) plot for Rat 17.
Figure 32:
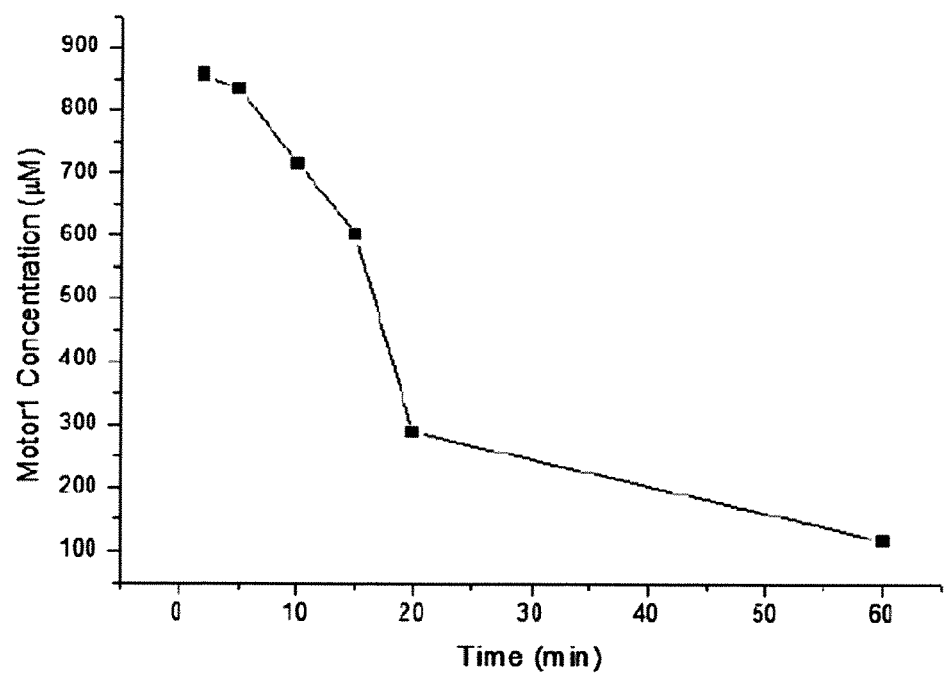
FIG. 32. An example of a plot of concentration (mM) of Motor1 in plasma versus time (min) plot for Rat 10.
Figure 33:
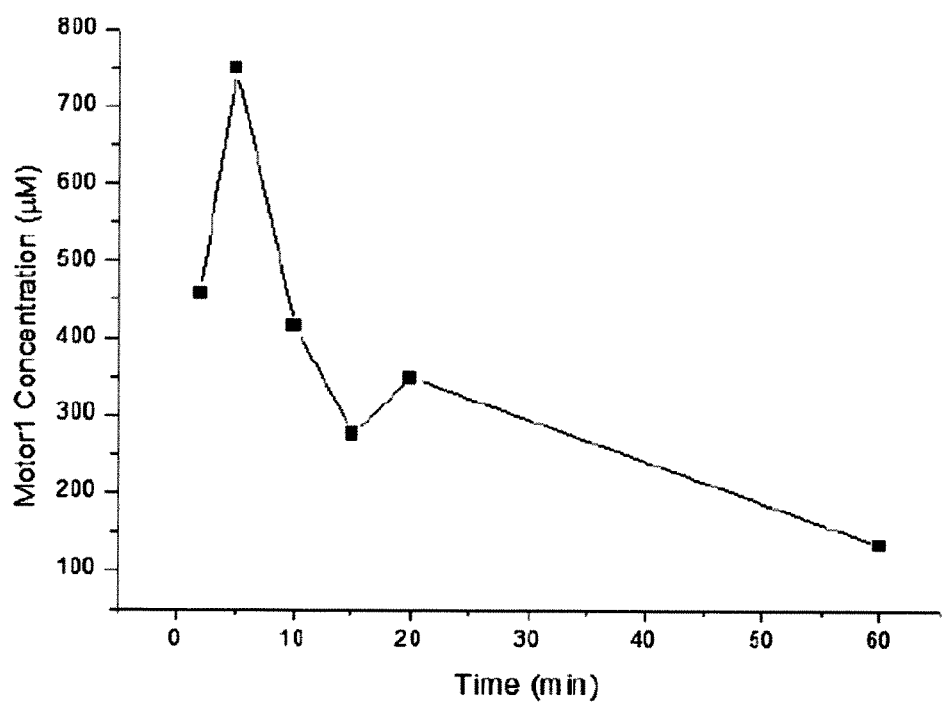
FIG. 33. An example of a plot of concentration (mM) of Motor1 in plasma versus time (min) plot for Rat 11.
Figure 34:
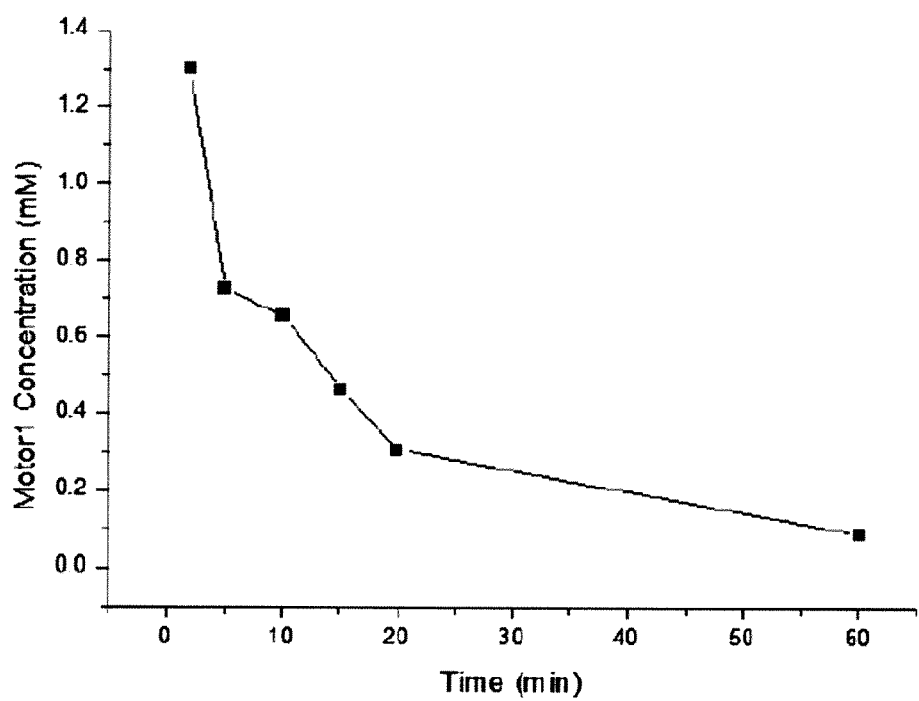
FIG. 34. An example of a plot of concentration (mM) of Motor1 in plasma versus time (min) plot for Rat 21.

FIG. 30 shows Motor1 is well tolerated in mice. Indicated amounts of Motor1 were injected into the tail vein of outbred Swiss Webster mice at day 0, 4 and 8. The weight of each mouse was monitored over time and there were 5 mice per experimental group.

For Plasma samples, four rats in total have been tested: Rat 10, Rat 17, Rat 11, Rat 21. For each plasma sample, 10 µL of plasma was taken and dried under high vacuum. Excess amount of probe solution was added (495 µL of 38 µM p-xylenediamine) to dissolve the residue and then the reference (5 µL of 600 µM benzene-1,3,5-tricarboxylic acid) was added. NMR spectra was taken with water suppression and the concentration of Motor1 was calculated from the ratio between the integrations of the peaks for the reference (8.2 ppm, 3H) and Motor1 (6.5 ppm, 4H). For Rat 17, benzene-1,3,5-tricarboxylic acid was not used, but p-xylenediamine was used as the reference (FIGS. 31-34).

Figure 35:
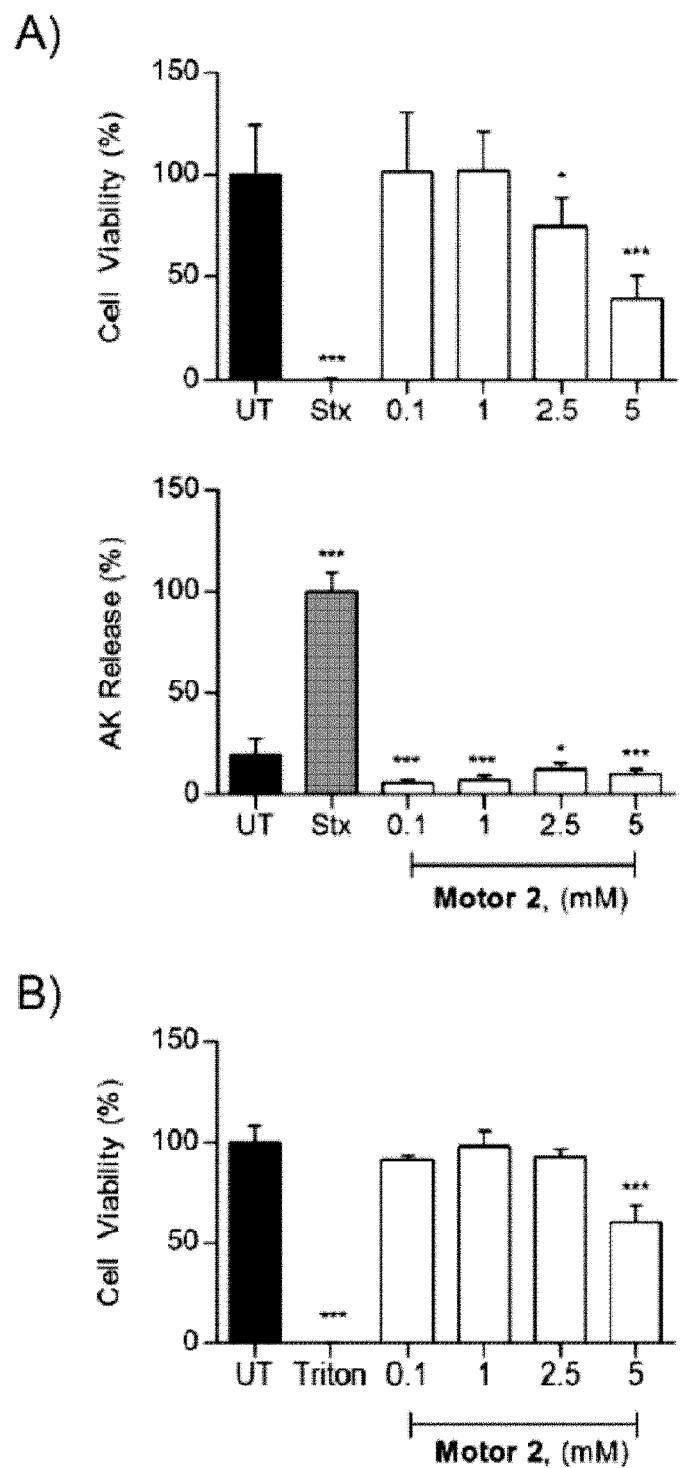
FIG. 35. Varying concentrations of Motor2 incubated with THP-1 (A) and HEK 293 (B) cells over a 48 hr period resulted in high cell survival up to 5 mM. Two complementary assays were used to analyze toxicology an MTS and an AK release assay for the THP-1 cells. The AK release assay was conducted using 20 μL of supernatant from each sample studied using the MTS assay. The Vialight assay was used to assess cell viability in the HEK 293 cells. (UT=Untreated, Stx=Staurosporine, Triton=Trition-X-100). Unpaired t-test analysis was used with *P=0.01-0.05; P=0.001-0.01; *P,0.001 for the statistical analysis of all figures presented.
Figure 36:
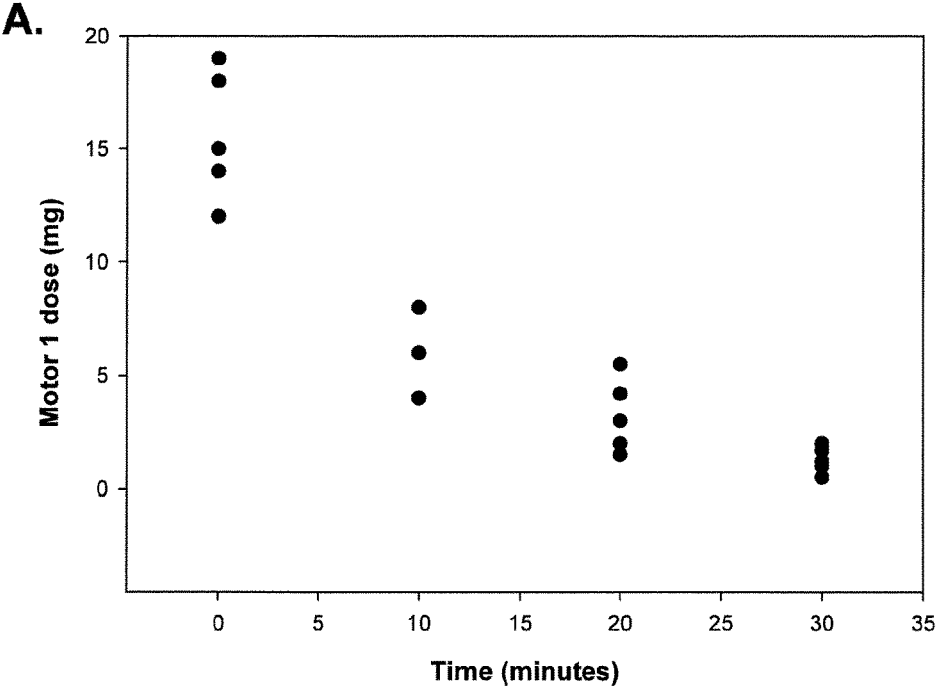
FIG. 36. Time to complete recovery of muscle strength following Motor1 injection. Dose-response relationship of Motor1 to reverse rocuronium. A: time to recovery of muscle strength to baseline as a function of Motor1 dose. B: Probit-transformed dose, line: linear regression. The data show a predictable dose-response relationship.
Figure 36:
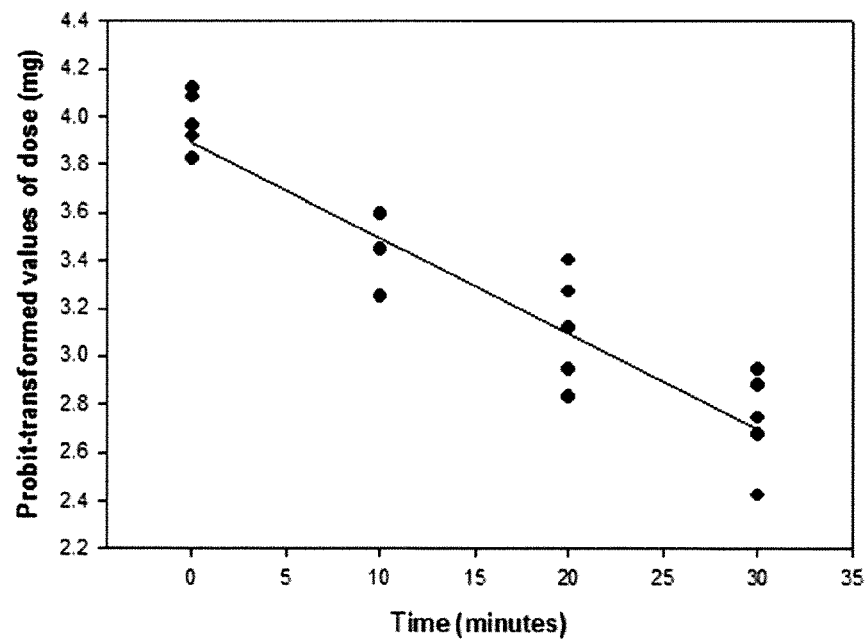
Figure 37:
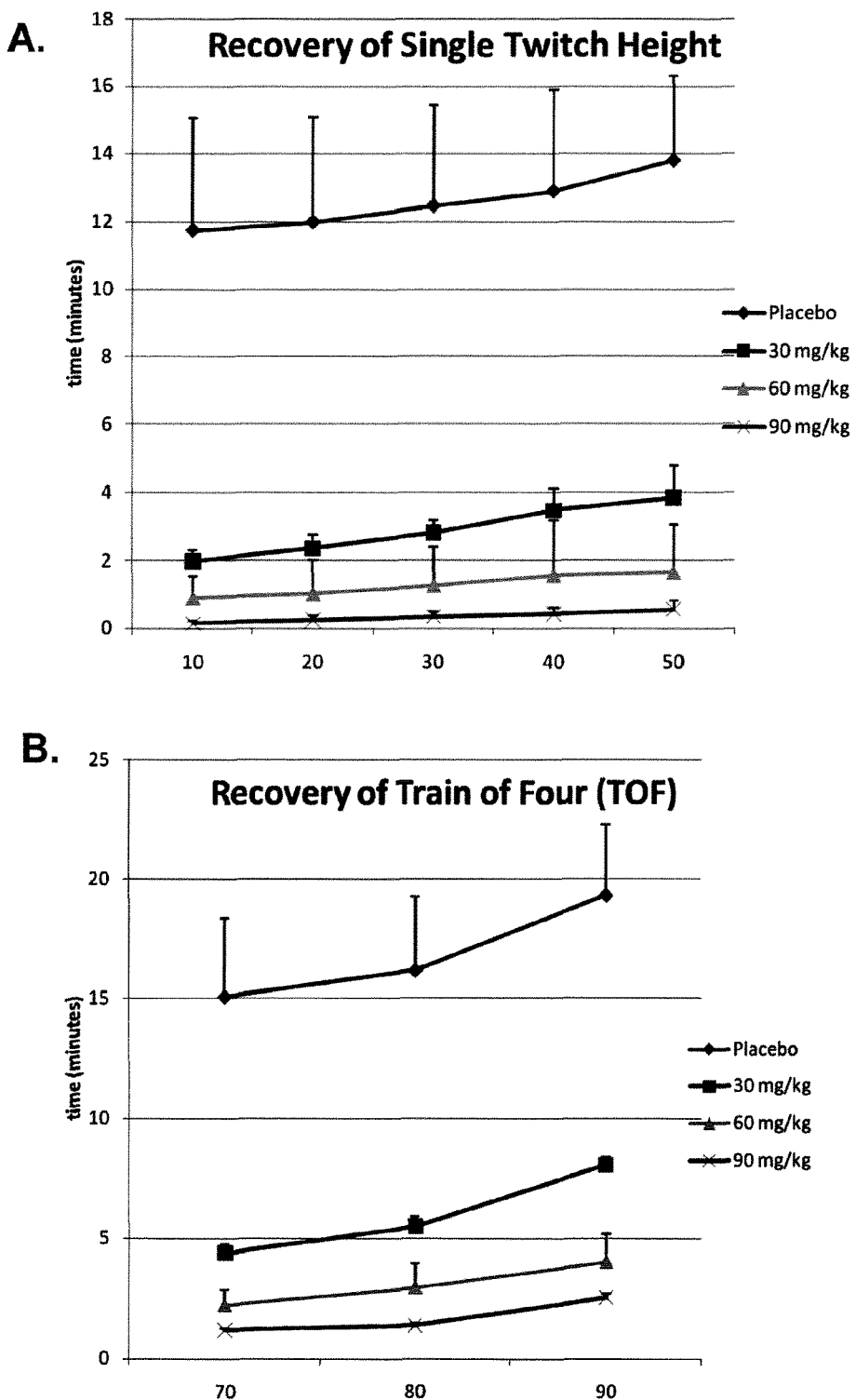
FIG. 37. Time to recovery of twitch height (A) and train-of-four ratio (B) following complete rocuronium-induced neuromuscular block. Recovery profile is shown in response to different Motor1 doses and placebo. Mean time to recovery of the twitch height to 90% following Motor2 (90 mg) versus placebo amounted to 2.5 versus 19 minutes.
Figures 38, 39:
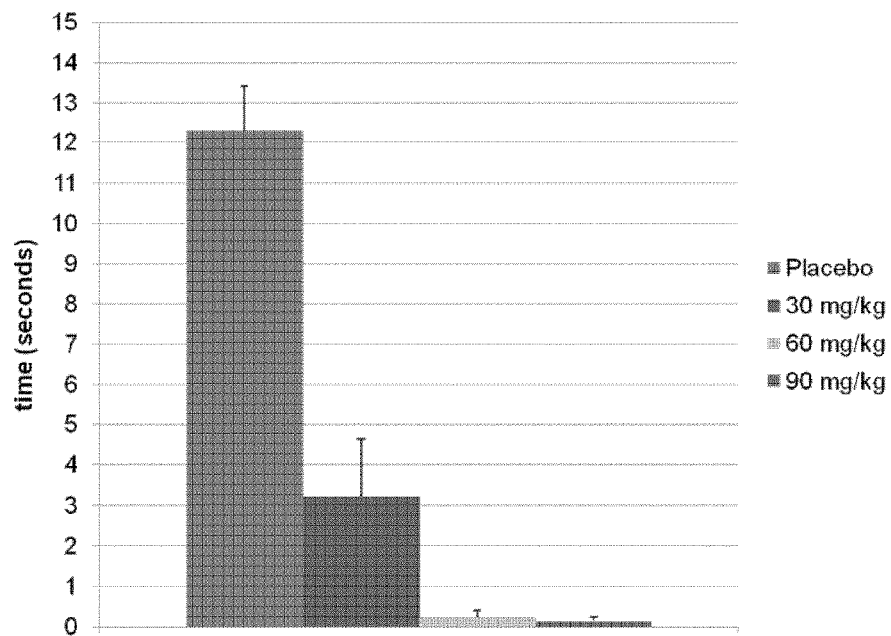
FIG. 38. Time to recovery of spontaneous breathing following complete rocuronium-induced neuromuscular block. Recovery time is given in response to different Motor1 doses and placebo. Mean recovery of spontaneous breathing amounted to 10 seconds after Motor1 versus 723 seconds following Motor1 90 mg.
FIG. 39. Arterial Blood Gas Parameters before and after application of Motor1: Safety of Motor1 given during steady state isoflurane anesthesia (which cannot be reversed by Motor1)—respiratory: pH, pCO$_2$, and pO$_2$ did not change following Motor1 injection FIG. 40. Blood Pressure and Heartrate during and After Application of Motor1: Safety of Motor1 during steady state isoflurane anesthesia—cardiovascular: heart rate and mean arterial blood pressure did not change.
Figure 40:
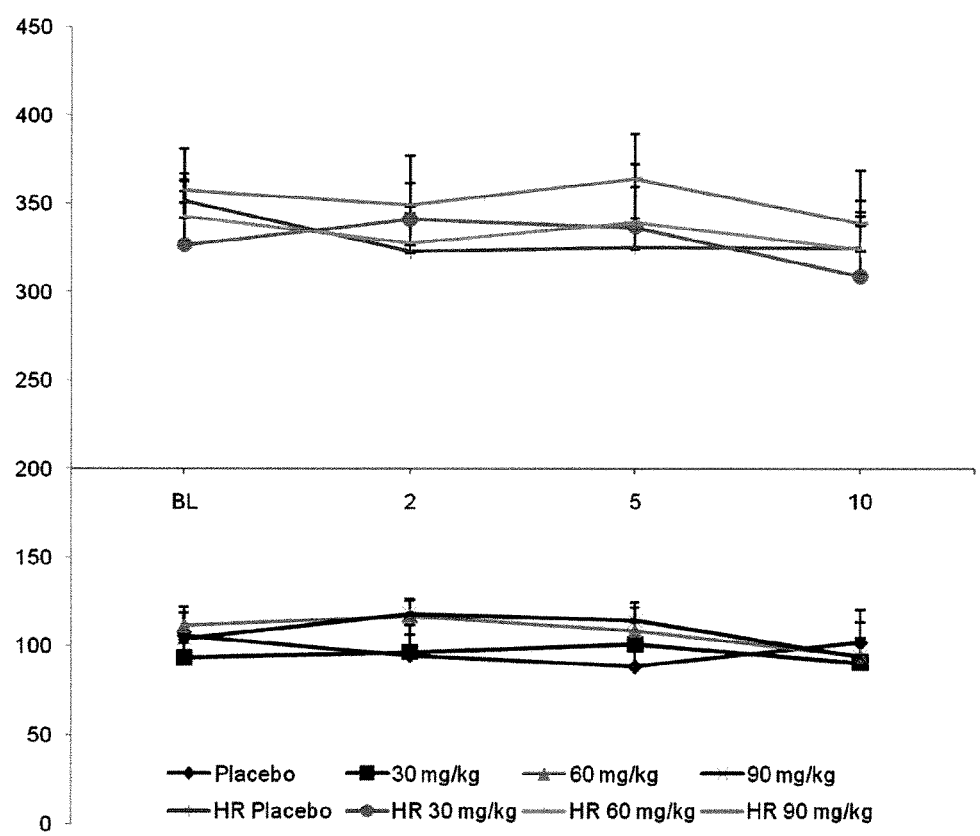
Figure 41:
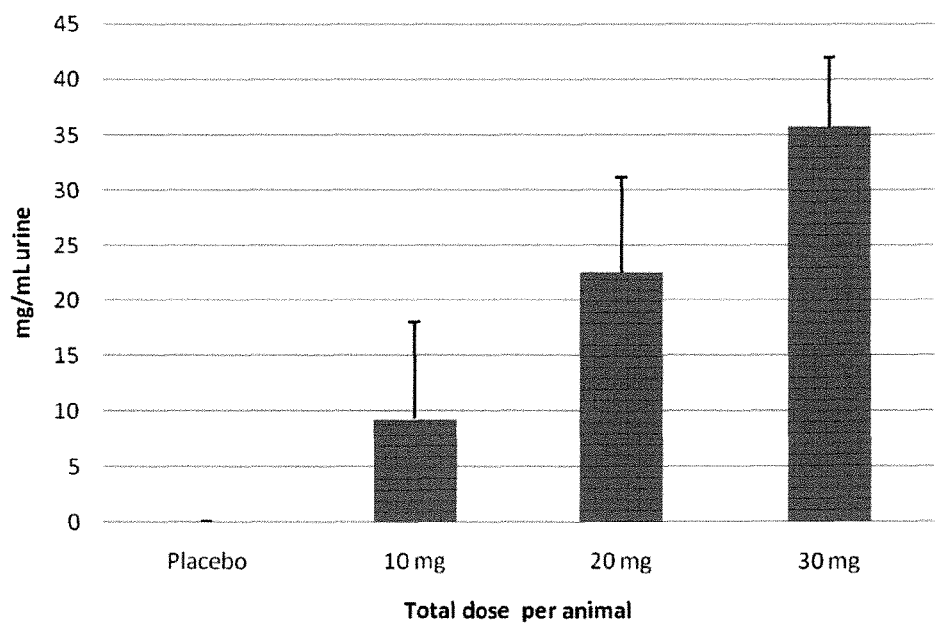
FIG. 41. Elimination of Motor1: Motor1 is eliminated in urine. Two hours after Motor1 injection, Motor1 concentration in the urine equals concentration in the plasma.
Figure 42:
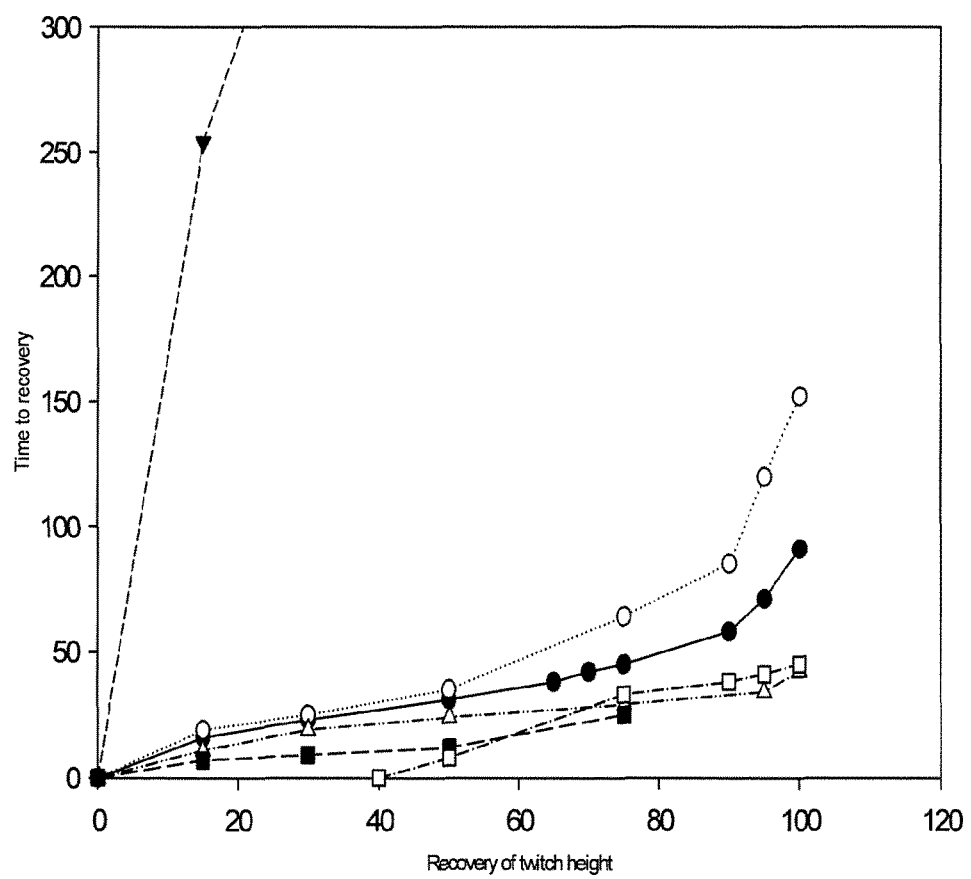
FIG. 42. Time to recovery of twitch height following complete cisatracurium-induced neuromuscular block. Recovery profile is shown in response to different Motor1 and Motor2 doses. Note that low-dose Motor2 reverses the benzylisoquinolinum cisatracurium faster than high-dose 1.
Figure 43:
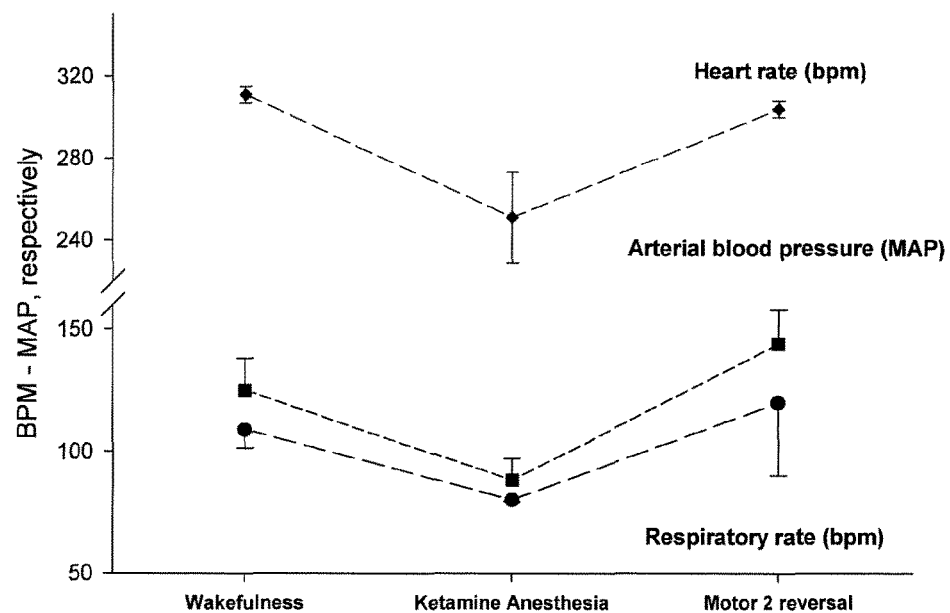
FIG. 43. Effects of ketamine and its reversal on respiratory and cardiovascular function.
Figure 44:
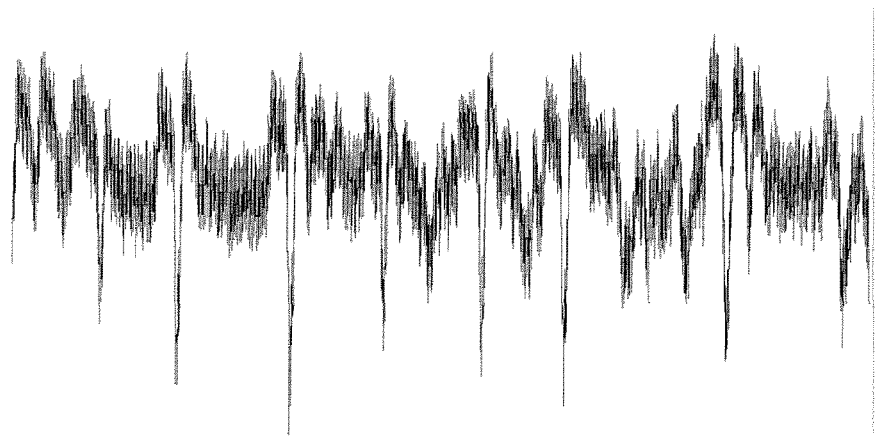
FIG. 44. Electroencephalogram (EEG) during ketamine anesthesia.
Figure 45:
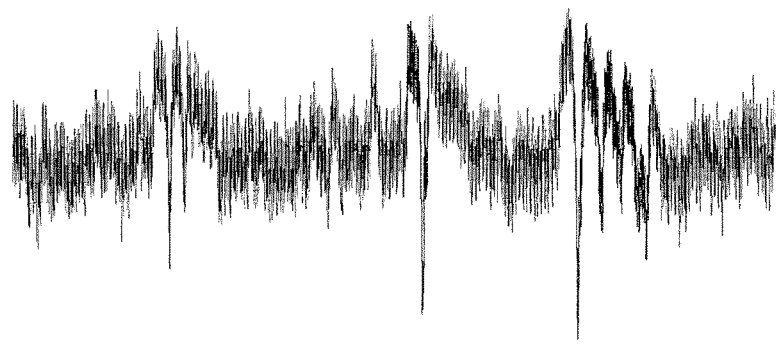
FIG. 45. EEG following Motor2 reversal of ketamine anesthesia.

FIG. 35 shows toxicology using Motor2. Varying concentrations of Motor2 were incubated with THP-1 (A) and HEK 293 (B) cells over a 48 hr period resulted in high cell survival up to 5 mM. Two complementary assays were used to analyze toxicology: an MTS and an AK release assay for the THP-1 cells. The AK release assay was conducted using 20 ul of supernatant from each sample studied using the MTS assay. The Vialight assay was used to assess cell viability in the HEK 293 cells. (UT=Untreated, Stx=Staurosporine, Triton=Trition-X-100). Unpaired t-test analysis was used with *P=0.01-0.05; P=0.001-0.01; *P,0.001 for the statistical analysis of all figures presented.

EXAMPLE 6

Deaths from drug overdose have been rising steadily over the past two decades and have become the leading cause of injury death in the United States. In 2011, 33,071 (80%) of the 41,340 drug overdose deaths in the United States were unintentional, 5,298 (12.8%) were of suicidal intent, 80 (0.2%) were homicides, and 2,891 (7%) were of undetermined intent. In 2011, drug misuse and abuse caused about 2.5 million emergency department (ED) visits. Of these, more than 1.4 million ED visits were related to pharmaceuticals. The present disclosure provides compositions and methods for addressing these circumstances. In particular, this Example includes in vitro and in vitro data demonstrating utility of compounds of the present disclosure for reversal of the effects of a variety of drugs and includes in vitro and in vivo data supporting this utility. In this regard, use of molecular containers of the present disclosure as reversal agent to reverse toxic effects of drugs of abuse (cocaine or any other opiate, amphetamines, ketamine, methamphetamine, phencyclidine [PCP]) as well as drugs used in perioperative medicine (local anesthetics, beta-blockers, neurolepts, anticholinergic agents), as well as antidepressants will be apparent. It is expected this approach will have life-saving properties as far as toxicology is concerned in acute care settings. In addition, in a chronic setting, the compound(s) will be used as a drug that will significantly decrease the relapse rate in addiction.

In more detail, we have developed a reversal agent to reverse toxic effects of drugs of abuse (including but not necessarily limited to cocaine, amphetamines, ketamine, methamphetamine, phencyclidine [PCP]) as well as drugs used in perioperative medicine (local anesthetics, beta-blockers, neuroleptics, anticholinergic agents, opioids), as well as antidepressants. Compounds of this disclosure will be administered in acute care settings to treat the effect of acute intoxication. In addition, in a chronic setting, the compound can be used as treatment for cocaine, methamphetamine and other substance use disorders (SUD), as by rapidly inactivating the drug from the bloodstream, it will significantly decrease the relapse rate in addiction disorders, therefore leading to significant beneficial health-care economic implications.

In non-limiting embodiments, one or more compounds of the invention and/or compositions, such as pharmaceutical preparations comprising them, are suitable for use in reversal of acute intoxication from agents including but not necessarily limited to cocaine, amphetamines, ketamine, ecstasy, propranolol, atropine, lidocaine, bupivacaine, other local anesthetics, tricyclics antidepressant, and from intoxication by any members of the classes of drugs into which the foregoing compounds fall.

The present disclosure includes use of the compounds and compositions of the disclosure for any one or combinations of the following indications, which are illustrative and not meant to be limiting:

Treatment of Suicide Attempts or Accidental Overdoses by Drugs Such as Tricyclic Antidepressants, Beta-Blockers, and Opioids.

Cardiovascular and neurological symptoms of tricyclic antidepressants include arterial hypotension, cardiac arrhythmia, hallucinations, and seizures, and apnea. Sometimes, a combination of these drugs is given which can all be reversed by compounds of this disclosure which will be administered by paramedics and in the emergency departments.

Unintentional Illicit Drug Overdose.

Acute cocaine intoxication causes diffuse CNS excitation, land among the most dangerous complication it causes life-threatening hyperthermia, and severe cardiovascular effects, including coronary vasospasm and tachyarrhythmia, that are associated with significant morbidity and mortality. There is currently no antidote available for cocaine intoxication and the treatment is only supportive. Similar toxic symptoms are produced by ketamine, amphetamine and ecstasy intoxication. Ketamine abuse is closely associated worldwide with the use of other "club drugs" including "ecstasy" (3,4-ethylenedioxymethamphetamine or MDMA), and methamphetamine Opioids induce a respiratory depression and often, opioids and cocaine are administered in the same patient. The new drug will be administer as rapid antidote for the acute intoxication even in absence of clear information about which drugs were taken by the patient, or in case of suspected intoxication presented with acute psychotic symptoms.

Intoxication in Perioperative Medicine.

Large quantities of local anesthetics (e.g., bupivicaine, lidocaine, and other related drugs) are routinely injected into patients to provide regional anesthesia and analgesia necessary for various dental and surgical procedures. While generally safe, local anesthetic agents can be toxic if used in excessive doses or administered improperly. Accidental intravascular injection into an artery or vein, a known complication, can result in muscle twitching, grand mal seizure (1 to 4 per 1000 anesthetics), coma/unconsciousness, respiratory arrest, myocardial depression, myocardial conduction abnormalities, and cardiovascular collapse (Brown, D L, et al. (1995) Anesth Analg; Weinburg, G L (2012) Anesthesiology). Even when administered properly, patients may still experience unintended reactions to local anesthetics due to excessive drug absorption from the tissues into the blood. Compounds of this disclosure will be administered systemically to patients suffering local anesthetic toxicity to both sequester the local anesthetic drug and to potentially facilitate its clearance from the body. Animal studies and human case reports have shown intralipid administration, a potential local anesthetic "sink", to show some efficacy in reversing cardiac symptoms, validating this general approach to treating local anesthetic toxicity (Weinburg, G L (2012) Anesthesiology).

Cocaine/Amphetamine Relapse Prevention.

According to SAHMSA (substance Abuse and Mental Health Services Administration) in 2010 there were in US approximately 1.5 million of cocaine users and half million of metamphetamine users. Currently there is no treatment that is FDA-approved for the treatment of those addiction disorders. Compounds of this disclosure will be administered chronically to patients seeking treatment for their substance use disorder, and it will rapidly inactivate cocaine or metamphetamine such that the user does not experience the desired psychotropic effects, therefore reducing the drug addicting potential for the subject. There is experimental evidence suggesting that decreasing the amplitude and the rate of rise of a cocaine 'spike' substantially decreases the self-administration of the addictive substance Neuropsychopharmacology (2014) 39, 1538-1546.

As described in more detail below, in this Example we tested the ability of the molecular containers shown in FIG. 46 of this Example (Motor 1 a.k.a Calabadion 1; Motor2 a.k.a Calabadion 2; cucurbit[7]uril, sulfonated calix[4]arene, hexyl capped Motor 1) to bind to five important drugs of abuse, namely cocaine hydrochloride, methamphetamine hydrochloride, phencyclidine hydrochloride, ketamine hydrochloride, and morphine sulfate pentahydrate) to assess their potential use in the stated application areas. Cucurbit [7]uril, sulfonated calix[4]arene are known in the art and can be used in methods of this disclosure. In embodiments a compound of this disclosure comprises a hexyl cap.

We also tested the binding of Motor2 toward a wide variety of drugs as part of its development as a reversal agent for neuromuscular block, including but not limited to propranolol, atropine, lidocaine, bupivacaine, and imipramine.

In arriving at the present disclosure, ACCBs calabadion 1 and 2 were administered to more than 200 tracheostomized, mechanically ventilated rats, which reversed complete atonia of all skeletal muscles within 10-60 seconds (after administration of 5 mg/kg), and in a dose-dependent fashion (see Hoffmann et al; Anesthesiology. 2013 August; 119(2): 317-25, Angew Chem Int Ed Engl. 2012 Nov. 5; 51(45): 11358-62). ACCB did not have any side effects on: arterial blood-gas analysis, EKG, arterial blood pressure, and heart rate. The ames test was negative, and a total dose of up to 2 g given in escalating dose experiments (final dose: 1 g) was well tolerated. We have taken blood and urine samples from all rats and are have observed renal elimination of the compound. We did not observe any evidence of allergic actions and/or adverse effects on coagulation. We have measured the in-vitro binding affinity of calabadion 2 to cocaine•HCl $(1.0\pm0.1)\times10^6$, methamphetamine $(4.3\pm1.0)\times10^6$, phencyclidine $(2.1\pm0.1)\times10^5$, ketamine $3.7\times10^4$, and morphine ($Ka=5.3\times10^5$ $M^{-1}$ (Ka values in units 1/Molar). We have shown that calabadion 2 clinically reverses the effects of ketamine. In a total of 12 experiments in rats ketamine 20 mg/kg bolus was given followed by an infusion of calabadion versus placebo. Calabadion 2 reduced the time to recovery of righting reflex by more than 40 percent.

Figure 46:
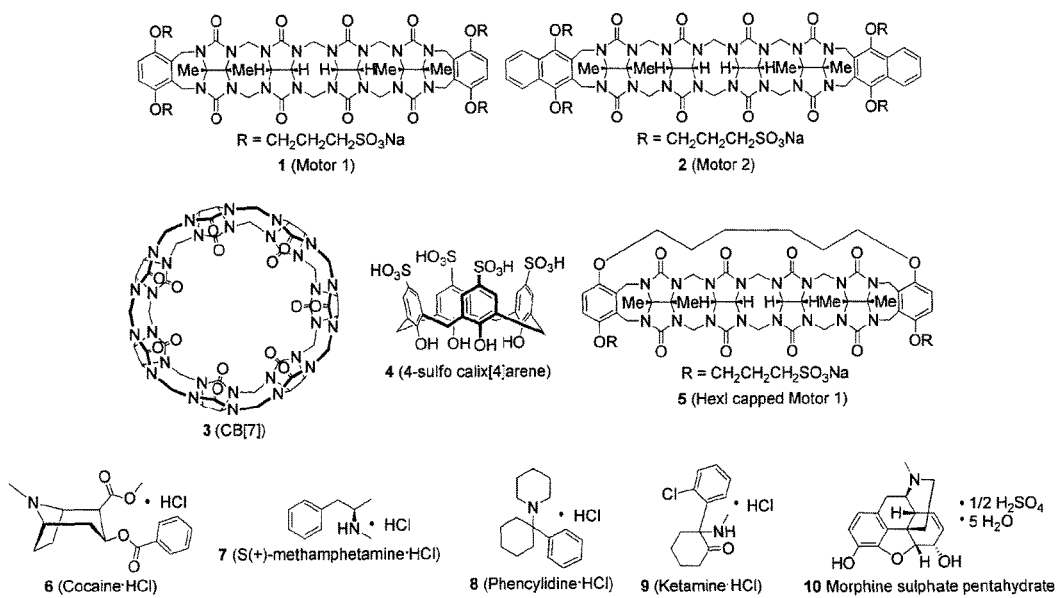
FIG. 46. Structures of molecular containers Motor1, Motor2, CB[7], 4-sulfo calix[4]arene, and hexyl capped Motor1 and drugs of abuse cocaine, S(+)-methamphetamine, phencyclidine, ketamine, and morphine.
Figure 47:
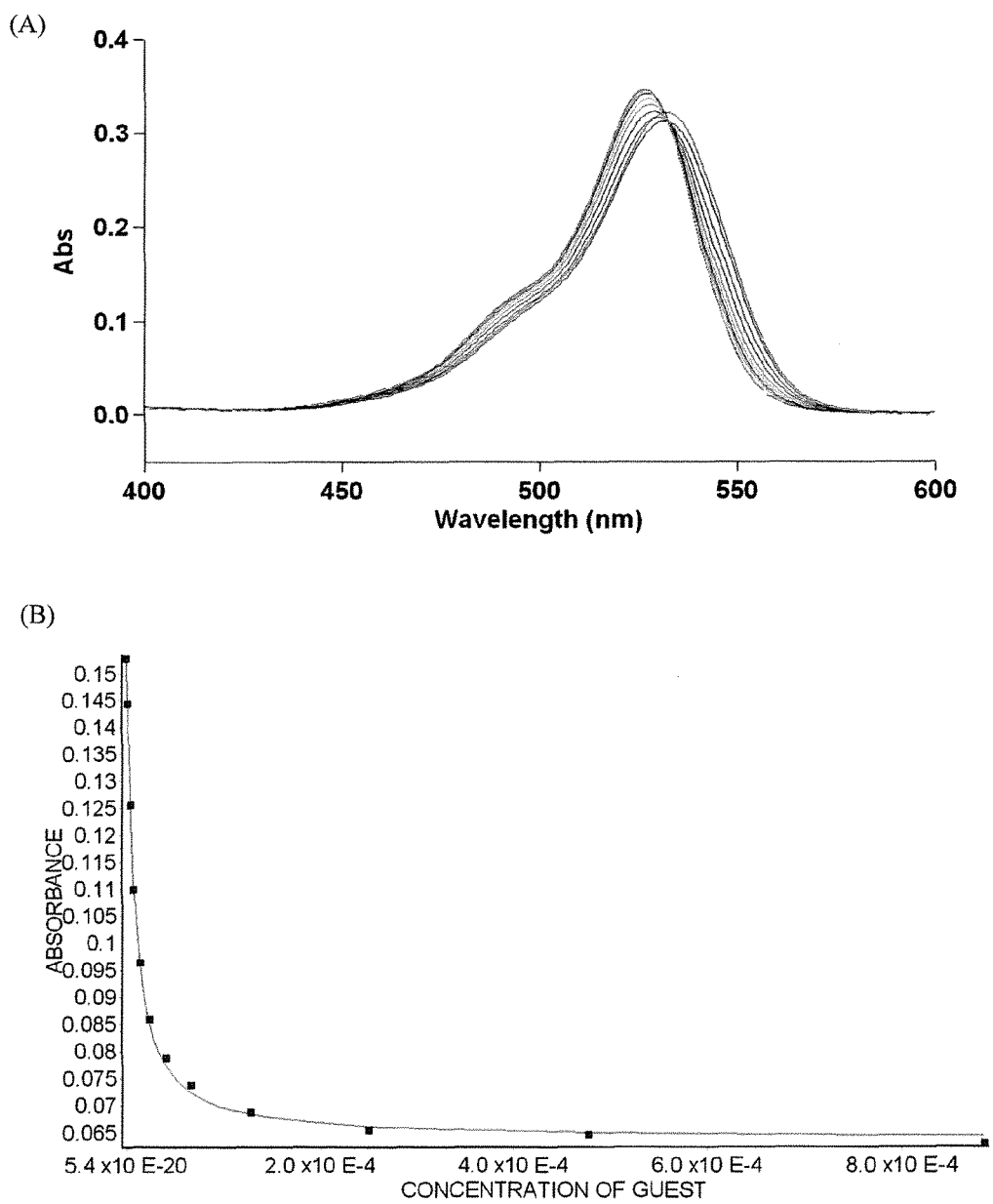
FIG. 47. (A) UV/Vis spectra from the titration of Motor 1 (5.02 μM) and rhodamine 6G (4.97 μM) with cocaine (0-885 μM) in 20 mM NaH$_2$PO$_4$ buffer (pH=7.4); (B) plot of the $A_{550}$ as a function of cocaine concentration. The solid line represents the best non-linear fit of the data to a competitive binding model ($K_a$=(6.6±0.4)×10$^5$ M$^{-1}$).
Figure 48:
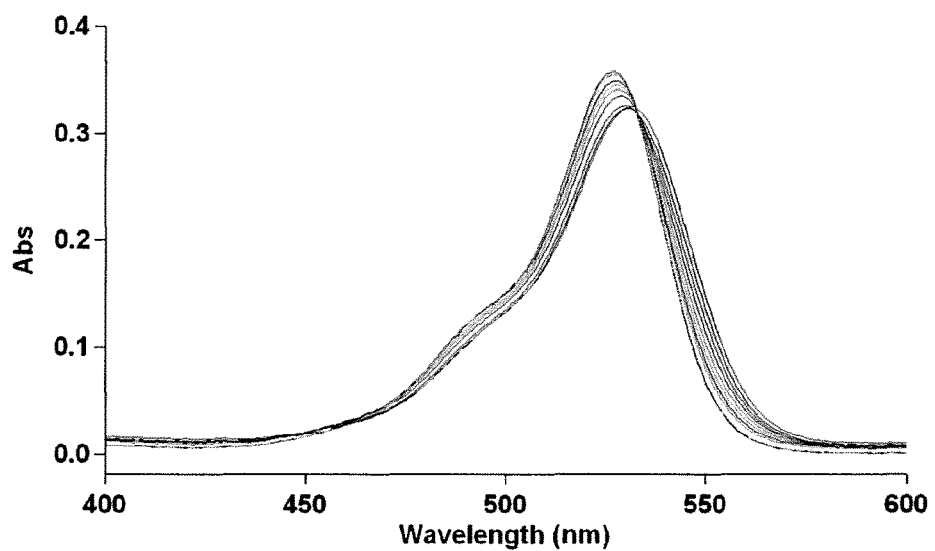
FIG. 48. (A) UV/Vis spectra from the titration of Motor 2 (4.97 μM) and rhodamine 6G (4.97 μM) with cocaine (0-745.1 μM) in 20 mM NaH$_2$PO$_4$ buffer (pH=7.4); (B) plot of the $A_{550}$ as a function of cocaine concentration. The solid line represents the best non-linear fit of the data to a competitive binding model ($K_a$=(1.0±0.1)×10$^6$ M$^{-1}$).
Figure 48:
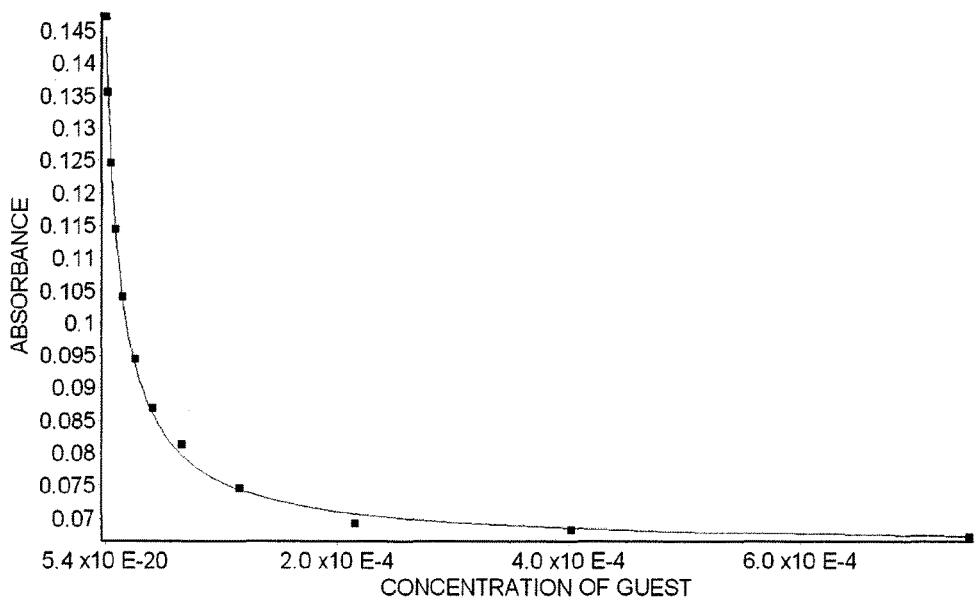
Figure 49:
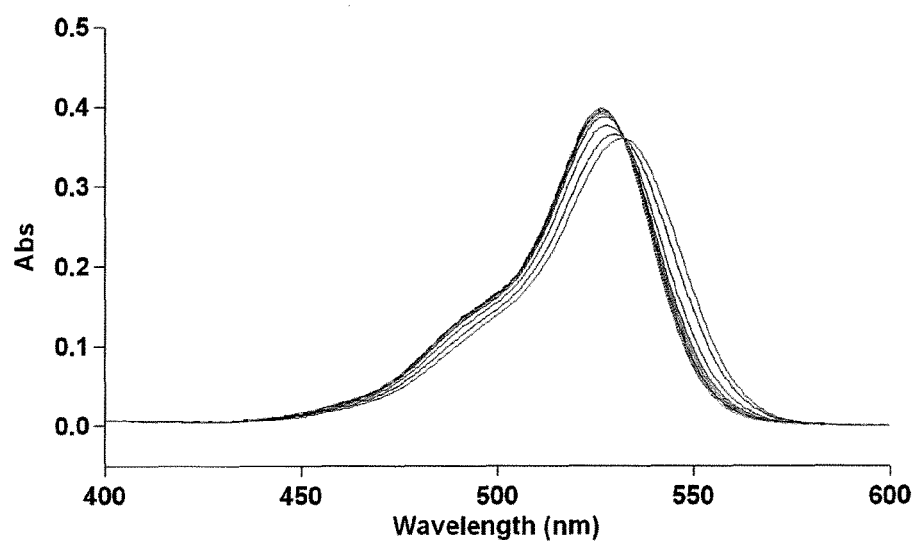
FIG. 49. (A) UV/Vis spectra from the titration of Motor 1 (5.02 μM) and rhodamine 6G (4.97 μM) with methamphetamine (0-581 μM) in 20 mM NaH$_2$PO$_4$ buffer (pH=7.4); (B) plot of the $A_{550}$ as a function of methamphetamine concentration. The solid line represents the best non-linear fit of the data to a competitive binding model ($K_a$=(7.5±2.9)×10$^6$ M$^{-1}$).
Figure 49:
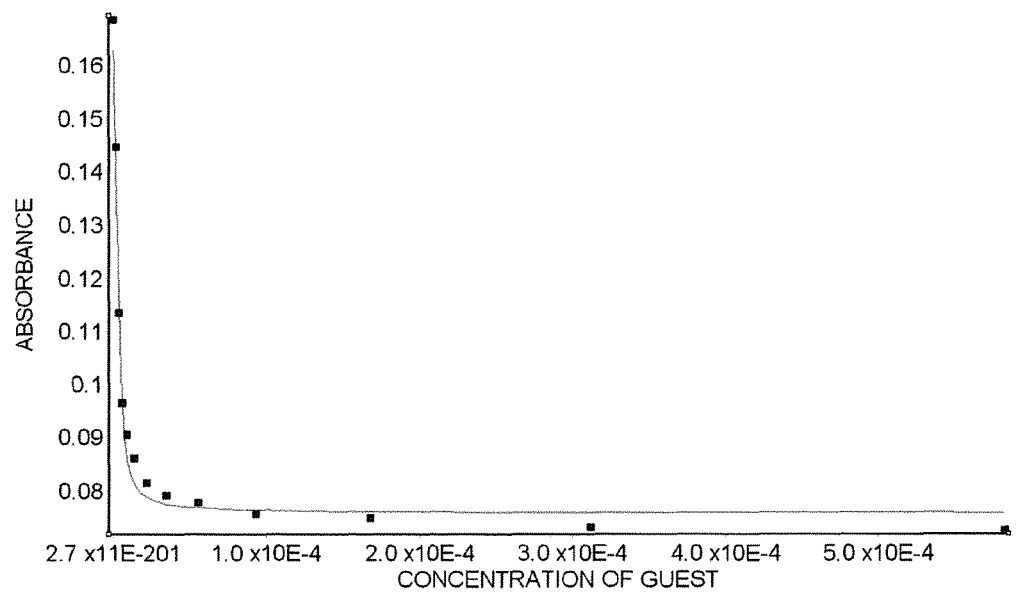
Figure 50:
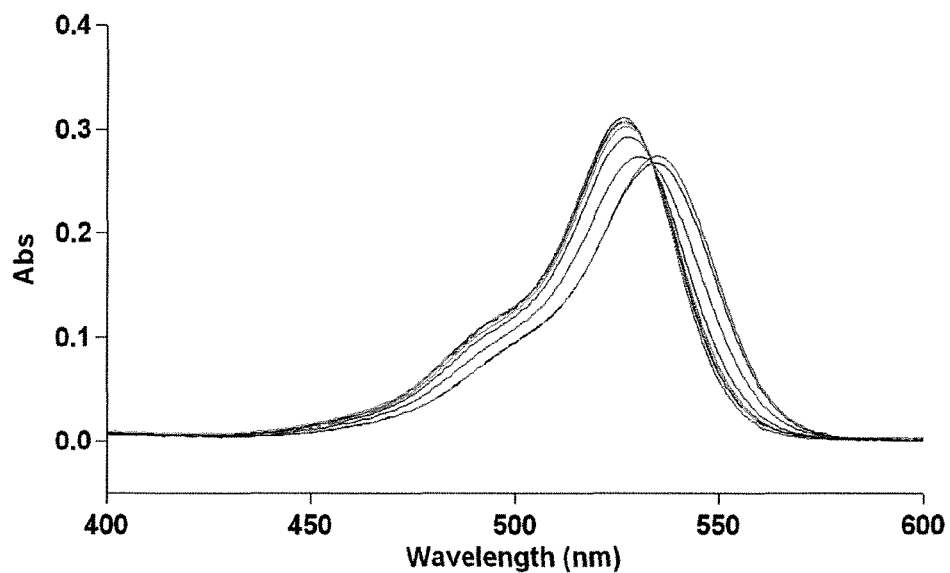
FIG. 50. (A) UV/Vis spectra from the titration of Motor 2 (4.97 μM) and rhodamine 6G (4.97 μM) with methamphetamine (0-219 μM) in 20 mM NaH$_2$PO$_4$ buffer (pH=7.4); (B) plot of the $A_{550}$ as a function of methamphetamine concentration. The solid line represents the best non-linear fit of the data to a competitive binding model ($K_a$=(4.3±1.0)×10$^6$ M$^{-1}$).
Figure 50:
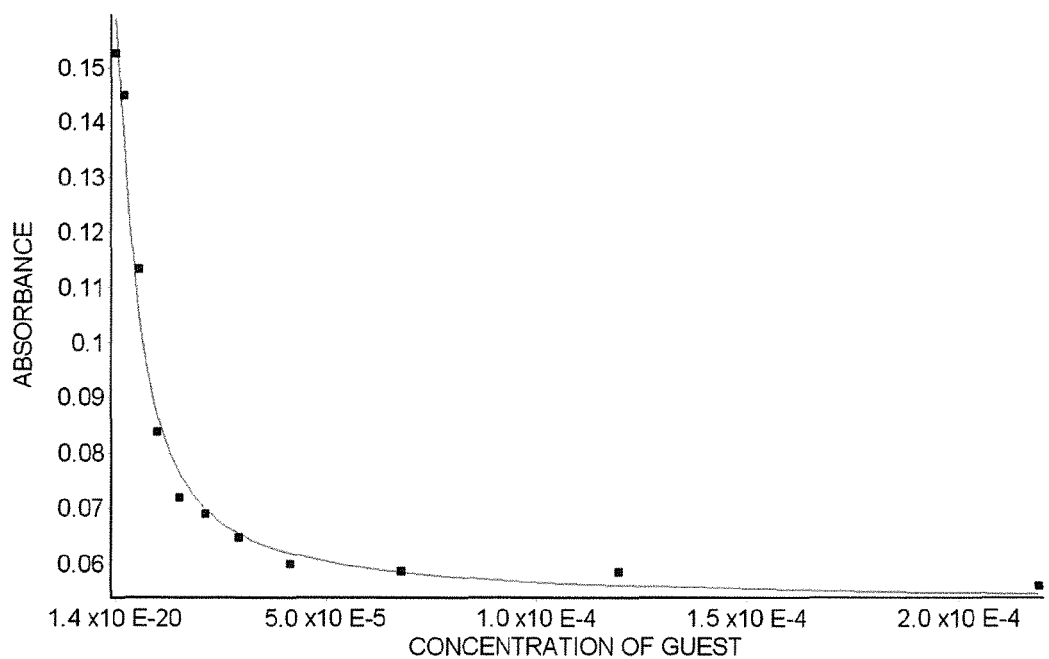
Figure 51:
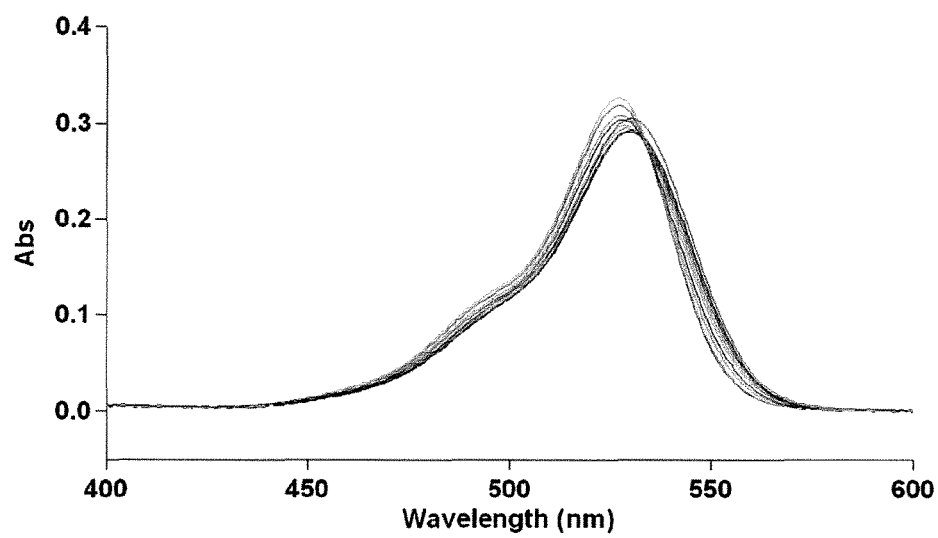
FIG. 51. (A) UV/Vis spectra from the titration of Motor 1 (5.02 μM) and rhodamine 6G (4.97 μM) with phencyclidine (0-1.616 mM) in 20 mM $NaH_2PO_4$ buffer (pH=7.4); (B) plot of the $A_{550}$ as a function of phencyclidine concentration. The solid line represents the best non-linear fit of the data to a competitive binding model ($K_a=(4.7\pm0.5)\times10^4$ $M^{-1}$).
Figure 51:
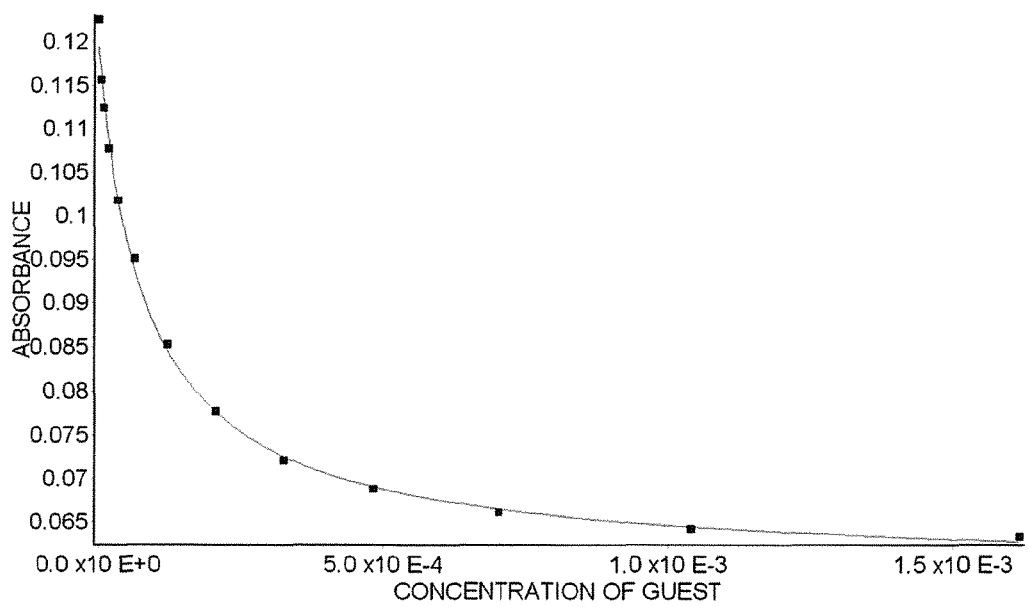
Figure 52:
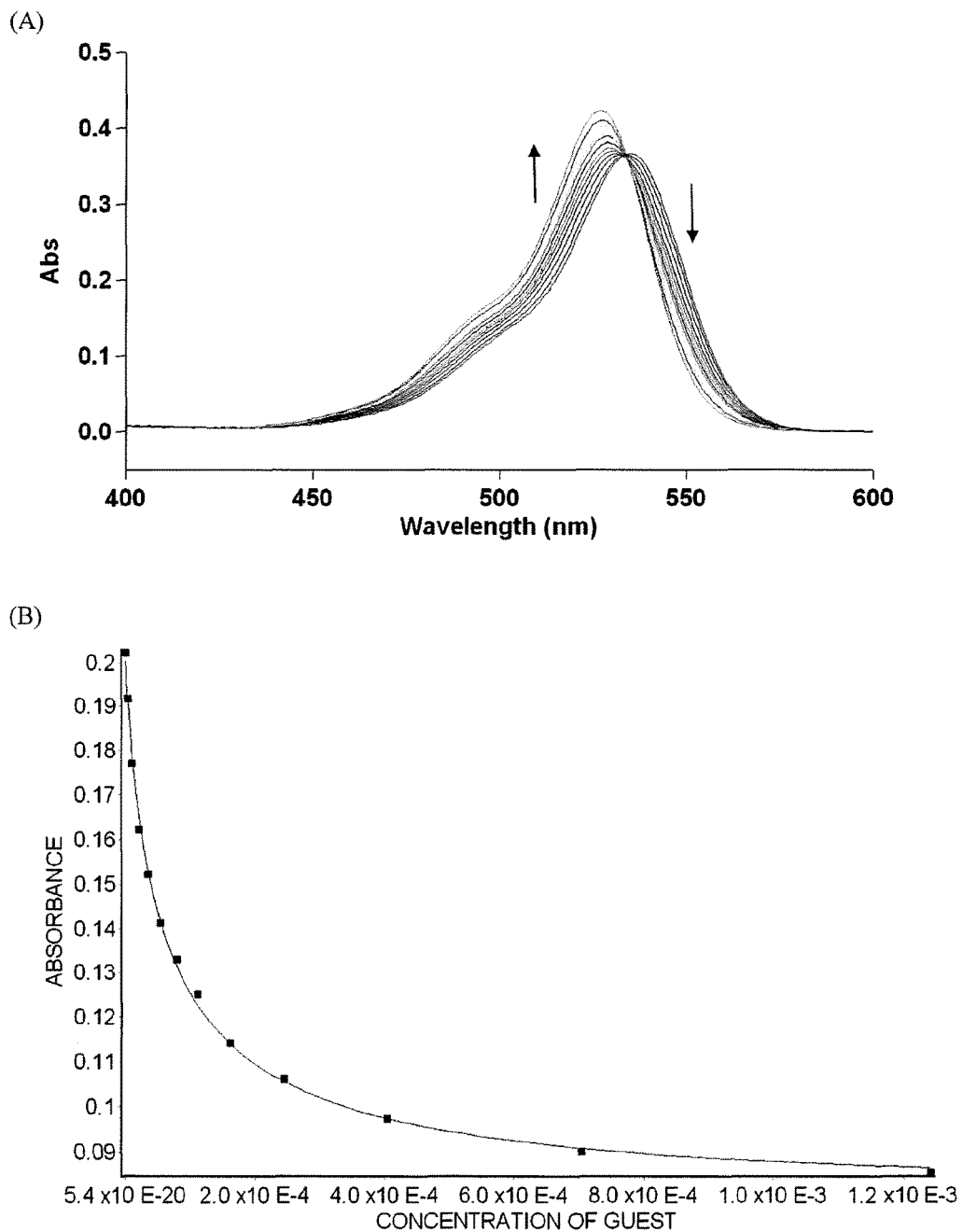
FIG. 52. (A) UV/Vis spectra from the titration of Motor 2 (4.97 μM) and rhodamine 6G (4.97 μM) with phencyclidine (0-1.242 mM) in 20 mM $NaH_2PO_4$ buffer (pH=7.4); (B) plot of the $A_{550}$ as a function of phencyclidine concentration. The solid line represents the best non-linear fit of the data to a competitive binding model ($K_a=(2.1\pm0.1)\times10^5$ $M^{-1}$).
Figure 53:
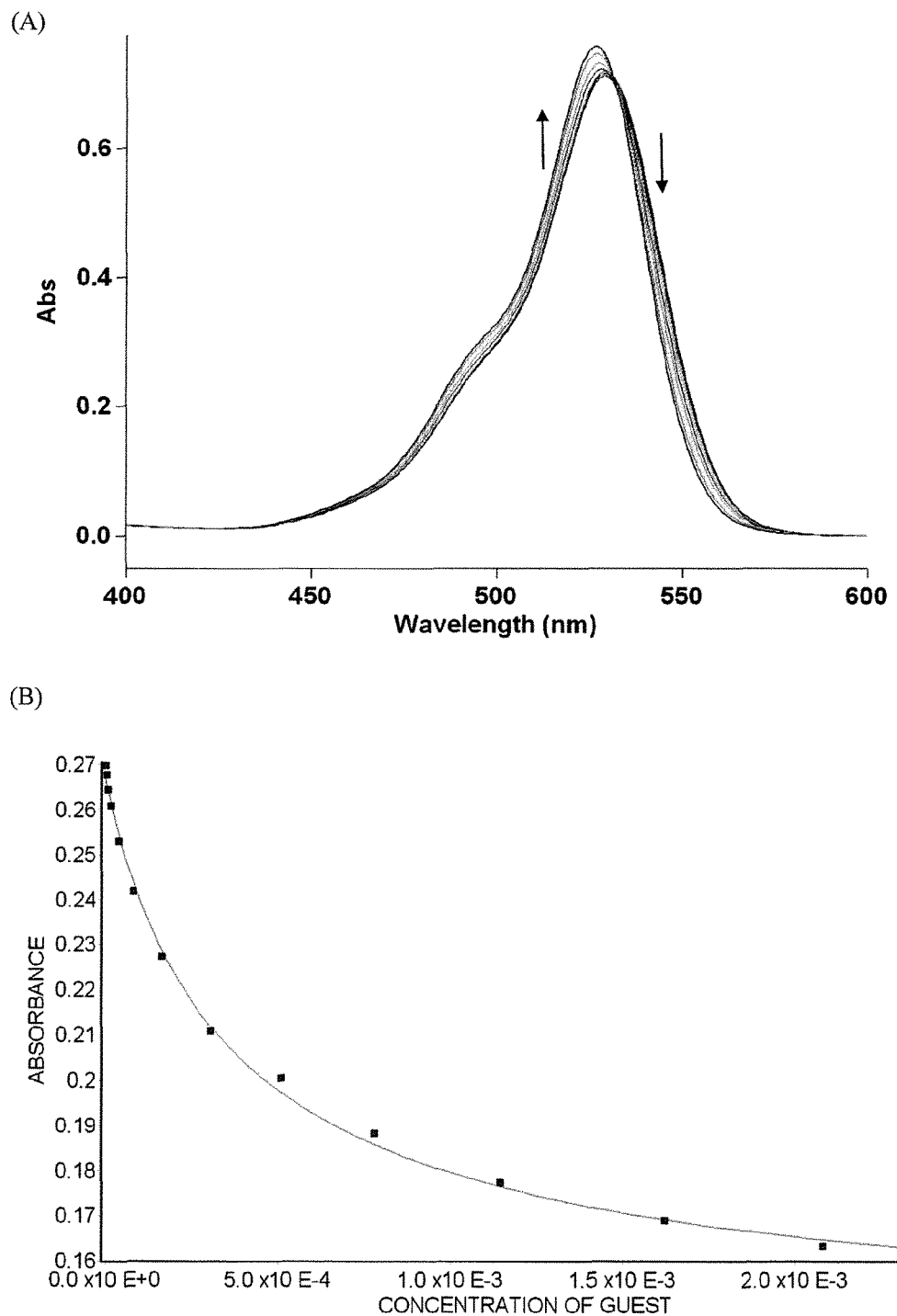
FIG. 53. (A) UV/Vis spectra from the titration of Motor 1 (5.01 μM) and rhodamine 6G (4.96 μM) with ketamine (0-2.44 mM) in 20 mM $NaH_2PO_4$ buffer (pH=7.4); (B) plot of the $A_{550}$ as a function of the concentration of ketamine. The solid line represents the best non-linear fit of the data to a competitive binding model ($K_a=(1.1\pm0.1)\times10^4$ $M^{-1}$).
Figure 54:
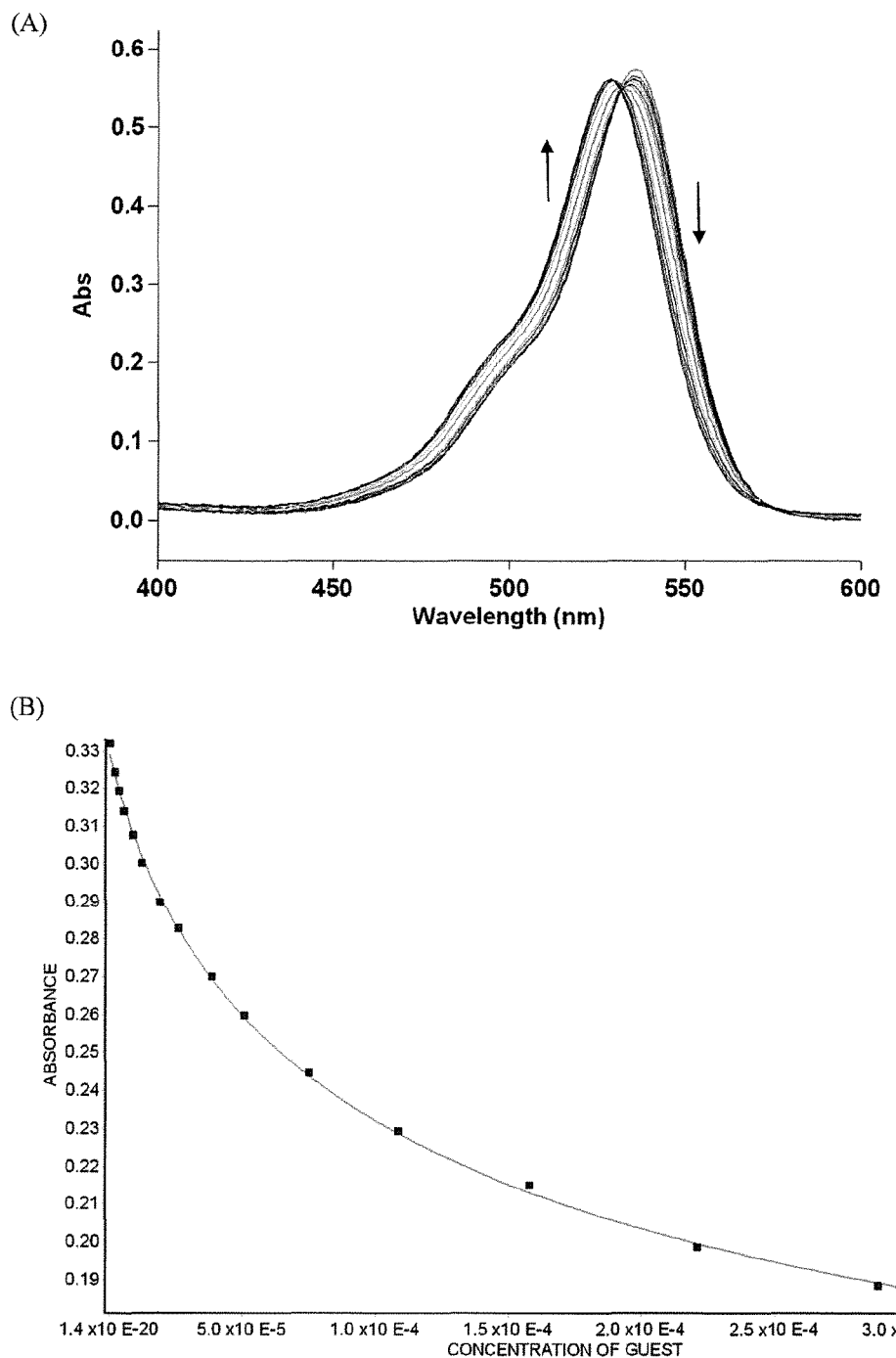
FIG. 54. (A) UV/Vis spectra from the titration of Motor 2 (9.18 μM) and rhodamine 6G (10.00 μM) with ketamine (0-0.35 mM) in 20 mM $NaH_2PO_4$ buffer (pH=7.4); (B) plot of the $A_{550}$ as a function of the concentration of ketamine. The solid line represents the best non-linear fit of the data to a competitive binding model ($K_a=(1.8\pm0.1)\times10^5$ $M^{-1}$).
Figure 55:
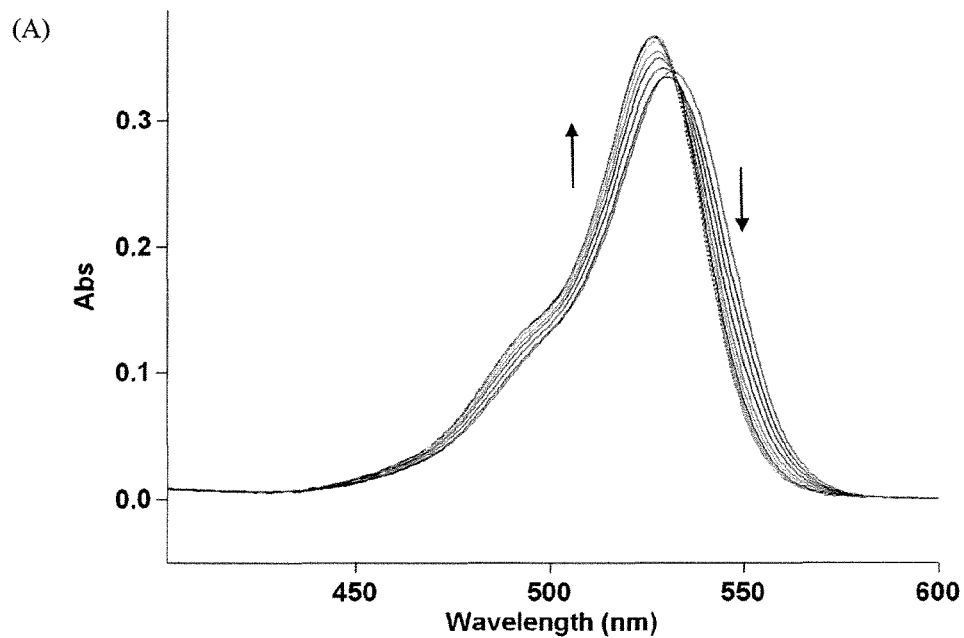
FIG. 55. (A) UV/Vis spectra from the titration of Motor 1 (5.00 μM) and rhodamine 6G (5.01 μM) with morphine (0-1.58 mM) in 20 mM $NaH_2PO_4$ buffer (pH 7.4); (B) plot of the $\Delta A_{550}$ as a function of morphine concentration. The solid line represents the best non-linear fit of the data to a 1:1 binding model ($K_a=(5.3\pm0.3)\times10^5$ $M^{-1}$).
Figure 55:
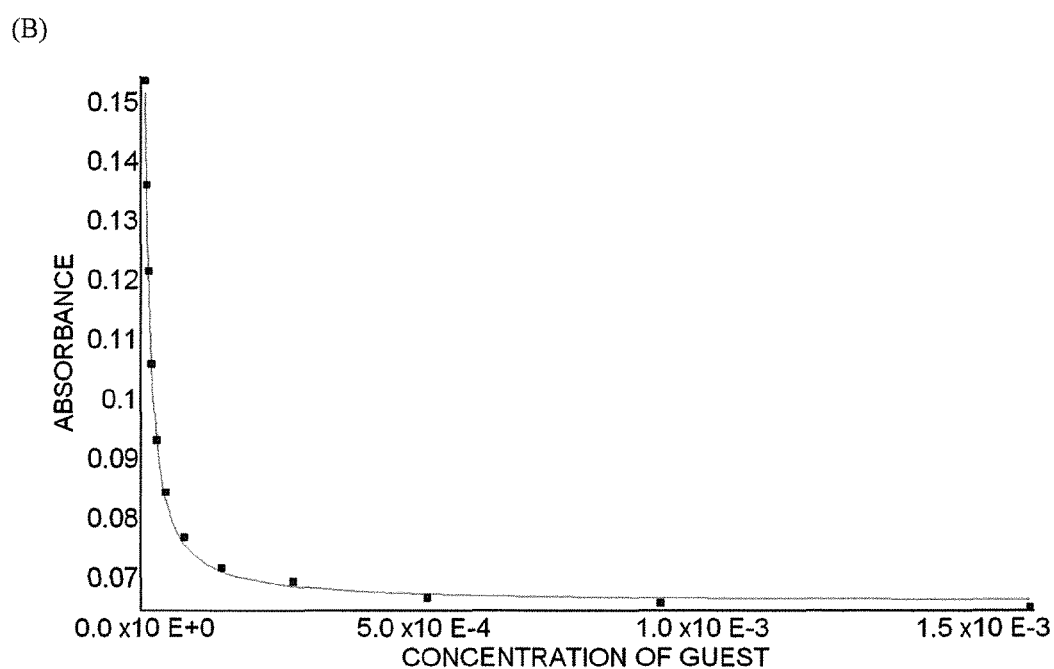
Figure 56:
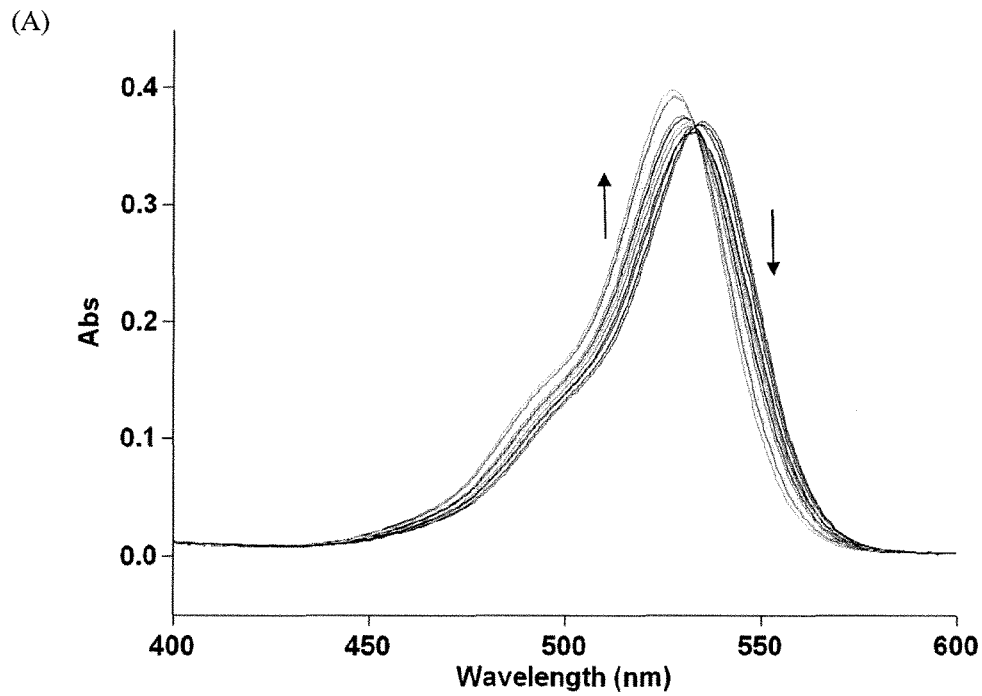
FIG. 56. (A) UV/Vis spectra from the titration of Motor 2 (5.07 μM) and Rhodamine 6G (5.01 μM) with morphine (0-107.33 μM) in 20 mM $NaH_2PO_4$ buffer (pH=7.4); (B) plot of the $A_{550}$ as a function of the concentration of morphine. The solid line represents the best non-linear fit of the data to a competitive binding model ($K_a=(5.3\pm0.4)\times10^5$ $M^{-1}$)
Figure 56:
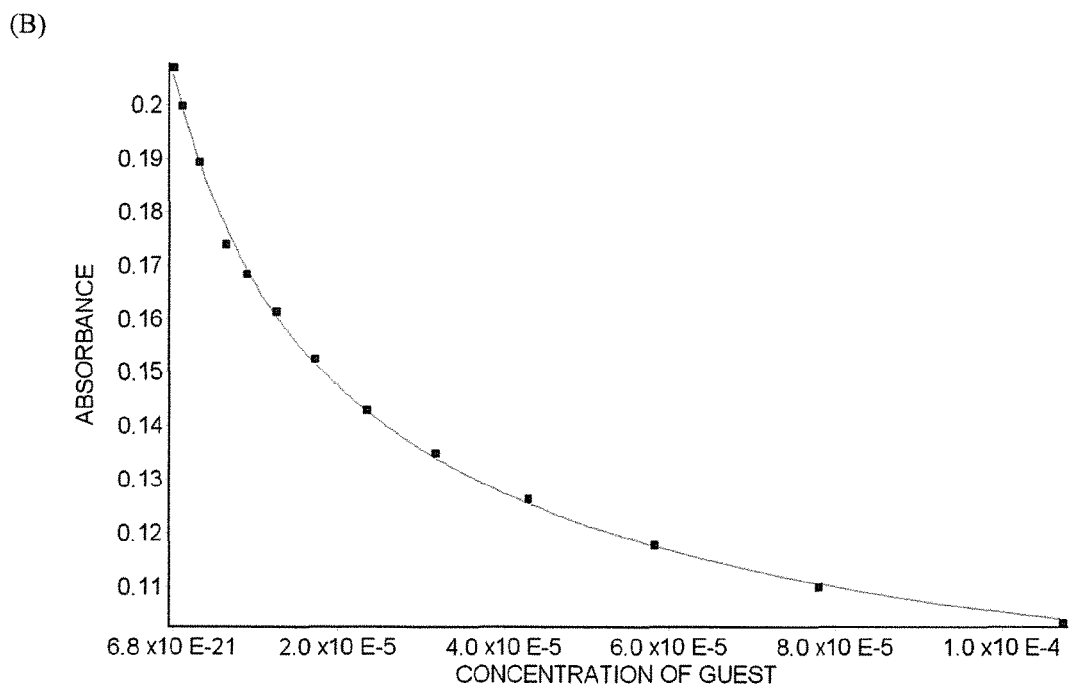
Figure 57:
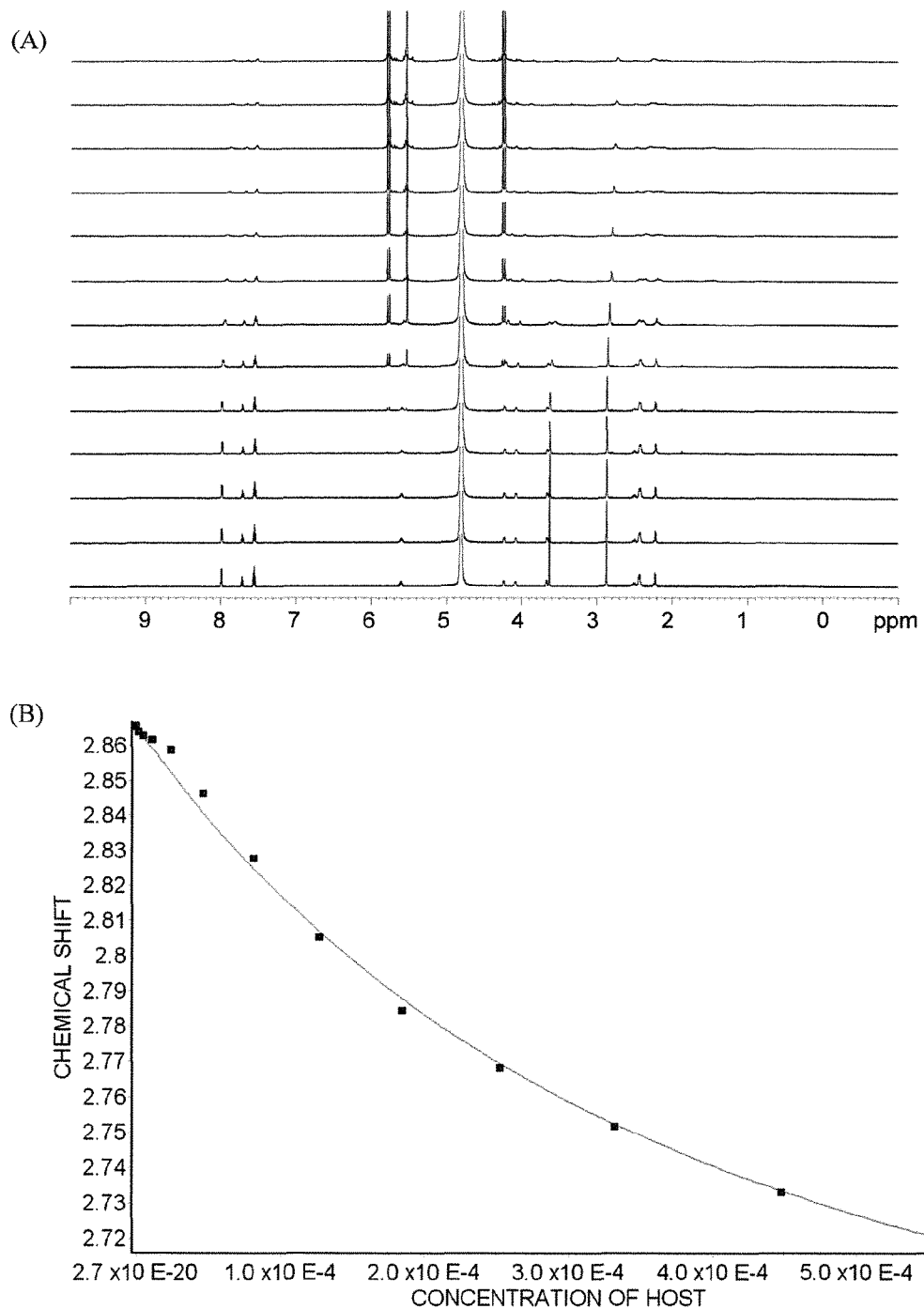
FIG. 57. (A) $^1$H NMR (600 MHz) stack plot from the titration of CB[7] (0-588 μM) with cocaine (103 μM) in 20 mM $NaH_2PO_4$ buffered (pH=7.4) $D_2O$; (B) plot of the chemical shift at 2.8654 ppm as a function of cocaine concentration. The solid line represents the best non-linear fit of the data to a 1:1 model ($K_a=(2.3\pm0.2)\times10^3$ $M^{-1}$).
Figure 58:
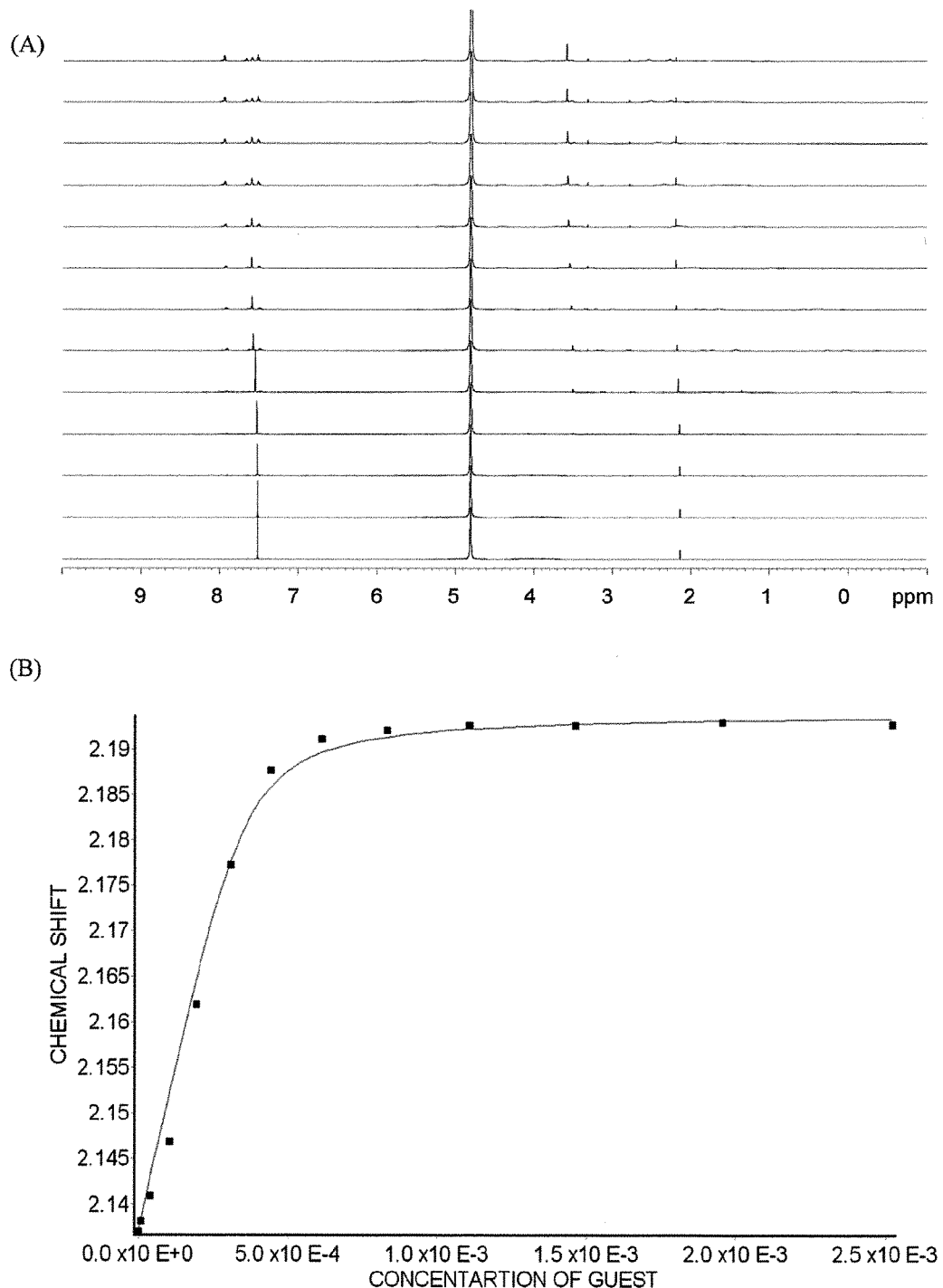
FIG. 58. (A) $^1$H NMR (600 MHz) stack plot from the titration of 4-sulfo calix[4]arene 4 (0.3502 mM) with cocaine (0-2.519 mM) in 20 mM $NaH_2PO_4$ buffered (pH=7.4) $D_2O$; (B) plot of the chemical shift at 2.1371 ppm as a function of cocaine concentration. The solid line represents the best non-linear fit of the data to a 1:1 model ($K_a=(4.3\pm1.5)\times10^4$ $M^{-1}$).
Figure 59:
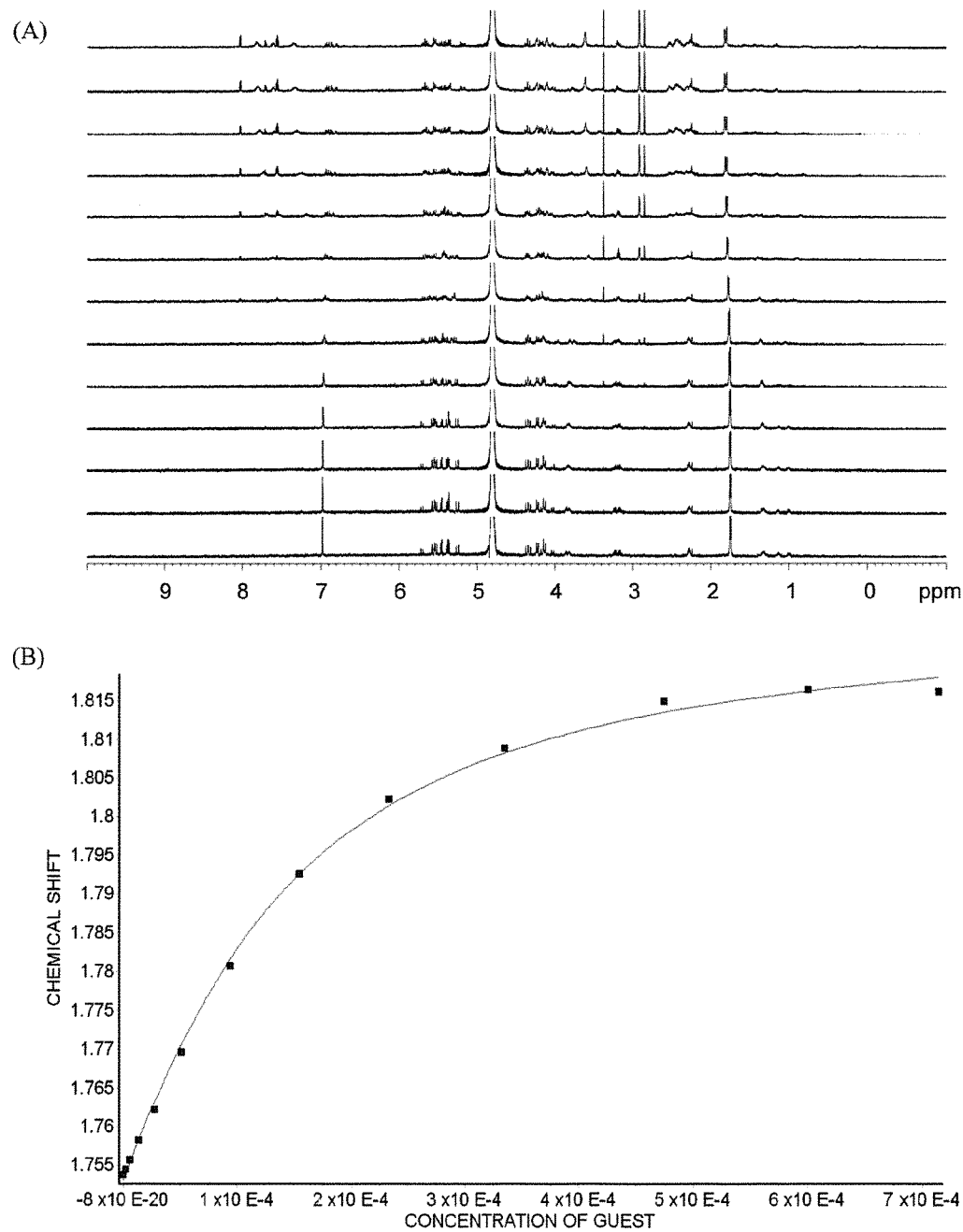
FIG. 59. (A) $^1$H NMR (600 MHz) stack plot from the titration of hexyl capped Motor1 (0.10 mM) with cocaine (0-0.71 mM) in 20 mM $NaH_2PO_4$ buffered (pH=7.4) $D_2O$; (B) plot of the chemical shift at 1.75 ppm as a function of cocaine concentration. The solid line represents the best non-linear fit of the data to a 1:1 model ($K_a=(1.1\pm0.1)\times10^4$ $M^{-1}$).
Figure 60:
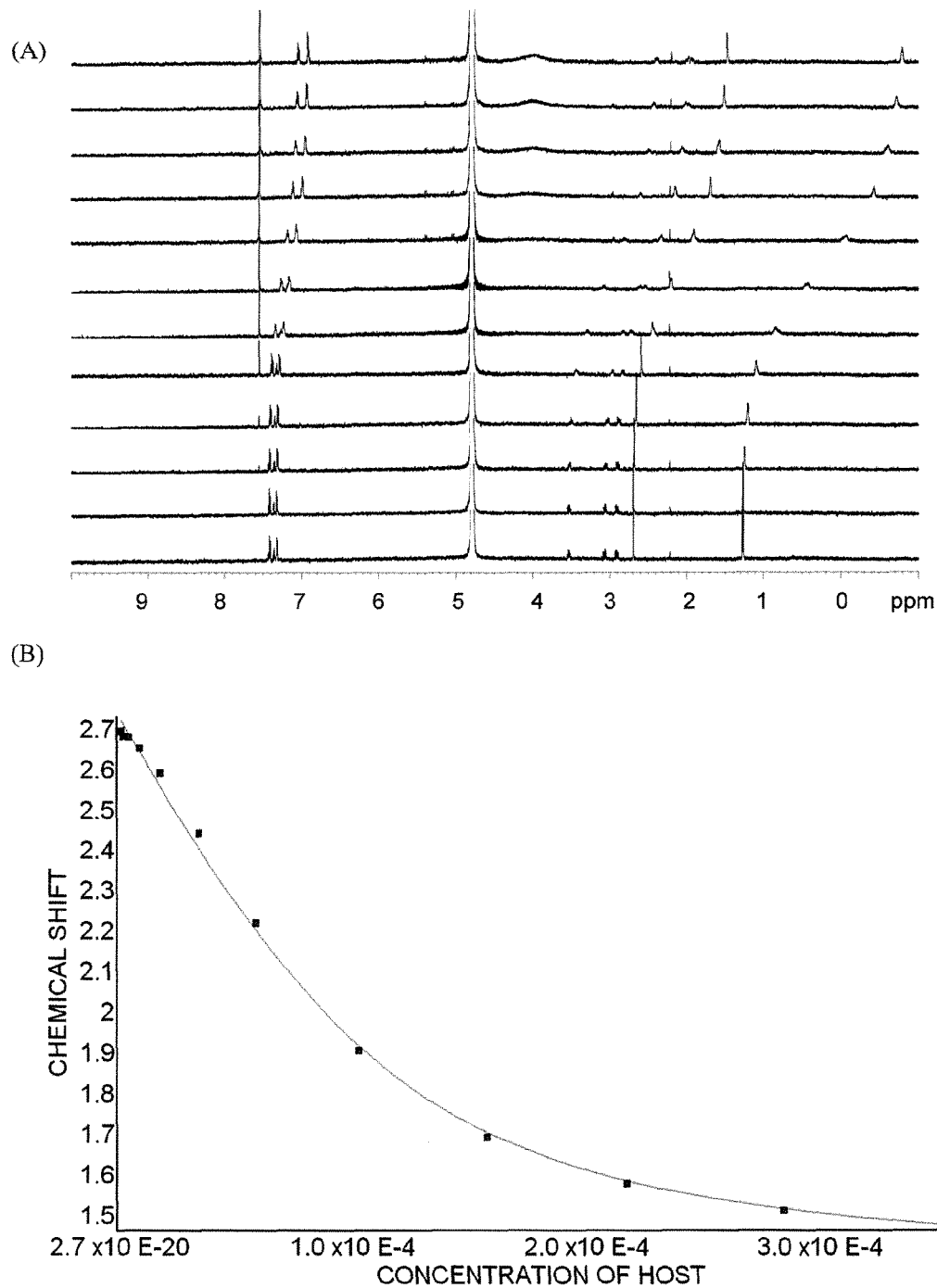
FIG. 60. (A) $^1$H NMR (600 MHz) stack plot from the titration of methamphetamine (0.11 mM) with host 4-sulfo calix[4]arene (0-0.36 mM) in 20 mM $NaH_2PO_4$ buffered (pH=7.4) $D_2O$; (B) plot of the chemical shift at 2.7 ppm as a function of 4-sulfo calix[4]arene concentration. The solid line represents the best non-linear fit of the data to a 1:1 model ($K_a=(3.8\pm0.6)\times10^4$ $M^{-1}$).
Figure 61:
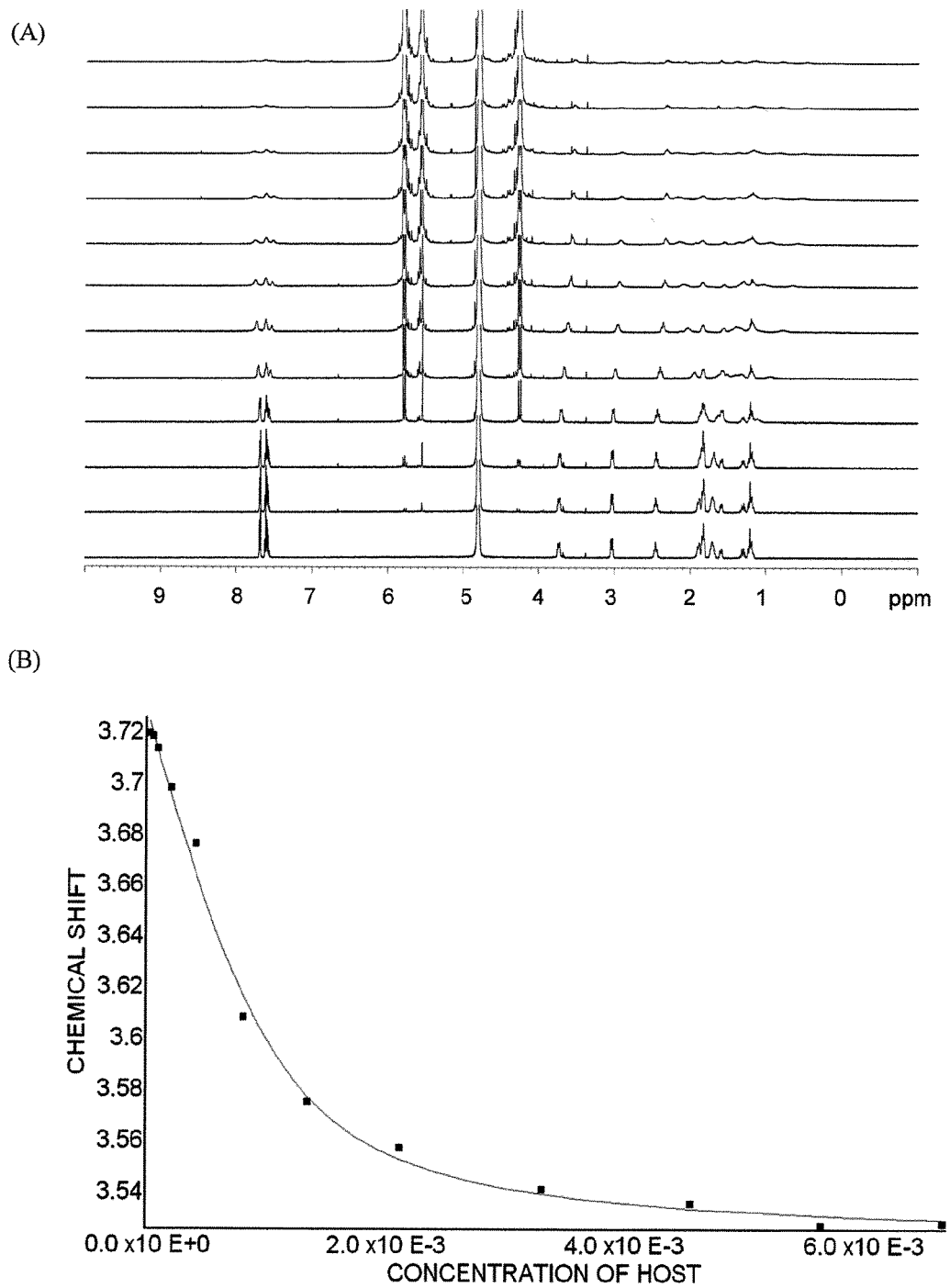
FIG. 61. (A) $^1$H NMR (600 MHz) stack plot from the titration of phencyclidine (1.00 mM) with CB[7] (0-6.65 mM) in 20 mM $NaH_2PO_4$ buffered (pH=7.4) $D_2O$; (B) plot of the chemical shift at 3.7 ppm as a function of CB[7] concentration. The solid line represents the best non-linear fit of the data to a 1:1 model ($K_a=(4.4\pm0.9)\times10^3$ $M^{-1}$).
Figure 62:
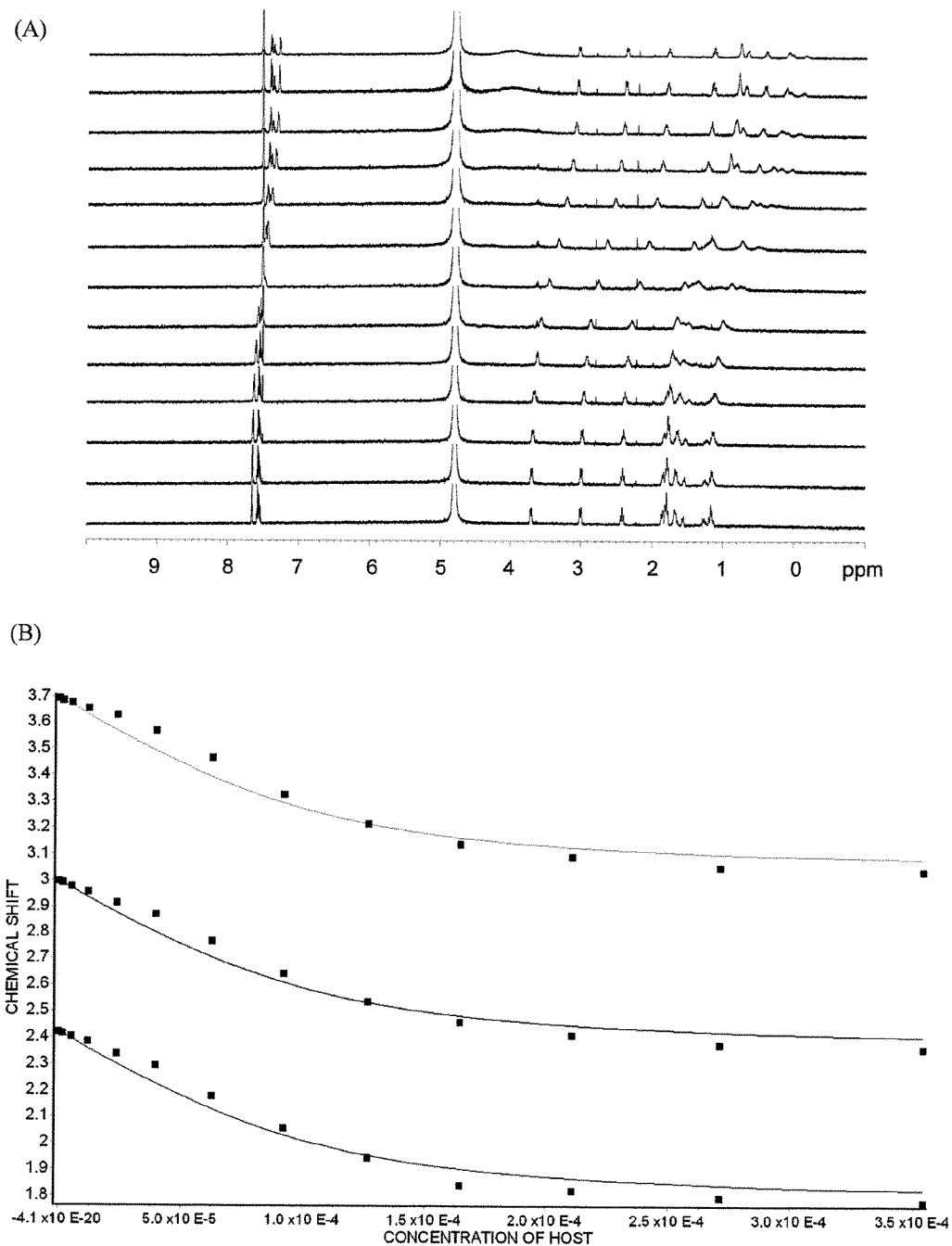
FIG. 62. (A) $^1$H NMR (600 MHz) stack plot from the titration of phencyclidine (0.10 mM) with 4-sulfo calix[4]arene (0-0.35 mM) in 20 mM $NaH_2PO_4$ buffered (pH=7.4) $D_2O$; (B) plot of the chemical shift at 2.4, 3.0, and 3.7 ppm as a function of 4-sulfo calix[4]arene concentration. The solid line represents the best non-linear fit of the data to a 1:1 model ($K_a=(5.0\pm0.6)\times10^4$ $M^{-1}$).
Figure 63:
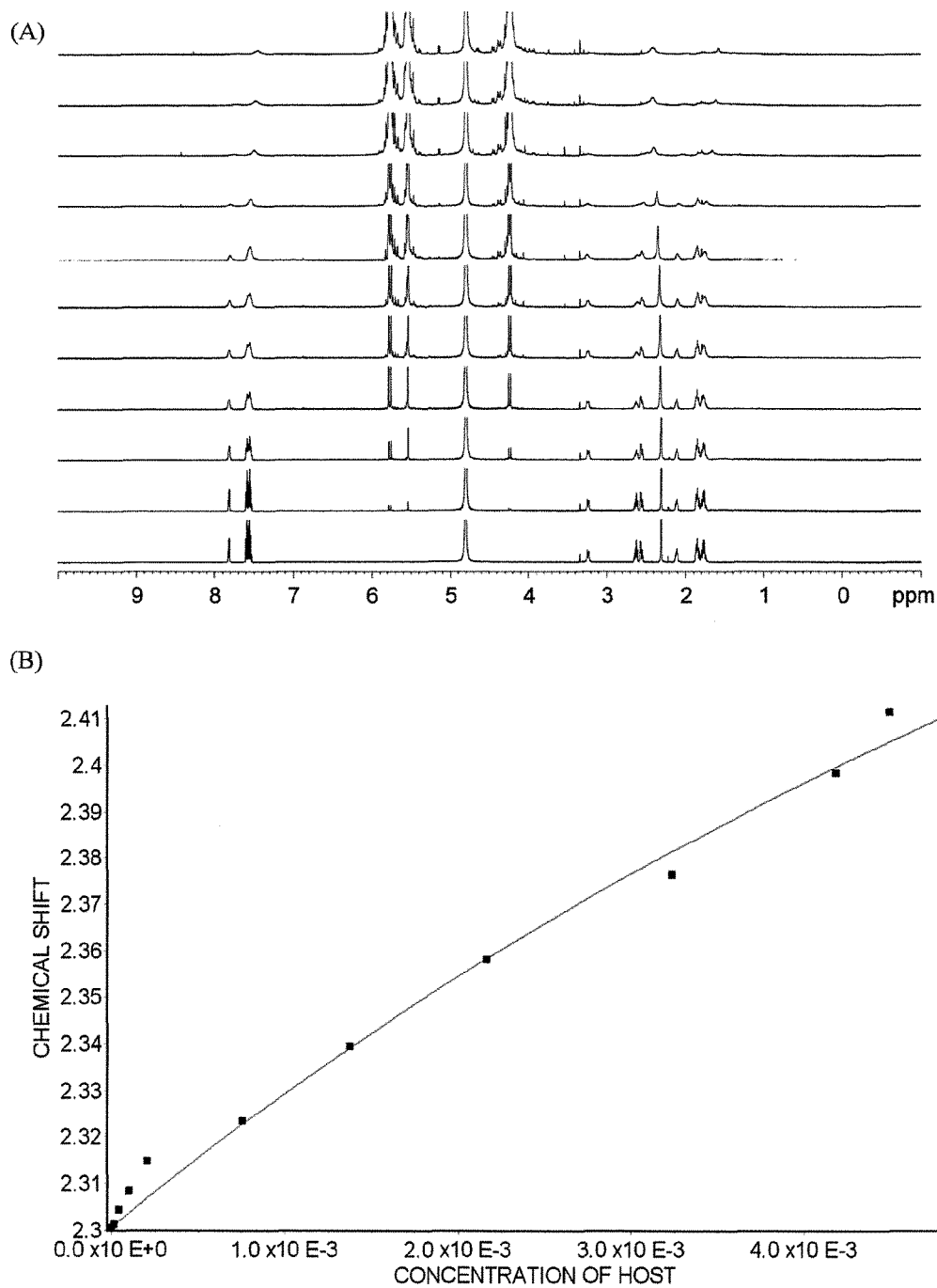
FIG. 63. (A) $^1$H NMR (600 MHz) stack plot from the titration of ketamine (1.00 mM) with host CB[7] (0-4.9 mM) in 20 mM $NaH_2PO_4$ buffered (pH=7.4) $D_2O$; (B) plot of the chemical shift at 2.3 ppm as a function of host CB[7] concentration. The solid line represents the best non-linear fit of the data to a 1:1 model ($K_a=(6.4\pm1.2)\times10^2$ $M^{-1}$).
Figure 64:
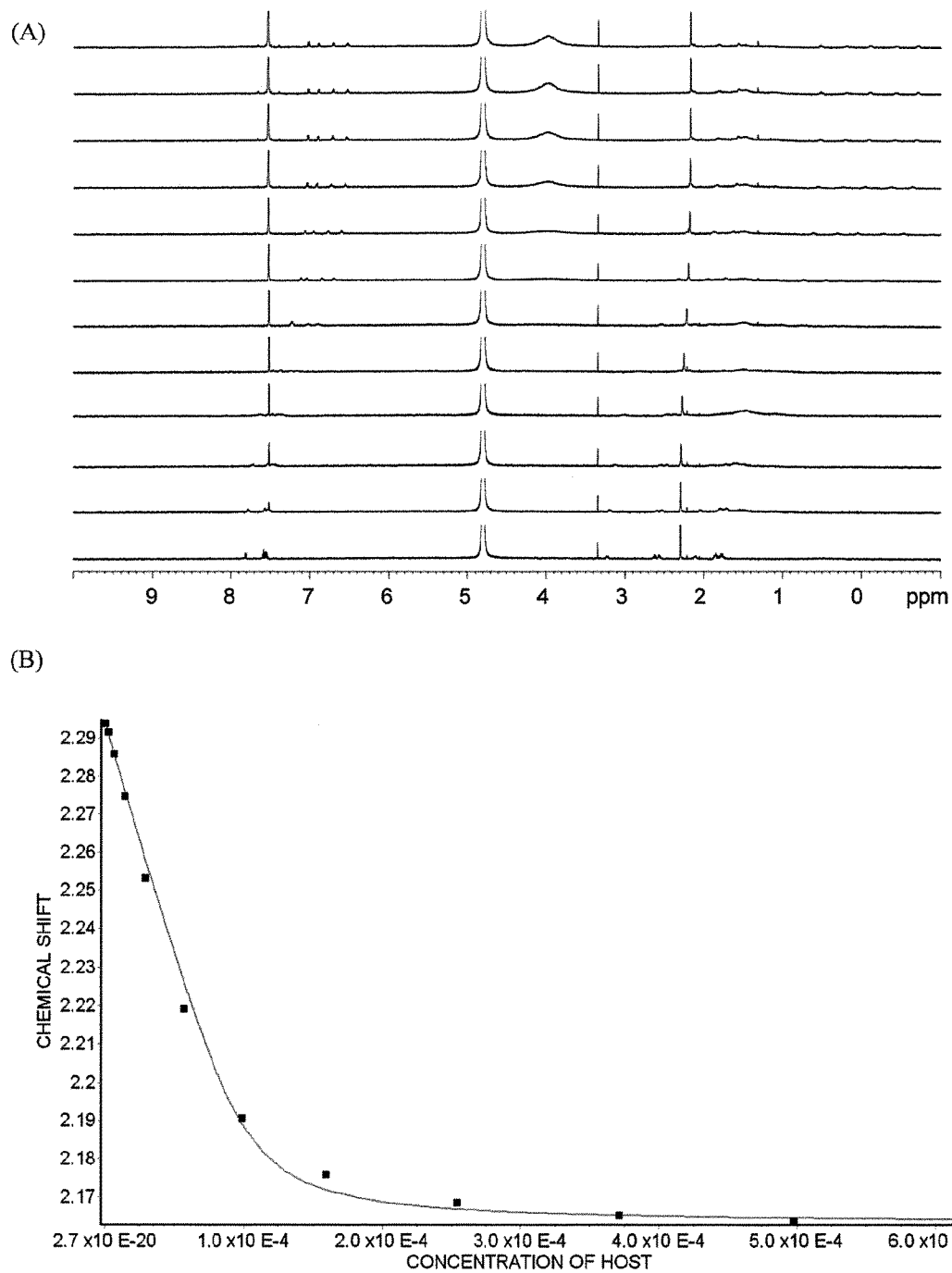
FIG. 64. (A) $^1$H NMR (600 MHz) stack plot from the titration of ketamine (1.00 mM) with 4-sulfo calix[4]arene (0-0.61 mM) in 20 mM $NaH_2PO_4$ buffered (pH=7.4) $D_2O$; (B) plot of the chemical shift at 2.3 ppm as a function of 4-sulfo calix[4]arene concentration. The solid line represents the best non-linear fit of the data to a 1:1 model ($K_a=\sim10^5$ $M^{-1}$).
Figure 65:
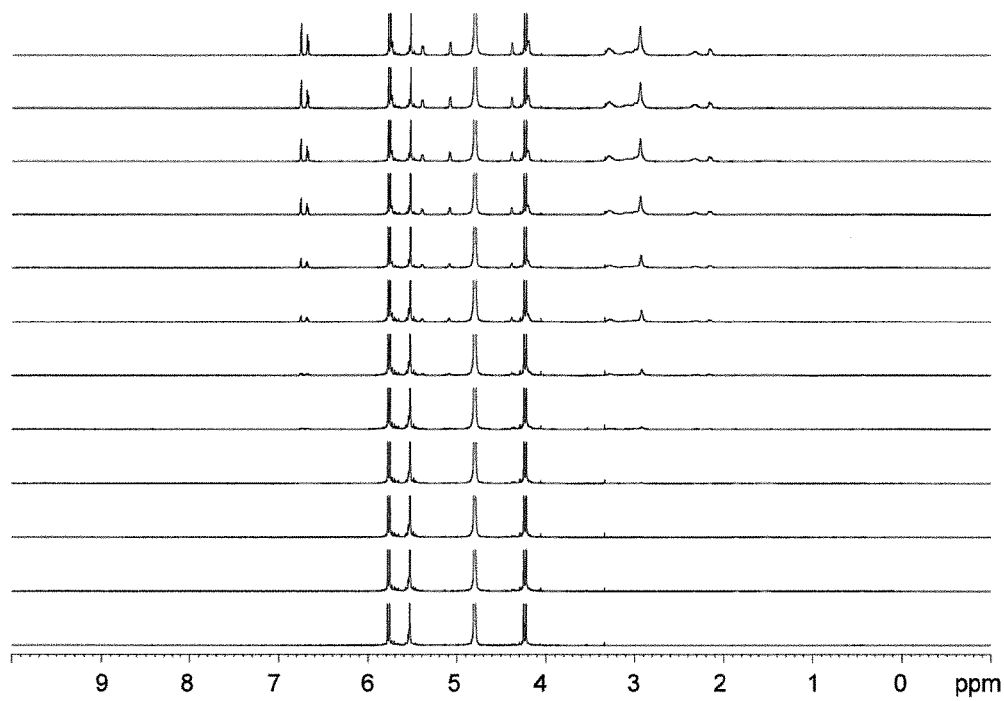
FIG. 65. $^1$H NMR (600 MHz) stack plot from the titration of CB[7] (1.00 mM) with morphine (0-6.9 mM) in 20 mM $NaH_2PO_4$ buffered (pH=7.4) $D_2O$; no significant shifts observed ($K_a<10^3$ $M^{-1}$).
Figure 66:
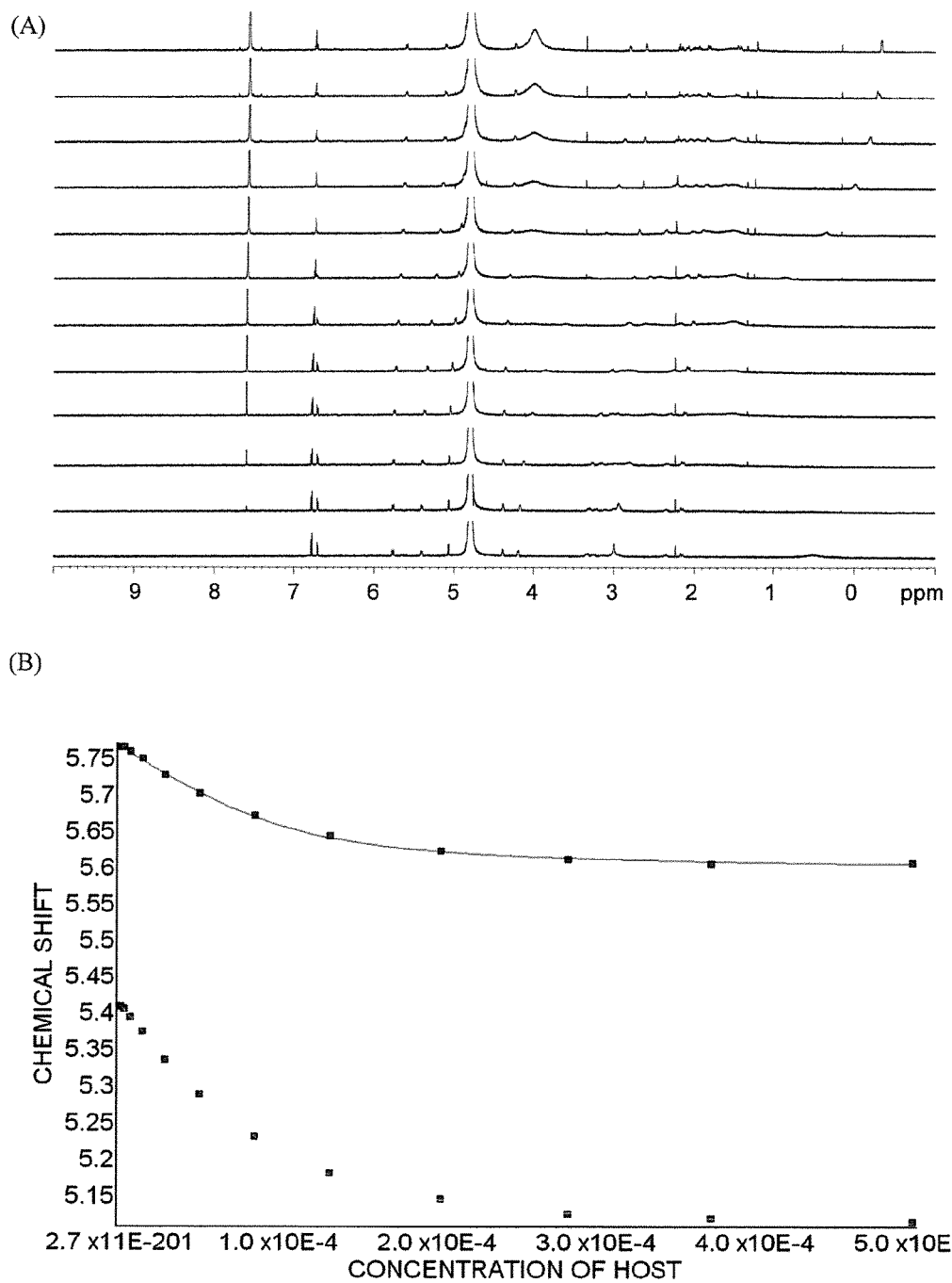
FIG. 66. (A) $^1$H NMR (600 MHz) stack plot from the titration of morphine (0.10 mM) with 4-sulfo calix[4]arene (0-0.5 mM) in 20 mM $NaH_2PO_4$ buffered (pH=7.4) $D_2O$; (B) plot of the chemical shift at 5.4 and 5.8 ppm as a function of 4-sulfo calix[4]arene concentration. The solid line represents the best non-linear fit of the data to a 1:1 model ($K_a=(4.9\pm0.3)\times10^4$ $M^{-1}$).

The following description is related to testing the ability of the molecular containers shown in FIG. 46 (Motor 1 also referred to herein as Calabadion 1; and Motor2 also referred to herein as Calabadion 2; cucurbit[7]uril, sulfonated calix [4]arene, and hexyl capped Motor 1 to bind to five important drugs of abuse namely cocaine hydrochloride, methamphetamine hydrochloride, and phencyclidine hydrochloride, ketamine hydrochloride, and morphine sulfate to assess their potential use. We have also tested the binding of Motor2 toward a wide variety of drugs as part of its development as a reversal agent for neuromuscular block including propranolol, atropine, lidocaine, bupivacaine, and imipramine. The following description relates to data summarized in FIGS. 46-FIG. 67.

Determination of $K_a$ between Hosts Motor 1 and Motor 2 with drugs (cocaine, methamphetamine, phencyclidine, ketamine, morphine) (using UV/Vis spectroscopy. An indicator displacement assay involving the addition of guest to a solution of either Motor 1 or Motor 2 and dye rhodamine 6G was used. The change in UV/Vis absorbance as a function of guest concentration was fitted to a competitive binding model which allowed determination of the $K_a$ values. The known $K_a$ values between Motor 2•rhodamine 6G $(2.3\times10^6$ $M^{-1})$ and Motor 1•rhodamine 6G $(4.8\times10^5$ $M^{-1})$ were used as inputs in the competitive binding model.[1]

TABLE 5

Binding constants determined by competitive UV/Vis assays or direct $^1$H NMR titrations for the interaction between various hosts and drugs of abuse.

| Guest | Binding Constant with Host ($K_a$ [$M^{-1}$]) | | | | |
|---|---|---|---|---|---|
| | Motor 1 | Motor 2 | CB[7] | 4-suldo calix[4]arene | Hexyl capped Motor1 |
| cocaine | $(6.6 \pm 0.4) \times 10^5$ | $(1.0 \pm 0.1) \times 10^6$ | $(2.3 \pm 0.2) \times 10^3$ | $(4.3 \pm 1.5) \times 10^4$ | $(1.1 \pm 0.1) \times 10^4$ |
| methamphetamine | $(7.5 \pm 2.9) \times 10^6$ | $(4.3 \pm 1.0) \times 10^6$ | $(1.3 \pm 0.2) \times 10^8$ | $(3.8 \pm 0.6) \times 10^4$ | $>10^4$ |
| phencyclidine | $(4.7 \pm 0.5) \times 10^4$ | $(2.1 \pm 0.1) \times 10^5$ | $(4.4 \pm 0.9) \times 10^3$ | $(5.0 \pm 0.6) \times 10^4$ | $>10^4$ |
| ketamine | $(1.1 \pm 0.1) \times 10^4$ | $(1.8 \pm 0.1) \times 10^5$ | $(6.4 \pm 1.2) \times 10^2$ | $\sim 10^5$ | — |
| morphine | $(5.3 \pm 0.3) \times 10^5$ | $(5.3 \pm 0.4) \times 10^5$ | $<10^3$ | $(4.9 \pm 0.3) \times 10^4$ | — |

Binding Model Used to Determine Values of $K_a$ by fitting the UV/Vis Absorbance data using Micromath Scientist Competitive Binding (Indicator Displacement) Model

```
// MicroMath Scientist Model File
IndVars: ConcAntot
DepVars: Absorb
Params: ConcHtot, ConcGtot, Khg, Kha, AbsorbMax, AbsorbMin
Khg = ConcHG/(ConcH * ConcG)
Kha = ConcHAn/(ConcH * ConcAn)
Absorb = AbsorbMin + (AbsorbMax - AbsorbMin) * (ConcHG/ConcGtot)
ConcHtot = ConcH + ConcHG + ConcHAn
ConcGtot = ConcHG + ConcG
ConcAntot = ConcAn + ConcHAn
0 < ConcHG < ConcHtot
0 < ConcH < ConcHtot
0 < ConcG < ConcGtot
0 < ConcAn < ConcAntot
***
```

Determination of $K_a$ Between Hosts CB[7] and 4-Sulfo Calix[4]Arene and Guests Cocaine and Methamphetamine Using $^1$H NMR.

A direct titration was performed between the host and guest. The concentration of the host was kept constant while varying the concentration of the guest and the change in chemical shift of a selected host signal was measured. The change in chemical shift as a function of guest concentration was fitted to a 1:1 binding model to determine the $K_a$. In some cases, the concentration of guest was fixed and host concentration was varied, depending on the availability of a suitable $^1$H NMR peak whose chemical shift change could be easily monitored.

1:1 Binding Model for NMR

```
// Micromath Scientist Model File
// 1:1 Host:Guest binding model
//This model assumes the guest concentration is fixed and host
concentration is varied
IndVars: ConcHostTot
DepVars: SpectroscopicSignal
Params: Ka, ConcGuestTot, SpectroscopicSignalMin,
SpectroscopicSignalMax
Ka = ConcHostGuest/(ConcHostFree * ConcGuestFree)
ConcHostTot = ConcHostFree + ConcHostGuest
ConcGuestTot = ConcGuestFree + ConcHostGuest
SpectroscopicSignal = SpectroscopicSignalMin +
(SpectroscopicSignalMax -
SpectroscopicSignalMin) * (ConcHostGuest/ConcGuestTot)
//Constraints
0 < ConcHostFree < ConcHostTot
0 < Ka
0 < ConcGuestFree < ConcGuestTot
0 < ConcHostGuest < ConcHostTot
***
```

Sample Determination of $K_{rel}$ for the Competition Between TMSP and Methamphetamine for CB[7].

Figure 67:
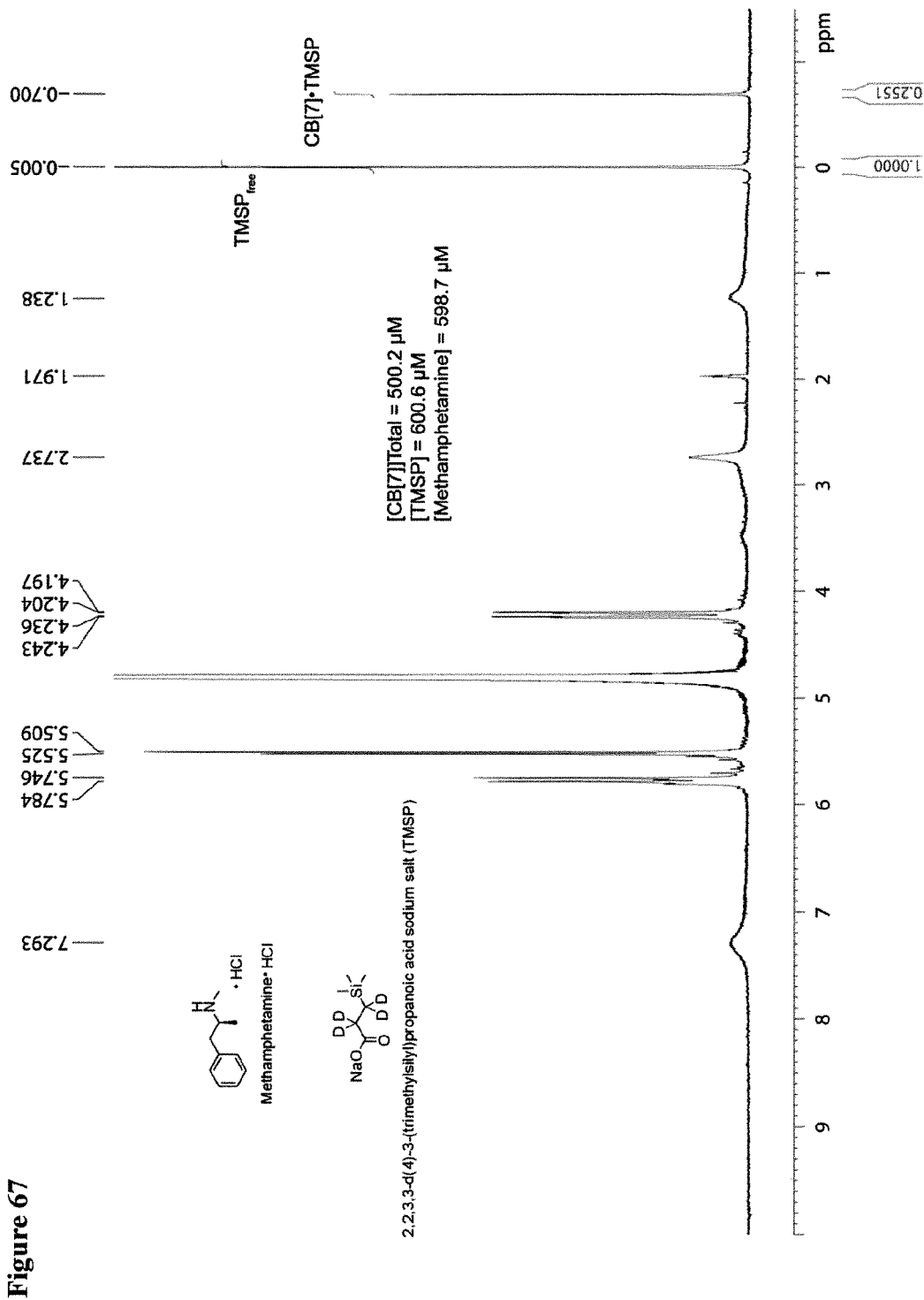
FIG. 67. One of the $^1$H NMR (600 MHz) spectra used in the determination of $K_{rel}$ for CB[7]•methamphetamine and CB[7]•TMSP.
Figure 68:
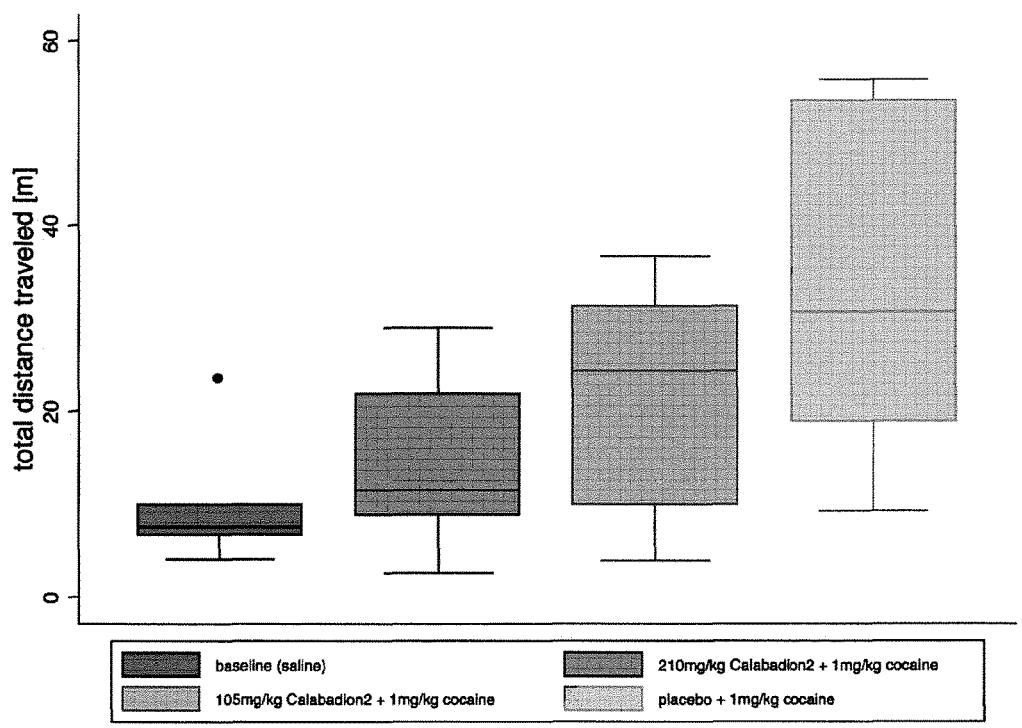
FIG. 68: Effects of calabadion 2 on distance travelled of rats following cocaine injection. Box-plot showing median, interquartile range, 10 and 90 percent percentile, as well as outer fence. Cocaine compared to placebo (saline) markedly increased the distance travelled of living rats in an open field. Calabadion 2 dose-dependently inhibited these cocaine-induced effects such that at the highest calabadion 2 dose distance travelled did not differ between rats given cocaine and those who did not receive cocaine.
Figure 69:
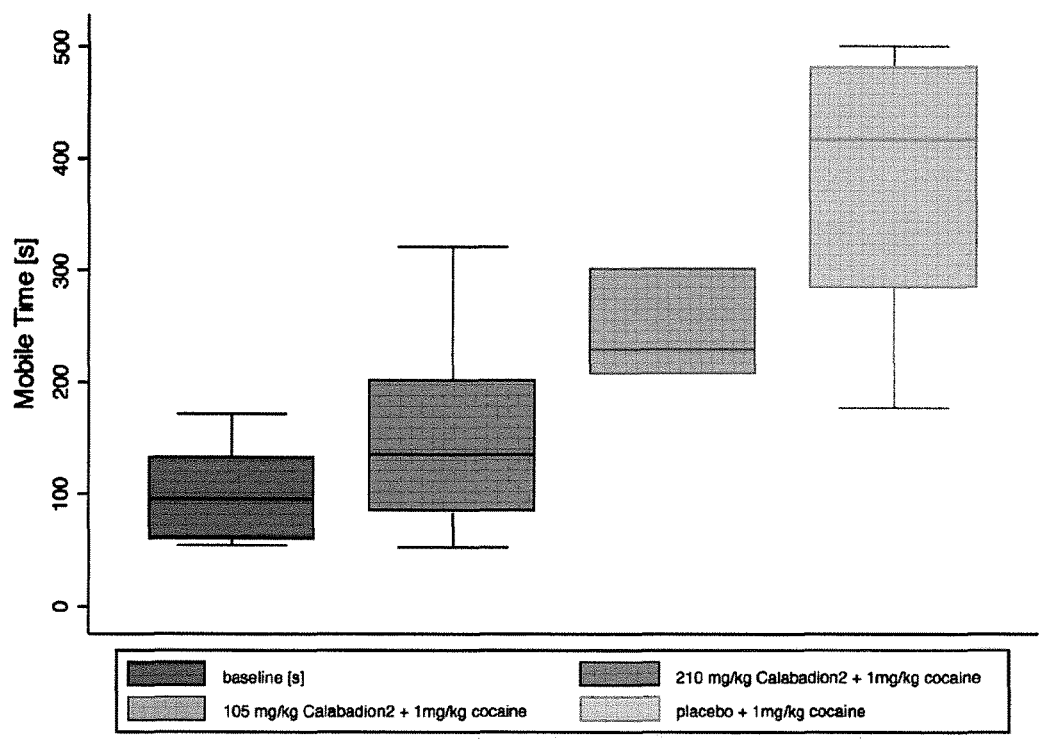
FIG. 69: Effects of calabadion 2 on total duration of mobility of rats following cocaine injection. Box-plot showing median, interquartile range, 10 and 90 percent percentile, as well as outer fence. Cocaine compared to placebo (saline) markedly increased mobile time of living rats in an open field. Calabadion 2 dose-dependently inhibited these cocaine-induced effects such that at the highest calabadion 2 dose mobile time did not differ between rats given cocaine and those who did not receive cocaine.
Figure 70:
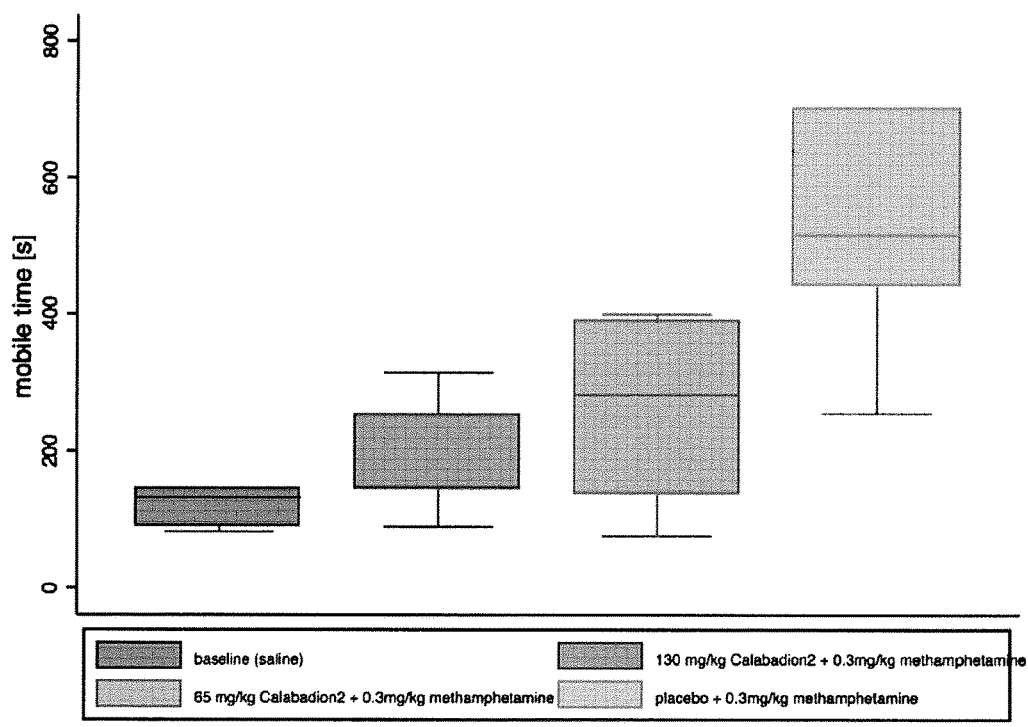
FIG. 70: Effects of calabadion 2 on mobile time of rats following methamphetamine injection. Box-plot showing median, interquartile range, 10 and 90 percent percentile, as well as outer fence. Methamphetamine compared to placebo (saline) markedly increased the mobile time of living rats in an open field. Calabadion 2 dose-dependently inhibited these methamphetamine-induced effects such that at the highest calabadion 2 dose mobile time did not differ between rats given methamphetamine and those who did not receive methamphetamine.
Figure 71:
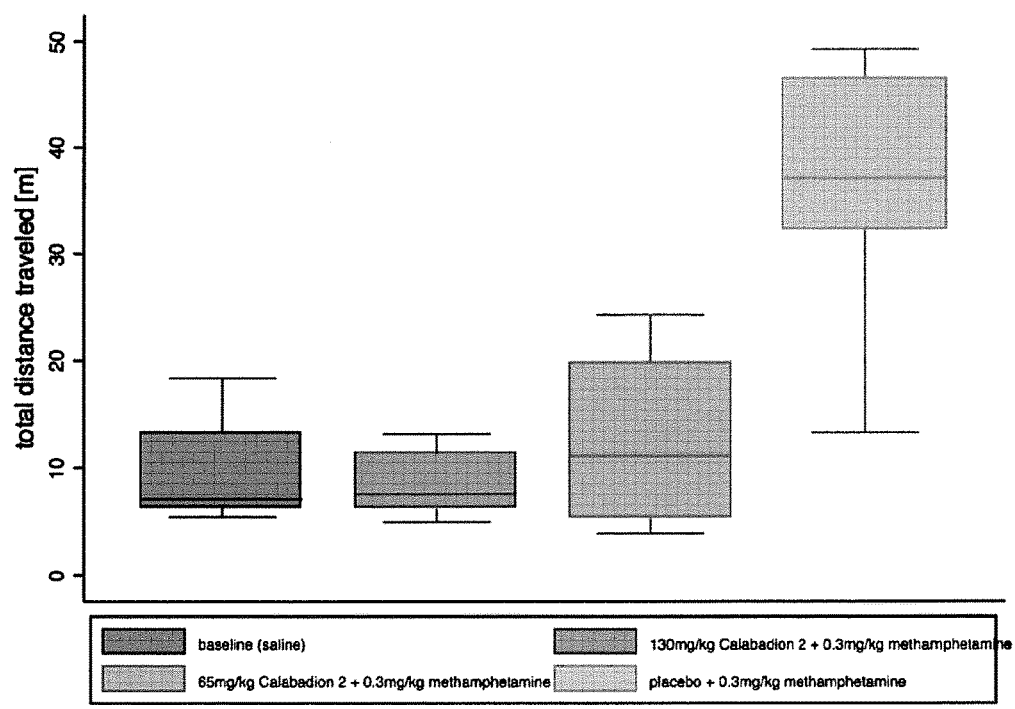
FIG. 71: Effects of calabadion 2 on total distance traveled mobile time of rats following methamphetamine injection.

Equation 1 was used to determine $K_{rel}$ for the interaction of TMSP and methamphetamine for CB[7]. For this purpose, a solution containing CB[7] (500.2 μM), TMSP (600.6 μM), and methamphetamine (598.7 μM) was prepared and allowed to reach equilibrium (FIG. 67). Next the relative concentrations of $TMSP_{free}$ and CB[7]•methamphetamine were determined by integration of the appropriate resonances in the $^1$H NMR spectrum (FIG. 67: $TMSP_{free}$: −0.005 ppm; CB[7]TMSP: −0.700 ppm). Using the relative concentrations and the mass balance expression (equation 2) $[TMSP]_{free}$=478.5 μM and [CB[7]•TMSP]=122.1 μM were calculated. Equation 3 was then used to calculate [CB[7]•methamphetamine]=378.1 μM using the known value of CB[7]•TMSP. Lastly, equation 4 was used to calculate [methamphetamine]$_{free}$=220.6 mM using the known value of [CB[7]•TMSP].

$$K_{rel}=([CB[7] \cdot \text{methamphetamine}][TMSP]_{free})/(CB[7] \cdot TMSP][\text{methamphetamine}]_{free}) \quad (1)$$

$$[TMSP]_{Total}=600.6 \text{ μM}=[TMSP]_{free}+[CB[7] \cdot TMSP] \quad (2)$$

$$[CB[7]]_{Total}=500.2 \text{ μM}=[CB[7] \cdot TMSP]+[CB[7] \cdot \text{methamphetamine}] \quad (3)$$

$$[\text{methamphetamine}]_{Total}=598.7 \text{ μM}=[\text{methamphetamine}]_{free}+[CB[7] \cdot \text{methamphetamine}] \quad (4)$$

Substitution of the values of [CB[7]•TMSP], $[TMSP]_{free}$, [CB[7]•methamphetamine], and [methamphetamine]$_{free}$ into equation 1 gave $K_{rel}$=6.72. These determinations were done in triplicate from independently prepared stock solutions and the average values were used in the calculations of $K_a$. In preparing the solutions for the above determinations a small excess of TMSP was used to ensure there is no free CB[7]. The $K_a$ for CB[7]•methamphetamine was calculated using the average $K_{rel}$ and the known value of CB[7]•TMSP ((1.82±0.22)×10$^7$ M$^{-1}$).

Table 6 given below tabulates the binding constants determined by UV/Vis competition experiments and/or 1H NMR titrations between Motor2 and a variety of additional drugs used in clinical practice. Binding constants ($K_a$, M$^{-1}$) between Motor 2 and selected drugs measured in pH 7.4 sodium phosphate buffered water at room temperature.

TABLE 6

| Guest | Motor 2 |
|---|---|
| Suxmethonium chloride | $(2.8 \pm 0.1) \times 10^6$ |
| Naloxone hydrochloride | $(8.0 \pm 0.7) \times 10^5$ |
| Diltiazem hydrochloride | $(4.8 \pm 0.3) \times 10^4$ |
| Phenylephrine hydrochloride | $(8.3 \pm 0.6) \times 10^4$ |
| Atropine sulfate | $(3.3 \pm 0.5) \times 10^6$ |
| Lidocaine hydrochloride | $(8.6 \pm 0.8) \times 10^3$ |
| Bupivacaine hydrochloride | $(2.1 \pm 0.2) \times 10^4$ |
| Dibucaine hydrochloride | $(5.9 \pm 0.7) \times 10^5$ |
| Tetracycline | $(2.3 \pm 0.2) \times 10^3$ |
| Kanamycin sulfate | $(3.0 \pm 0.6) \times 10^3$ |
| Doxycycline hyclate | $(2.6 \pm 0.9) \times 10^4$ |
| Procaine hydrochloride | $(9.8 \pm 0.5) \times 10^5$ |
| Aminophylline | $(6.5 \pm 0.1) \times 10^4$ |
| Promethazine hydrochloride | $(1.9 \pm 0.1) \times 10^5$ |
| Propranolol hydrochloride | $(1.2 \pm 0.2) \times 10^6$ |
| Neostigmine bromide | $(2.5 \pm 0.7) \times 10^5$ |
| Pyridostigmine bromide | $(1.9 \pm 0.6) \times 10^5$ |
| Vancomycin hydrochloride | $(4.4 \pm 0.3) \times 10^4$ |
| Amoxicillin | $(2.2 \pm 0.6) \times 10^3$ |
| Chloramphenicol | $(1.5 \pm 0.3) \times 10^3$ |
| Diclofenac sodium salt | $(3.8 \pm 1.1) \times 10^4$ |
| Morphine sulfate pentahydrate | $(5.3 \pm 0.4) \times 10^5$ |
| Acetaminophen | $(5.9 \pm 0.5) \times 10^3$ |
| Ranitidine hydrochloride | $(5.5 \pm 0.9) \times 10^6$ |
| Clonidine | $(9.3 \pm 0.9) \times 10^5$ |
| Imipramine hydrochloride | $(8.2 \pm 0.9) \times 10^5$ |
| Amlodipine besylate | $(1.7 \pm 0.2) \times 10^5$ |
| Cefepime hydrochloride | $(4.6 \pm 0.5) \times 10^3$ |
| Nicardipine hydrochloride | $(7.7 \pm 1.4) \times 10^3$ |

As will be apparent from the present figures and description, the binding affinity to the drugs targeted for reversal is high. As far as ketamine reversal of intoxication is concerned, we have conducted additional experiments in rodents that confirm efficacy: In 13 rats, we quantified by brain function monitoring reversal of ketamine anesthesia during continuos infusion of ketamine, titrated to abolishment of response to tail clamping. These rats were administered an escalating Calabadion 2 dose (20, 40, 60, 80 mg/kg/min infusion) over a period of 5 minutes each (n=10) or a 20 minute saline infusion of equivalent volume (n=3). Changes in total EEG power, and mean arterial pressure (MAP) were quantified in response to test drug injection in comparison to baseline (steady state ketamine). Treatment with Calabadion 2 induced a dose-dependent decrease in total EEG power to 66±2% of the baseline EEG-power, indicating reversal of ketamine's typical effects on EEG-power. In parallel, Calabadion 2 injection resulted in a dose dependent increase in MAP to almost 140% compared to baseline at the highest dose (n=10), also indicating reversal of ketamine anaesthesia. No significant changes in EEG-power or MAP were observed during placebo infusion (n=3).

In 13 other rats, we quantified by brain function monitoring reversal of ketamine anesthesia during continuos infusion of ketamine, titrated to abolishment of response to tail clamping. These rats were administered an escalating Calabadion 2 dose (20, 40, 60, 80 mg/kg/min infusion) over a period of 5 minutes each (n=10) or a 20 minute saline infusion of equivalent volume (n=3). Changes in total EEG power, and mean arterial pressure (MAP) were quantified in response to test drug injection in comparison to baseline (steady state ketamine). Treatment with Calabadion 2 induced a dose-dependent decrease in total EEG power to 66±2% of the baseline EEG-power, indicating reversalr of ketamine's typical effects on EEG-power. In parallel, Calabadion 2 injection resulted in a dose dependent increase in MAP to almost 140% compared to baseline at the highest dose (n=10), also indicating reversal of ketamine anaesthesia. No significant changes in EEG-power or MAP were observed during placebo infusion (n=3).

To evaluate the effects of Calabadion 2 on lower, sub-anesthetic concentrations of ketamine we tested the hypotheses that Calabadion 2 affects the ketamine induced hyperlocomotion- and coordination-impairment. Ketamine administration is used as an animal model for schizophrenia, and psychotic symptoms are frequently reported during recovery. We administered Calabadion 2 (1000 mg/kg) i.p. compared to placebo (saline) after an intramuscular anesthetic ketamine bolus (50 mg/kg i.m.) in seven freely behaving Sprague-Dawley rats, and evaluated hyperlocomotion in the open field test in freely behaving rats. Hyperlocomotion was defined as increased length of total path traveled. In the open field test has been used previously to quantify the effects of treatments for schizophrenia in rodents.

After injection of ketamine and Calabadion 2 or placebo, the animals were placed in the center of the dedicated field and the total length of the traveled path was measured. Assessment of psychosis following ketamine anesthesia showed an earlier recovery of normal activity (p<0.05) with faster loss of hyperlocomotion (p<0.001) after calabadion administration observed in time mobile and body rotations.

Accordingly, these data show that calabadions not only reverse ketamine anesthesia but reverse its psychotropic side effects. In vitro binding affinity of calabadion 2 to cocaine•HCl of $(1.0\pm0.1)\times10^6$, methamphetamine $(4.3\pm1.0)\times10^6$, phencyclidine $(2.1\pm0.1)\times10^5$, ketamine $3.7\times10^4$, and morphine ($Ka=5.3\times10^5$ $M^{-1}$ (Ka values in units 1/Molar), in combination with our finding that calabadion 2 clinically reverses ketamine intoxication in the rat demonstrates applicability of the method to intoxication with these agents. It is expected the approach described herein will be used widely in the areas of clinical psychiatry, perioperative medicine, and emergency medicine.

EXAMPLE 7

This Example provides a demonstrations of cocaine and methamphetamine reversal.

Animals.

All experiments involving rats (12 male Sprague-Dawley rats) were conducted after approval was obtained from the Subcommittee on Research Animal Care at Massachusetts General Hospital, Boston, Mass. (Protocol 2011N00181). All institutional guidelines for animal care and usage for research purposes were followed.

Instrumentation.

Prior to all testing the animals were anesthetized using 1.5% isoflurane for placement of an i.v. catheter into one lateral tail vein. After placement of the catheter the isoflurane was turned off and 30 minutes were given to the rat to regain full consciousness. The catheter was removed after completion of the drug injection prior to any behavioral study.

Effects of Calabadion 2 on Cocaine Induced Enhanced Locomotor Activity.

In this randomized controlled crossover study we evaluated the effect of Calabadion 2 on cocaine induced enhanced locomotor activity in rats. A total of six male Sprague Dawley rats were tested 4 times each: A Calabadion 2 (105 mg/kg (low dose) or 210 mg/kg (high dose)) or placebo i.v.-injection, assigned in a randomized order was applied prior to a single bolus of cocaine (1 mg/kg i.v.). The baseline locomotor activity was assessed in all rats with a fourth testing consisting of just injecting saline prior to the open field test in the same experimental setting.

Effects of Calabadion 2 on methamphetamine induced enhanced locomotor activity.

In this randomized controlled crossover study we evaluated the effect of Calabadion 2 on methamphetamine induced enhanced locomotor activity in rats. A total of six male Sprague Dawley rats were used to show the effects of Calabadion 2 on methamphetamine (4 testings each): A Calabadion 2 (65 mg/kg (low dose) or 130 mg/kg (high dose)) or placebo injection, assigned in a randomized order was followed by a single bolus of methamphetamine (0.3 mg/kg i.v.). The baseline locomotor activity was assessed in all rats in a separate testing where only saline was injected.

Open Field Test.

Each animal was placed within one minute after the injection in a 1 m²-sized open field, where they were left undisturbed.

The total distance traveled in the open field as well as the mobile-time were quantified within the next 20 minutes by the video tracking system ANY-maze (Stoelting, Wood Dale, Ill., USA).

Statistical Analysis.

Data is reported as means±SD unless otherwise specified. Statistical analysis was performed using SPSS 22.0 (SPSS Inc. Chicago, Ill.) and STATA 13 (StataCorp LP, College Station, Tex., USA). The main effect of Calabadion 2 was analyzed using a linear mixed model (compound symmetry) for repeated measures. In this model we quantified the main effect of a high dose of Calabadion 2 compared to placebo on the traveled distance and mobile-time. Dose dependency was assessed using another linear mixed model (compound symmetry) for repeated measures comparing the main effect of the low dose Calabadion 2, high dose Calabadion 2 or placebo application prior to injection of the illicit drug. The efficiency of the prevention was quantified by analyzing the main effect of the high dose compared to the individual baseline using a linear mixed model (compound symmetry) for repeated measures.

Effects of Calabadion 2 on Cocaine Induced Enhanced Locomotor Activity.

In particular, the application of cocaine increased the locomotor activity in rodents, quantified as total distance traveled as well as mobile-time in the open field test significantly (baseline v.s. placebo: 9.76±2.83 m vs. 33.06±7.57 m, and 102±18 s vs. 379±52 s, respectively, p=0.018). In a linear mixed model we evaluated the main effect of 210 mg/kg Calabadion 2 (high dose) on the locomotor outcomes. Total distance traveled and mobile time decreased significantly after injection of Calabadion 2 (high dose vs. placebo: 14.76±2.90 m vs. 33.06±7.57 m (p=0.008) and 145±39 s vs. 379±52 s (p=0.003), respectively). Including the data from the Calabadion 2 low dose experiment (105 mg/kg; 21.68±5.21 m and 256±59 s) into the model showed that the effect of Calabadion 2 appeared dose-dependent (p=0.006 and p=0.003). We found no statistical significant difference in locomotor outcomes following the baseline testing and Calabadion 2 high dose prior to cocaine injection (p=0.291 and p=0.283, respectively), which suggests that the chosen doses of Calabadion 2 is sufficient to prevent characteristic behavior for cocaine abuse.

Effects of Calabadion 2 on Methamphetamine Induced Enhanced Locomotor Activity.

The total distance traveled as well as the mobile-time, markers for locomotor activity, increase significantly in open field test following placebo & methamphetamine application compared with the baseline testing (baseline vs. placebo: 9.60±2.09 m vs. 35.88±3.32 m, p=0.006, and 136±22 s vs. 521±69 s, p=0.003, respectively).

We found a significant decrease in both total distance and mobile-time from placebo to 130 mg/kg (high dose) Calabadion 2 application prior to injecting 0.3 mg/kg methamphetamine using a linear mixed model (high dose vs. placebo: 8.45±1.28 m vs. 35.88±3.32 m (p=0.002), and 182±34 s vs. 521±69 s; p=0.009, respectively). Adding the experiments where 65 mg/kg Calabadion 2 (low dose) was injected prior to the illicit drug (12.60±3.56 m and 261±60 s) proved that the observed effect occurred dose-dependently (p<0.001 and p<0.001, respectively). The pretreatment with Calabadion 2 was sufficient since there was no statistical difference between high dose Calabadion 2 and baseline (p=0.588 and p=0.196).

Thus, it is apparent from the foregoing that Calabadion 2 reverses behavioral effects of cocaine and methamphetamine dose-dependently in rats.

EXAMPLE 8

This Example provides a demonstration of ketamine reversal. Animals. All studies on rats (adult male SpragueDawley rats, strain code 400; 294±61 g) were conducted in accordance with the Subcommittee on Research Animal Care at Massachusetts General Hospital, Boston, Mass. (Protocol 2011N00181).

Instrumentation of Sprague-Dawley Rats.

For placement of i.v.s, animals were anesthetized with 1.5% isoflurane. Temperature was controlled rectally and maintained at 37±1° C. using a thermostat controlled heating pad. All rats were instrumented with IV lines and rats undgoing electroencephalohraphic measuremets were instrumented with two i.v. lines, an arterial line and a tracheal tube.

Effects of Calabadion 2 on Electrographic Metrics of Unconsciousness During Constant Anesthetic Infusion.

Calabadion 2's effects on ketamine evoked unconsciousness were investigated by analyzing changes in electrical brain activity, using an epidural EEG-electrode in 13 chronically instrumented rats.

We quantified the total EEG power during a continuous ketamine infusion titrated to abolishment of response to tail clamping. After all surgical procedures were completed the dose of isoflurane was stepwise reduced and discontinued while a 0.67 mg/kg/min ketamine infusion was started. After 10 min of a sole ketamine infusion, we applied intermittent standardized tail-clamping (25N) every 2 min to identify depth of anesthesia. Depending on response, the infusion rate was increased or decreased by 0.33 mg/kg/min, until no response to 6 consecutive tail clamps during a constant dose of ketamine were observed. After steady state recordings, we administered an escalating Calabadion 2 infusion with 20, 40, 60 and 80 mg/kg/min over a period of 5 min each with 40 sec breaks in-between (n=10) or a saline infusion of equivalent volume and timing (n=3). EEG and arterial blood pressure were continuously measured throughout the experiment. EEG recordings were analogously filtered between 0.3 and 300 Hz, and digitized with a bandpass filter between 0.5 and 55 Hz. The spectrum of visually identified artifact free episodes was then calculated using a Fast-Fourier-Transformation with a 1024 bit Hann (cosine-bell) window. Changes in total EEG power and MAP were quantified in response to test drug injection in comparison to steady state ketamine. To ensure that the observed effects were not caused by an interaction of Calabadion 2 with isoflurane, we administered increasing amounts of Calabadion 2 (20, 40, 60 and 80 mg/kg/min for 5 min each) in 3 rats anesthetized with a constant isoflurane anesthesia titrated to the abolishment of tail-clamping and quantified EEG power, mean arterial blood pressure and heart rate. Additionally we administered an escalating phenylephrine infusion (4 to 10 µg/kg/min) in 3 rats anesthetized with a continuous ketamine infusion, to ensure that our changes in EEG can be interpreted as a result of shallower anesthesia, rather than nonspecific hemodynamic reactions.

Effects of Calabadion 2 on Time to Regain Righting Reflex Following Ketamine Anesthesia.

We examined the effects of Calabadion 2 on time to recovery from loss of righting reflex (LORR) following a single i.v. bolus of ketamine in 14 adult male Sprague-Dawley rats. After instrumentation, animals receive a one minute infusion of ketamine (30 mg/kg). Once placed in the supine position, animals were randomized to receive either an i.v. infusion of Calabadion 2 (80 mg/kg/min dissolved in distilled H2O) or saline, beginning 3 min following the anesthetic injection. Recovery from LORR was taken as the moment when the rat regained a standing or sternally recumbent position.

Effects of Calabadion 2 on Functional Mobility after Ketamine Anesthesia on the Balance Beam.

Recovery of functional mobility impairment was quantified using the balance beam test, a common method to assess motor coordination and balance of animals, used as a predictor for pharmacologic impact on recovery. The time rats remained on a wooden rod (diameter 2.5 cm) was measured to evaluate balance and body strength. After recovery from LORR animals were placed on the beam every 4 min starting at the i.v. anesthetic agent injection, or every 10 min starting at the i.m. ketamine injection. Test performance was scored after Combs et al. by a blinded team member. The time to recovery of balance was defined as the first time the animals achieved a test score of 3 (able to remain on beam >20 s or reaches support).

Statistical Analysis.

All data is reported as means±SEM unless otherwise specified. Statistical analysis was performed using SPSS 22.0 (SPSS Inc. Chicago, Ill.) and GraphPad Prism 6.0 (GraphPad Software, Inc. LaJolla, Calif.). EEG/BSR and blood pressure changes were analysed using a mixed linear model (compound symmetry repeated covariance) with an identity link function for normally distributed probability. We tested for an interaction of the reversal agent and its dose on the dependent variable EEG power for the reversal of ketamine. The same model was used to evaluate the effects on blood pressure. We used a paired t-test to assess differences in recovery time after ketamine anesthesia when administering Calabadion 2 compared to placebo. To evaluate the effect on post-anesthetic ketamine induced balance- and coordination impairment, we used a mixed model (compound symmetry repeated covariance) with a logit link function for binomially distributed probability, and tested for an interaction of reversal agent and time on recovery of balance as defined by a score of 3.

Results of the Ketamine Reversal Experiments

Electroecephalographic evidence. Ascending levels of ketamine gradually increase EEG power. During continuous ketamine infusion titrated to abolish responses to a noxious stimulus (tail clamping), Calabadion 2 induced a dose-dependent decrease in total EEG power to 63.1±3.9% of steady-state-ketamine EEGpower, indicating that Calabadion 2 reversed the typical effects of ketamine in the EEG (n=10, P<0.001, FIG. 72). In parallel, Calabadion 2 injection resulted in a dose dependent increase in MAP to almost 140% compared to pre-ketamine baseline (96.1 mmHg) at the highest dose (n=10), also indicating reversal of anesthesia (P<0.001, FIG. 72). No significant changes in EEG-power (n=3) or MAP (n=3) were observed during placebo infusion (FIG. 72).

In contrast, continuous phenylephrine infusion during steady state shallow ketamine anesthesia resulted in significant MAP increases without effects on EEG power (n=3, P=0.024). We did not observe any effects of Calabadion 2 on EEG-power, BSR and MAP during and after the highest dose of the stepwise increasing Calabadion 2 infusion when administered during constant isoflurane anesthesia.

Effects of Calabadion 2 on Time to Emergence from Anesthesia.

Emergence from ketamine anesthesia was assessed by measuring time to recovery from LORR, frequently used as a predictor for the level of anesthesia. Relative to saline, Calabadion 2 significantly decreased the time to recovery from LORR by about 30% in ketamine anesthetized rats (mean±SD; 6.0±0.7 min vs. 8.4±1.6 min, n=7, P=0.023, FIG. 73). The median dose of Calabadion 2 required to achieve the described accelerated recovery from LORR with a 50% probability (ED50) was 983.5 mg/kg [95% CI 976.1-991.3] and 166.6 mg/kg [95% CI 160.9-172.9] for the reversal of a 4 mg/kg i.v. etomidate bolus and a 30 mg/kg i.v. bolus of ketamine, respectively.

Effects of Calabadion 2 on Post-Anesthesia Functional Mobility Impairment.

We observed a significantly faster recovery of balance, indicated by a balance score of 3 (see Combs et al), when injecting Calabadion after anesthesia compared to placebo. Calabadion 2 significantly reduced time to full recovery to 37.4±2.1 min after 30 mg/kg ketamine i.v. (n=7, P=0.009) and to 74.3±3.7 min after 50 mg/kg ketamine i.m. (n=7, P<0.001) as compared to 92.9±5.7 min compared with placebo reversal (FIG. 74). The faster recovery of balance suggests a faster recovery of muscle strength and/or motor coordination after Calabadion 2 injection for ketamine

EXAMPLE 9

This Example provides a demonstration of reversal of the effects of an opioid. Male SpragueDawley rats were used and were obtained from Charles River Laboratories (Wilmington, Mass.) and housed in the Massachusetts General Hospital Center for Comparative Medicine Animal Facility. Femoral artery catheters were preimplanted by the vendor in some animals. Drugs were administered through a 24G lateral tail vein catheter. Calabadion 2 was solubilized in sterile distilled deionized H2O (100 mg/ml) with gentle warming. Fentanyl citrate and naloxone (both U.S.P Grade) were obtained from McKesson Medical-Surgical (Richmond, Vir.). Fentanyl was given by infusion (KDS model 200 series infusion pump; KDScientific).

Rat Arterial Blood Gas Studies, Rats were restrained in an acrylic chamber (3 inch diameter). The chamber had multiple perforations for room air exchange and was flushed, additionally, via a luer port with 2 liters/min air. Following tail vein catheterization under brief isoflurane anesthesia (3 to 5%) and at least 15 minutes recovery and chamber acclimation, calabadion 2 was injected. A baseline arterial blood sample (~100 microliters) in a heparinized syringe was take for arterial blood gas analysis. Fentanyl citrate (50 mcg/kg, IV) was administered by infusion over 15 mins. On completion of the infusion, a second arterial blood sample was taken. Rats were repeat studied and recovered at least 3 days between study sessions. Arterial blood was analyzed promptly using CG4+ cartridges in a Vetscan iStat 1 (Abaxis, Union City, Calif.) blood gas analyzer Results.

The results are provided in FIG. 75. Fentanyl induces a respiratory depression leading to a substantial decrease in pH and arterial carbon dioxide concentration. Calabadion 2 decreases the respiratory depressant effects of fentanyl in a dose dependent fashion such that values of pH and arterial carbon dioxide concentration observed at calabadion 100 mg/kg with fentanyl did not differ from values observed at baseline in the absence of opioid effects.

Rat Breathing Studies. Studies were conducted in anesthetized rats spontaneously breathing 1.5% isoflurane in air. Following intubation and tail vein catheterization, baseline breathing was measured for at least 15 minutes. Fentanyl citrate (25 mcg/kg IV) was infused over 30 minutes. 15 minutes into the fentanyl infusion, Calabadion 2 (100 mg/kg IV bolus) was administered; 5 minutes later naloxone (1 mg/kg IV bolus) was administered. In these studies, rats were orally, endotracheally intubated with a 14G angiocatheter, which was connected by T-piece to tubing continuously flushed (1 l/min) with air using a mass flow controller valve (Model GE50A, MKS Instruments Inc., Andover, Mass.). Changes in gas flow induced by rat breathing were detected using a heated pneumotachometer (Model 8420; Hans Rudolph Inc., Shawnee, Kans.). Gas flow was converted to an analog signal with a differential pressure transducer and a demodulator (Models CD15 and MP45-14-871; Validyne Engineering, Northridge, Calif.). The system was calibrated using a rodent ventilator (Harvard Apparatus, Model 683). Data acquisition, analysis, and gas flows were controlled using LabView 2013 software (National Instruments, Austin, Tex.) run on an Apple computer interfaced with multiple USB-6009 data acquisition boards (National Instruments). Data were analyzed in 4 second time epochs to quantify minute ventilation. Inhaled gas composition was monitored with a CAPSTAR-100 carbon dioxide analyzer (CWE, Inc, Ardmore, Pa.). Rat temperature was maintained at 37C using a rectal thermistor-controlled heat lamp.

Results.

The results are provided in FIG. 76. Fentanyl (blue horizontal bar) induced a dose-dependent decrease in minute ventilation and an increase in end-tidal carbon dioxide concentration (ETCO2). Following calabadion injection end-tidal carbon dioxide and minute ventilation normalized to values observed at baseline and the specific opioid receptor antagonist naloxone had lower recovering effects on these variables of recovery of spontaneous breathing than the previous calabadion injection.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

We claim:

1. A method for treating an individual in need of treatment for intoxication from ingestion of a drug, wherein the drug is selected from the group consisting of cocaine, fentanyl, methamphetamine, and combinations thereof, comprising administering to the individual a composition comprising a compound having the following structure, or a salt thereof, a partial salt thereof, or a mixture thereof, a stereoisomer thereof, or combinations thereof:

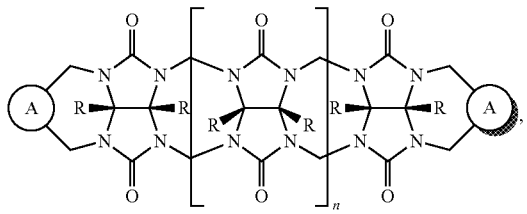

wherein each R is independently hydrogen, $C_1$ to $C_{20}$ alkyl group, $C_3$ to $C_{20}$ carbocyclic group, $C_1$ to $C_{20}$ heterocyclic group, carboxylic acid group, ester group, amide group, hydroxy group or ether group;

wherein, optionally, adjacent R groups form a $C_3$ to $C_{20}$ carbocyclic ring or heterocyclic ring;

wherein each

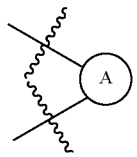

is independently a $C_5$ to $C_{20}$ carbocyclic ring system or $C_2$ to $C_{20}$ heterocyclic ring system, wherein the ring system comprises one or more rings;

wherein at least one ring system has at least one solubilizing group selected from sulfonic acid group, sulfonate salt group, phosphonic acid group, phosphonate salt group, and polyethylene glycol group;

wherein, optionally, the ring system has a targeting group; and wherein n is 1 to 5.

2. The method of claim 1, wherein each

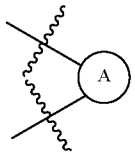

is independently a $C_5$ to $C_{20}$ carbocyclic ring having one of the following structures:

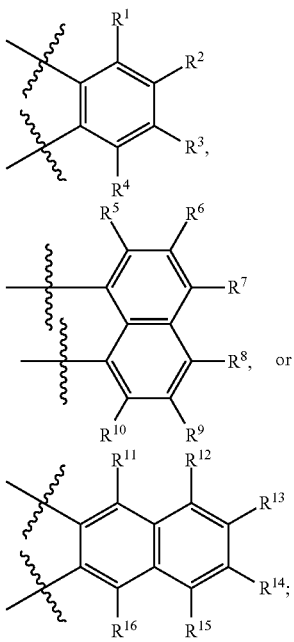

wherein at each occurrence of

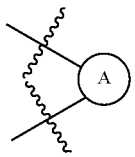

$R^1$ to $R^{16}$ is independently hydrogen, $C_1$ to $C_{20}$ alkyl group, halo group, hydroxyl group, nitro group, carboxylic acid group, ester group, amide group, ether group, $C_3$ to $C_{20}$ carbocyclic group, or $C_1$ to $C_{20}$ heterocyclic group, provided that at least one of $R^1$ to $R^{16}$ in the compound has the following structure:

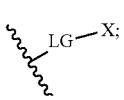

wherein LG is a linking group and X is the solubilizing group; and wherein optionally one or more adjacent $R^1$ to $R^{16}$ groups are connected forming a carbocyclic ring or heterocyclic ring.

3. The method of claim 2, wherein has the following structure:

wherein each i is 1 to 20.

4. The method of claim 2, wherein at least one of the $R^1$ to $R^{16}$ groups in the structure has the following structure and wherein LG is a linking group and wherein TG is the targeting group.

5. The method of claim 2, wherein the groups are the same.

6. The method of claim 2, wherein the compound has one of the following structures

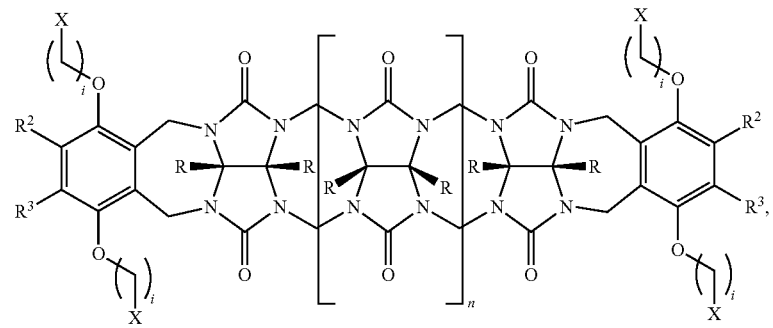

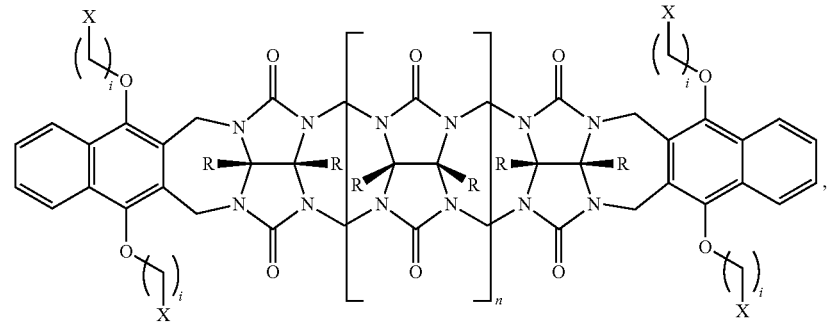

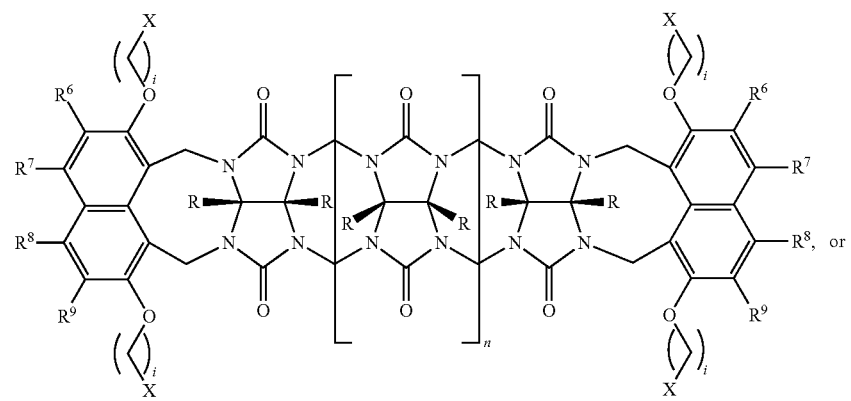

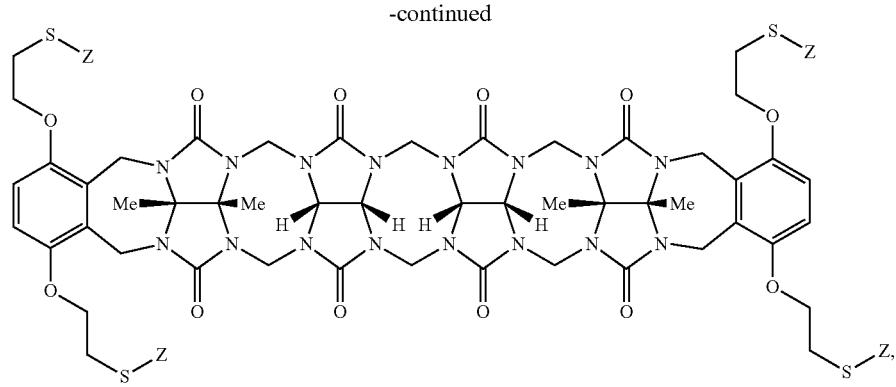
wherein Z is PEG group having a molecular weight of 200 to 10,000.
7. The method of claim 1, wherein the compound has one of the following structures:
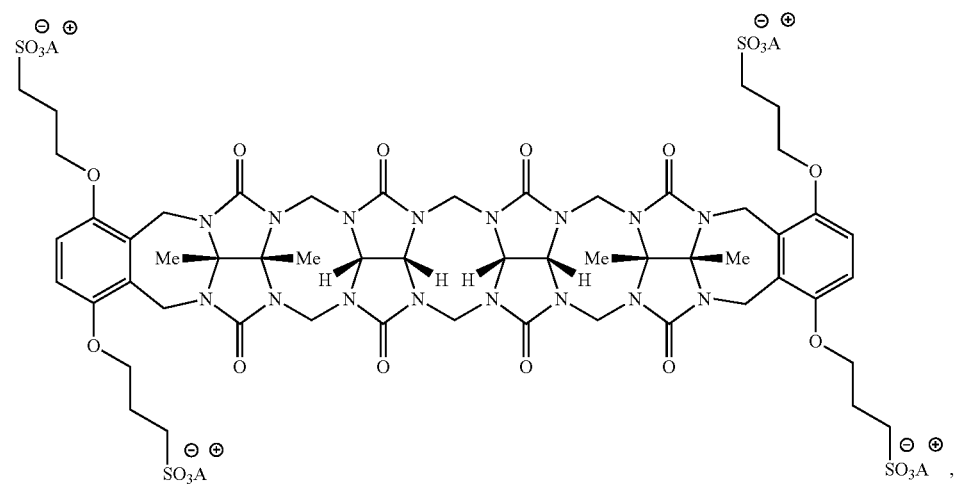
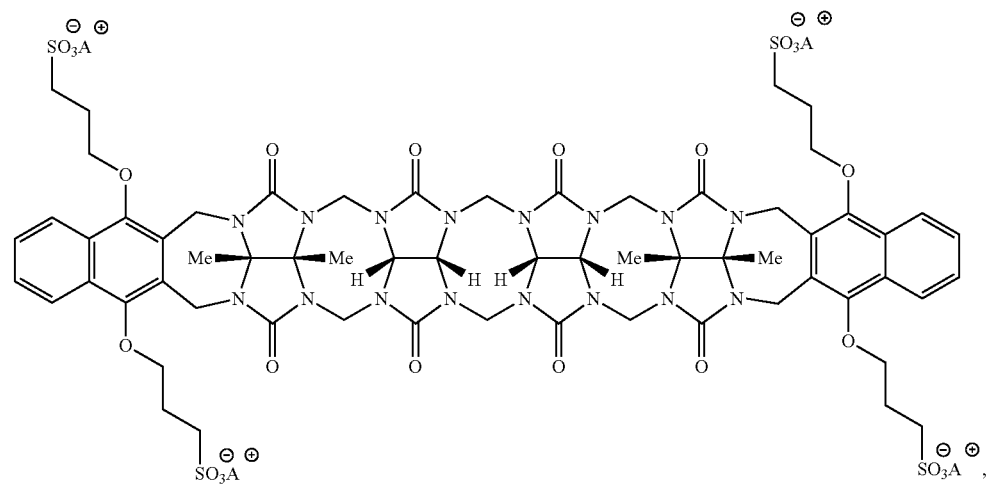

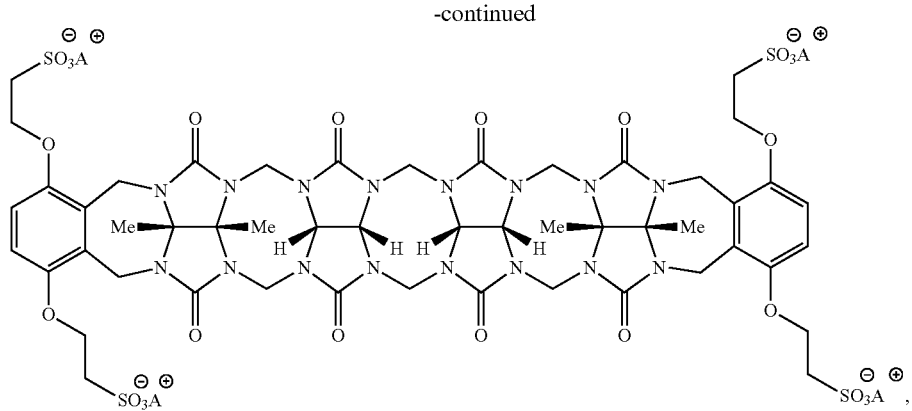
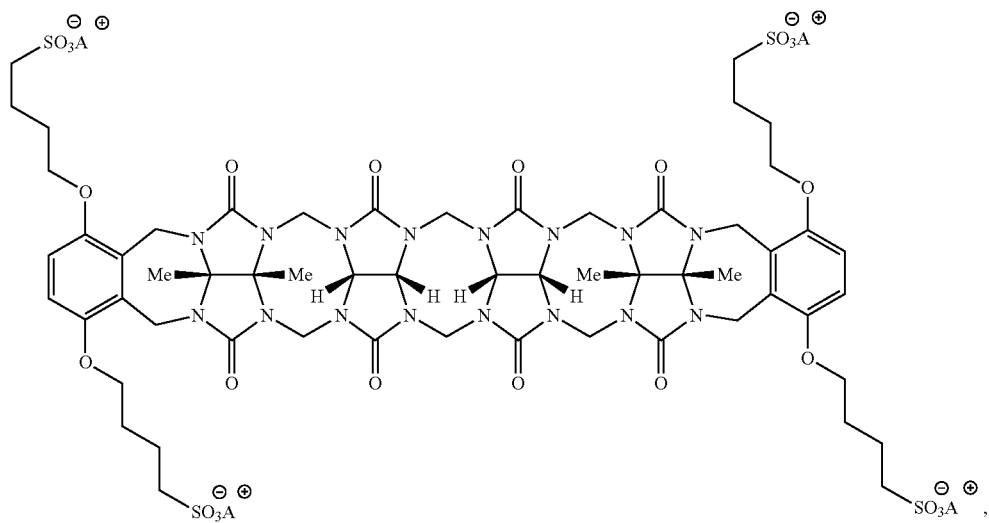
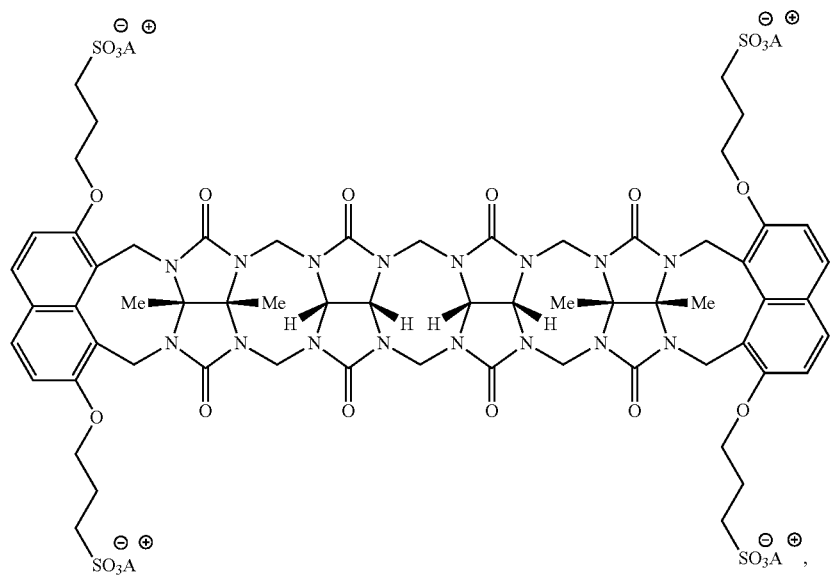

-continued

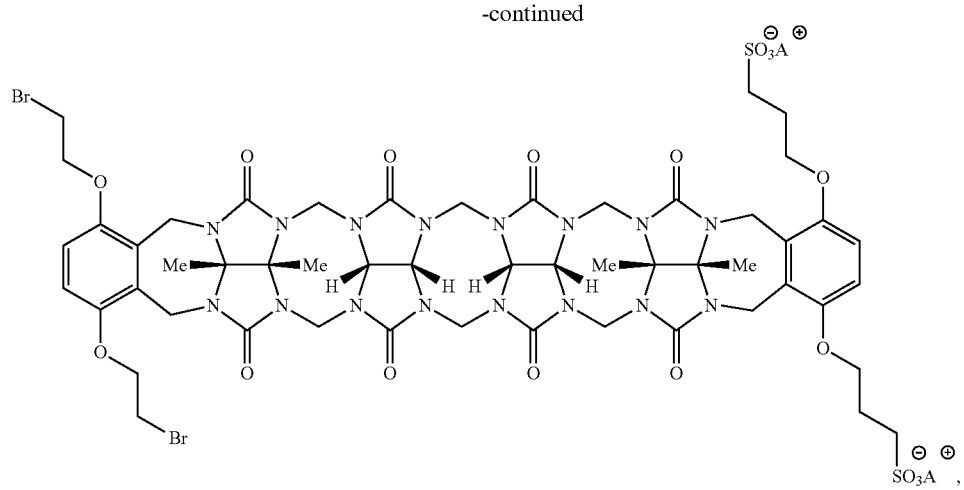

wherein A⁺ is H⁺, Na⁺, K⁺, Ca²⁺, Mg²⁺, Zn²⁺, H₄N⁺, Et₃NH⁺, Me₄N⁺, (HOCH₂CH₂)₃NH⁺, or a cationic form of ethylenediamine, piperazine, and trishydroxymethyl aminomethane (TRIS).

8. The method of claim 1, wherein the individual is in need of treatment for ingestion of cocaine.

9. The method of claim 1, wherein the individual is in need of treatment for ingestion of fentanyl.

10. The method of claim 1, wherein the individual is need of treatment for ingestion of methamphetamine.

11. The method of claim 1, wherein the individual in need is a human.

12. The method of claim 1, wherein the individual in need is a non-human mammal.

13. A kit comprising a pharmaceutical composition comprising the compound of claim 1 in one or more containers, the kit further comprising printed material providing an indication the composition is for use in treatment for ingestion of cocaine, fentanyl, methamphetamine, or a combination thereof.

14. The kit of claim 13, further comprising a needle and syringe.

* * * * *